United States Patent
Yukimasa et al.

(10) Patent No.: US 9,708,338 B2
(45) Date of Patent: Jul. 18, 2017

(54) AROMATIC HETEROCYCLYLAMINE DERIVATIVE HAVING TRPV4-INHIBITING ACTIVITY

(71) Applicant: Shionogi & Co., Ltd., Osaka (JP)

(72) Inventors: Akira Yukimasa, Osaka (JP); Naoki Tsuno, Osaka (JP); Motohiro Fujiu, Osaka (JP); Hiroki Yamaguchi, Osaka (JP); Hiromi Kudo, Osaka (JP); Tatsuhiko Ueno, Osaka (JP); Yusuke Ichihashi, Osaka (JP); Takatsugu Inoue, Osaka (JP); Shinji Suzuki, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 15/076,728

(22) Filed: Mar. 22, 2016

(65) Prior Publication Data

US 2016/0200721 A1 Jul. 14, 2016

Related U.S. Application Data

(63) Continuation of application No. PCT/JP2014/075178, filed on Sep. 24, 2014.

(30) Foreign Application Priority Data

Sep. 25, 2013 (JP) .................... 2013-198310
May 30, 2014 (JP) .................... 2014-112826

(51) Int. Cl.
| | | |
|---|---|---|
| A61K 31/443 | (2006.01) | |
| A61K 31/4436 | (2006.01) | |
| A61K 31/4439 | (2006.01) | |
| A61K 31/496 | (2006.01) | |
| A61K 31/506 | (2006.01) | |
| C07D 401/14 | (2006.01) | |
| C07D 413/14 | (2006.01) | |
| C07D 417/14 | (2006.01) | |
| C07D 471/08 | (2006.01) | |
| C07D 498/08 | (2006.01) | |
| C07D 513/08 | (2006.01) | |
| C07D 491/08 | (2006.01) | |
| C07D 491/107 | (2006.01) | |
| C07D 471/04 | (2006.01) | |
| C07D 487/04 | (2006.01) | |
| C07D 491/10 | (2006.01) | |
| C07D 498/10 | (2006.01) | |

(52) U.S. Cl.
CPC ......... *C07D 491/08* (2013.01); *C07D 417/14* (2013.01); *C07D 471/04* (2013.01); *C07D 471/08* (2013.01); *C07D 487/04* (2013.01); *C07D 491/10* (2013.01); *C07D 491/107* (2013.01); *C07D 498/08* (2013.01); *C07D 498/10* (2013.01); *C07D 513/08* (2013.01)

(58) Field of Classification Search
CPC .............. A61K 31/443; A61K 31/4436; A61K 31/4439; A61K 31/496; A61K 31/506; C07D 401/14; C07D 413/14; C07D 417/14; C07D 471/08; C07D 498/08; C07D 513/08
USPC .... 514/230.5, 249, 252.03, 253.1, 269, 274, 514/275, 292, 304, 318, 342; 544/105, 544/238, 295, 298, 310, 316, 331, 349, 544/364; 546/81, 125, 193, 270.7
See application file for complete search history.

(56) References Cited

U.S. PATENT DOCUMENTS

2015/0038483 A1  2/2015 Yukimasa et al.

FOREIGN PATENT DOCUMENTS

| JP | 2009-84209 | 4/2009 |
|---|---|---|
| WO | 2005/068444 | 7/2005 |
| WO | 2006/038070 | 4/2006 |
| WO | 2007/008541 | 1/2007 |
| WO | 2007/059608 | 5/2007 |
| WO | 2007/071055 | 6/2007 |
| WO | 2007/115403 | 10/2007 |
| WO | 2007/115408 | 10/2007 |
| WO | 2007/115409 | 10/2007 |

(Continued)

OTHER PUBLICATIONS

Database Registry, Jul. 13, 2004, Retrieved from STN on Sep. 20, 2016, RN 708998-40-7.*

(Continued)

*Primary Examiner* — Brenda Coleman
(74) *Attorney, Agent, or Firm* — Wenderoth, Lind & Ponack, L.L.P.

(57) ABSTRACT

The present invention is related to a compound represented by formula (I)

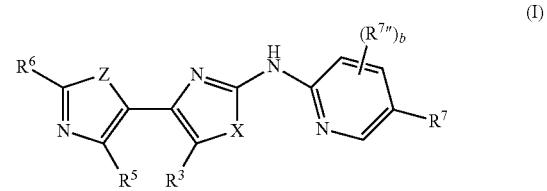

wherein —X— is —NH— or —S—; —Z— is —O— or —S—; $R^3$, $R^5$ and $R^6$ are each independently a hydrogen atom, substituted or unsubstituted alkyl, or the like; $R^7$ is a cyano, substituted or unsubstituted amino, or the like; $R^{7'}$ is each independently a halogen; b is 0 or 1; or a pharmaceutically acceptable salt thereof, or a pharmaceutical composition comprising thereof.

10 Claims, No Drawings

(56) References Cited

FOREIGN PATENT DOCUMENTS

| WO | 2007/115410 | 10/2007 |
|---|---|---|
| WO | 2008/144931 | 12/2008 |
| WO | 2009/111680 | 9/2009 |
| WO | 2009/146177 | 12/2009 |
| WO | 2009/146182 | 12/2009 |
| WO | 2010/011912 | 1/2010 |
| WO | 2010/011914 | 1/2010 |
| WO | 2011/091407 | 7/2011 |
| WO | 2011/091410 | 7/2011 |
| WO | 2011/119693 | 9/2011 |
| WO | 2011/119694 | 9/2011 |
| WO | 2011/119701 | 9/2011 |
| WO | 2011/119704 | 9/2011 |
| WO | 2012/068209 | 5/2012 |
| WO | 2012/144661 | 10/2012 |
| WO | 2012/174340 | 12/2012 |
| WO | 2012/174342 | 12/2012 |
| WO | 2013/012500 | 1/2013 |

OTHER PUBLICATIONS

Database Registry, Jul. 13, 2004, Retrieved from STN on Sep. 20, 2016, RN 708992-43-2.*
Database Registry, Dec. 15, 2004, Retrieved from STN on Sep. 20, 2016, RN 797776-30-8.*
Wouter Everaerts et al., The vanilloid transient receptor potential channel TRPV4: From structure to disease, Biophysics & Molecular Biology, vol. 103, 2010, pp. 2-17.
Christopher D. Benham et al., TRPV channels as temperature sensors, Cell Calcium, vol. 33, 2003, pp. 479-487.
Tomohiro Numata et al., Structures and Variable Functions of TRP Channels, Seikagaku, vol. 81, No. 11, 2009, pp. 962-983.
Makoto Tominaga, TRP Channels and Nociception, Nichiyakurishi, vol. 127, 2006, pp. 128-132.
Makoto Suzuki, TRP4 as a Mechano-Sensing Channel, Seibutsu Butsuri, vol. 45(5), 2005, pp. 268-271.
Mimi N. Phan et al., Functional Characterization of TRPV4 as an Osmotically Sensitive Ion Channel in Porcine Articular Chondrocytes, Arthritis & Rheumatism, vol. 60, No. 10, 2009, pp. 3028-3037.
Fabien Vincent et al., Identification and characterization of novel TRPV4 modulators, Biochemical and Biophysical Research Communications, vol. 389, 2009, pp. 490-494.
Wouter Everaerts et al , Inhibition of the cation channel TRPV4 improves bladder function in mice and rats with cyclophosphamide-induced cystitis, Proceedings of the National Academy of Sciences, vol. 107, No. 44, 2010, pp. 19084-19089.
Sarah E. Skerratt et al., Identification of false positives in "HTS hits to lead": The application of Bayesian models in HTS triage to rapidly deliver a series of selective TRPV4 antagonists, MedChemComm, vol. 4, 2013, pp. 244-251.
Serena Materazzi et al., TRPA1 and TRPV4 mediate paclitaxel-induced peripheral neuropathy in mice via a glutathione-sensitive mechanism, Pflugers Arch., vol. 463, 2012, pp. 561-569.
Elodie Martin et al., Involvement of TRPV1 and TRPV4 channels in migration of rat pulmonary arterial smooth muscle cells, Pflugers Arch., vol. 464, 2012, pp. 261-272.
Fabien Vincent et al., TRPV4 Agonists and Atagonists, Current topics in Medicinal Chemistry, vol. 11, 2011, pp. 2216-2226.
Samantha Leone et al., SAR and QSAR study on 2-aminothiazole derivatives, modulators of transcriptional repression in Huntington's disease, Bioorganic & Medicinal Chemistry, vol. 16, 2008, pp. 5695-5703.
Database Registry, Apr. 5, 2010, Retrieved from STN international [online] ;retrieved on Oct. 29, 2014, RN 1217018-68-2.
Database Registry, Nov. 11, 2002, Retrieved from STN international [online] ;retrieved on Oct. 29, 2014, RN 472981-35-4, 472981-13-8, 472980-50-0, 472980-45-3, 472979-34-3,472979-22-9.
Database Registry, Oct. 29, 2010, Retrieved from STN international [online] ;retrieved on Oct. 29, 2014, RN 467236-86-8.
Database Registry, Jan. 22, 2001, Retrieved from STN international [online] ;retrieved on Oct. 29, 2014, RN 315705-88-5, 315705-63-6, 315705-03-4, 315704-37-1.
Database Registry, Apr. 2, 2010, Retrieved from STN international [online] ;retrieved on Oct. 29, 2014, RN 1215546-06-7.
Database Registry, Sep. 17, 2009, Retrieved from STN international [online] ;retrieved on Oct. 29, 2014, RN 1185305-94-5,1185305-50-3, 1185305-28-5,1185305-22-9.
Database Registry, Oct. 20, 2004, Retrieved from STN international [online] ;retrieved on Oct. 29, 2014, RN 765922-23-4.
Database Registry, Oct. 8, 2004, Retrieved from STN international [online] ;retrieved on Oct. 29, 2014, RN 75868917-7.
Database Registry, Nov. 8, 2002, Retrieved from STN international [online] ;retrieved on Oct. 29, 2014, RN 471915-09-0.
Database Registry, Aug. 13, 2002, Retrieved from STN international [online] ;retrieved on Oct. 29, 2014, RN 443747-58-8.
Written Opinion of the International Searching Authority issued Dec. 12, 2014 in corresponding International Application No. PCT/JP2014/075178.
International Search Report issued Dec. 2, 2014 in corresponding International Application No. PCT/JP2014/075178.

* cited by examiner

AROMATIC HETEROCYCLYLAMINE DERIVATIVE HAVING TRPV4-INHIBITING ACTIVITY

TECHNICAL FIELD

The present invention relates to a compound that has a TRPV4 inhibitory activity and is useful for the treatment and/or prevention of a TRPV4 receptor-mediated disorder, or a pharmaceutically acceptable salt thereof, and a pharmaceutical composition containing thereof.

BACKGROUND ART

TRPV4 is one of a cation channel of the TRP (Transient Receptor Potential) superfamily. It was discovered as an osmotic-sensitivity receptor activated by hypotonic stimulus. Then, it was shown that TRPV4 had a temperature-sensitive property, that is, TRPV4 was activated at the body temperature rage, and TRPV4 is activated by heat and low pH. It is reported that the gene and protein of TRPV4 is expressed in brain, spinal code, peripheral nerve fiber, skin, kidney, trachea, cochlea and bone, etc. Moreover, it is also reported that TRPV4 is activated by the compounds, such as arachidonic acid, arachidonate metabolite, endocannabinoids, and phorbol ester. The increase of activation of the C-fiber by hypotonic stimulation under the inflammatory environment induced by inflammatory mediators is known, and it is also reported that TRPV4 relates to this activation. Furthermore, it is also reported that TRPV4 is activated by fluid pressure and mechanical stimuli, and TRPV4 relates to hyperalgesia caused by mechanical stimuli. In addition, it is also reported that TRPV4 relates to paclitaxel-induced pain (Non-patent documents 1 to 5). Therefore, it is expected that TRPV4 participates in many physiological roles. The compound which exhibits high affinity to TRPV4 has a high potential as useful medicine in the therapy and/or prevention of TRPV4 receptor-mediated disorder.

The compounds having TRPV4 inhibitory activity are disclosed in patent-documents 1 to 11, 20 to 25 and non-patent documents 6 to 12. The compounds suggested to be related with TRPV4 are disclosed in patent-documents 12 to 19. However, the compounds of this present invention are not disclosed in any documents.

The derivatives wherein two thiazole rings are directly attached are disclosed in patent-document 26. However, there is neither disclosure nor suggestion about a TRPV4 inhibitory activity.

The compounds having TRPV4 inhibitory activities are disclosed in patent-documents 27, but these compounds which are substantively disclosed have different structures compared to the compound of the present invention.

PRIOR ART REFERENCES

Patent Document

[Patent Document 1] International Publication No. 2009/111680 pamphlet
[Patent Document 2] International Publication No. 2009/146177 pamphlet
[Patent Document 3] International Publication No. 2009/146182 pamphlet
[Patent Document 4] International Publication No. 2010/011912 pamphlet
[Patent Document 5] International Publication No. 2010/011914 pamphlet
[Patent Document 6] International Publication No. 2011/091407 pamphlet
[Patent Document 7] International Publication No. 2011/091410 pamphlet
[Patent Document 8] International Publication No. 2011/119693 pamphlet
[Patent Document 9] International Publication No. 2011/119694 pamphlet
[Patent Document 10] International Publication No. 2011/119701 pamphlet
[Patent Document 11] International Publication No. 2011/119704 pamphlet
[Patent Document 12] International Publication No. 2006/038070 pamphlet
[Patent Document 13] International Publication No. 2007/059608 pamphlet
[Patent Document 14] International Publication No. 2007/071055 pamphlet
[Patent Document 15] International Publication No. 2007/115403 pamphlet
[Patent Document 16] International Publication No. 2007/115408 pamphlet
[Patent Document 17] International Publication No. 2007/115409 pamphlet
[Patent Document 18] International Publication No. 2007/115410 pamphlet
[Patent Document 19] International Publication No. 2008/144931 pamphlet
[Patent Document 20] JP-A No. 2009-084209
[Patent Document 21] International Publication No. 2012/144661 pamphlet
[Patent Document 22] International Publication No. 2012/174340 pamphlet
[Patent Document 23] International Publication No. 2012/174342 pamphlet
[Patent Document 24] International Publication No. 2013/012500 pamphlet
[Patent Document 25] International Publication No. 2012/144661 pamphlet
[Patent Document 26] International Publication No. 2012/068209 pamphlet
[Patent Document 27] International Publication No. 2013/146754 pamphlet

Non-Patent Document

[Non-patent Document 1] Progress in Biophysics and Molecular Biology, 2010, 103, pp. 2-17
[Non-patent Document 2] Cell Calcium, 2003, 33, pp. 79-487
[Non-patent Document 3] Seikagaku, 2009, 81(11), pp. 962-98
[Non-patent Document 4] Folia Pharmacologica Japonica, 2006, 127, pp. 128-132
[Non-patent Document 5] Seibutsu Butsuri, 2005, 45(5), pp. 268-271
[Non-patent Document 6] ARTHRITIS & RHEUMATISM, 2009, 60, pp. 3028-3037
[Non-patent Document 7] Biochemical and Biophysical Research Communications, 2009, 389, pp. 490-494
[Non-patent Document 8] Proceedings of the National Academy of Sciences, 2010, 107, pp. 19084-19089
[Non-patent Document 9] Med Chem Comm, 2013, 4, pp. 244-251
[Non-patent Document 10] Pflugers Arch., 463: 561, 2012
[Non-patent Document 11] Pflugers Arch., 464: 261, 2012
[Non-patent Document 12] Current Topics in Medicinal Chemistry, 2011, 11, 2216-2226

SUMMARY OF THE INVENTION

Problems to be Solved by the Invention

The present invention is to provide a compound that has a TRPV4 inhibitory activities or a pharmaceutically acceptable salt thereof, or a pharmaceutical composition containing thereof that has a TRPV4 inhibitory activities.

Means for Solving the Problem

The present invention relates to a compound that has TRPV4 inhibitory activities and is useful in the treatment and/or prevention of TRPV4 receptor-mediated disorders, or a pharmaceutically acceptable salt thereof.

The present invention relates to the following 1) to 6).

1) A compound of formula (I):

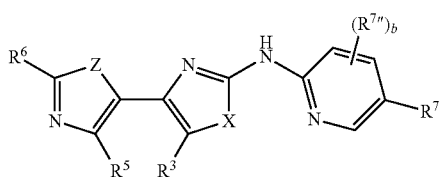

wherein:
—X— is —NH— or —S—;
—Z— is —O— or —S—;
$R^3$, $R^5$ and $R^6$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^7$ is a cyano, substituted or unsubstituted amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkylsulfonyl, substituted or unsubstituted carbamoyl, substituted or unsubstituted sulfamoyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl;
$R^{7'}$ is each independently a halogen;
b is 0 or 1;
or a pharmaceutically acceptable salt thereof.
2) The compound according to the above item 1),
wherein —X— is —S—; —Z— is —S—,
or a pharmaceutically acceptable salt thereof.
3) The compound according to the above item 2),
wherein $R^7$ is a group represented by the following formula:

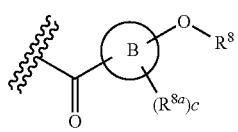

wherein ring B is non-bridged non-aromatic heterocyclyl, or bridged non-aromatic heterocyclyl;
$R^8$ is substituted or unsubstituted alkyl, substituted or unsubstituted alkenyl, substituted or unsubstituted alkynyl, substituted or unsubstituted aromatic carbocyclyl, or substituted or unsubstituted aromatic heterocyclyl;
$R^{8a}$ is each independently halogen, substituted or unsubstituted alkyl, substituted or unsubstituted alkenyl, or substituted or unsubstituted alkynyl;
c is 0, 1, or 2;
or a pharmaceutically acceptable salt thereof.
4) The compound according to the above item 3),
wherein $R^7$ is a group represented by the following formula:

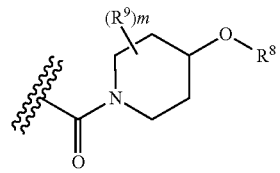

wherein m is 2;
two $R^9$ groups may be taken together to form (C2-C4) bridge;
the carbon atoms that consist of the bridge are each independently substituted with the substituent selected from $R^a$;
$R^a$ is a hydrogen atom, halogen, hydroxy, cyano, substituted or unsubstituted alkyl, substituted or unsubstituted alkenyl, or substituted or unsubstituted alkynyl;
$R^8$ is the same as above;
or a pharmaceutically acceptable salt thereof.
5) A compound of formula (III):

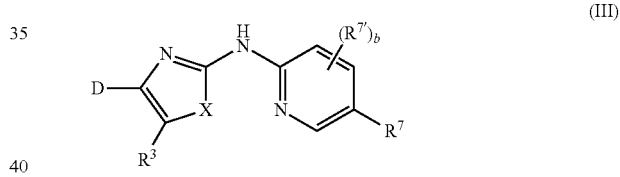

wherein $R^7$ is substituted or unsubstituted non-aromatic heterocyclylcarbonyl;
D is a group represented by the following formula:

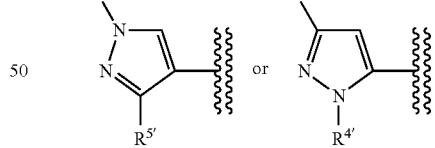

wherein $R^{4'}$ is a hydrogen atom, or substituted or unsubstituted alkyl, substituted or unsubstituted alkenyl, or substituted or unsubstituted alkynyl;
$R^{5'}$ is a hydrogen atom, or substituted or unsubstituted alkyl, substituted or unsubstituted alkenyl, or substituted or unsubstituted alkynyl;
—Z— is —O— or —S—;
$R^3$ is each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{7'}$ is each independently a halogen;

b is 0 or 1;

or a pharmaceutically acceptable salt thereof.

6) A pharmaceutical composition containing the compound according to any one of the above items 1) to 5), or a pharmaceutically acceptable salt thereof.

Effect of the Invention

The present invention provides a compound useful in the treatment and/or prevention of a TRPV4 receptor-mediated disorder, or a pharmaceutically acceptable salt thereof. The compound of the present invention shows an excellent TRPV4 inhibitory activity as described in test examples below. Thus, a pharmaceutical composition of the present invention is available for therapeutic agent and/or prophylactic agent for inflammatory pain (bladder inflammatory pain, pain after tooth extraction, postoperative pain, pain in the low back, periarthritis scapulohumeralis, cervico-omo-brachial syndrome, inflammation of a tendon or a tendon sheath, osteoarthritis, chronic articular rheumatism), neuropathic pain (sciatica, postherpetic neuralgia, diabetic neuropathy), pain related to cancer (cancer pain, bone metastasis pain, pain with the administration of anticancer agent), IBS, inflammatory bowel disease, osteoporosis, articular cartilage degeneration, cerebral stroke, incontinence, overactive bladder, urinary disturbance by bladder inflammation, asthma, dry skin, atopic dermatitis, metastasis and invasion of cancer, corneal ulcer, obesity, insulin resistance, diabetes, or the like.

The compound of the present invention is a compound having utility as a medicament. Herein, utility as a medicament includes the following points: the compound has good metabolic stability; the induction of a drug-metabolizing enzyme is low; the inhibition of a drug-metabolizing enzyme which metabolizes another drug is low; the compound has high oral absorbency; the inhibition of hERG is low; the clearance is low; and/or the half-life is sufficiently long to express the efficacy; or the like.

MODE FOR CARRYING OUT THE INVENTION

Hereinafter, the present invention is described with reference to embodiments. It should be understood that, throughout the present specification, the expression of a singular form includes the concept of its plural form unless specified otherwise. Accordingly, it should be understood that an article in singular form (for example, in the English language, "a," "an," "the," and the like) includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present specification (including definitions) precedes.

Terms used in the present specification are explained below. In the present specification, each term is used in an unequivocal meaning, and has the same meaning when it is used alone or together with other terms.

"Halogen" includes a fluorine atom, chlorine atom, bromine atom and iodine atom. For example, it includes a fluorine atom, chlorine atom and bromine atom.

"Alkyl" includes a C1 to C10 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl, and the like.

An embodiment of "alkyl" is C1-C6 alkyl. Another embodiment is C1-C4 alkyl. When the carbon number is specified in particular, an "alkyl" has carbon in a range of the number.

"Alkenyl" includes a C2 to C10 linear or branched hydrocarbon group having one or more double bond(s) at any position(s). For example, it includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl, and the like.

An embodiment of "alkenyl" is C2-C6 alkenyl. Another embodiment of "alkenyl" is C2-C4 alkenyl.

"Alkynyl" includes a C2 to C10 linear or branched hydrocarbon group having one or more triple bond(s) at any position(s). For example, it includes ethynyl, propynyl, butynyl, pentynyl, hexynyl, heptynyl, octynyl, nonynyl, decynyl, and the like.

An embodiment of "alkynyl" is C2-C6 alkynyl. Another embodiment of "alkynyl" is C2-C4 alkynyl.

"Aromatic carbocyclyl" includes a cyclic aromatic hydrocarbon group which is monocyclic or polycyclic having two or more rings. For example, it includes benzene ring, naphthalene ring, anthracene ring, phenanthrene ring and the like.

A preferred embodiment of "aromatic carbocyclyl" is benzene ring and naphthalene ring.

"Aromatic carbocycle" includes a cyclic aromatic hydrocarbon ring which is monocyclic or polycyclic having two or more rings. For example, it includes benzene ring, naphthalene ring, anthracene ring, phenanthrene ring, and the like.

An embodiment of "aromatic carbocycle" includes benzene ring and naphthalene ring.

"Non-aromatic carbocyclyl" includes a cyclic saturated hydrocarbon group or a cyclic unsaturated non-aromatic hydrocarbon group, which is monocyclic or polycyclic having two or more rings. "Non-aromatic carbocyclyl", which is polycyclic having two or more rings, includes a fused ring group wherein a non-aromatic carbocyclyl, which is monocyclic or polycyclic having two or more rings, is fused with a ring of the above "aromatic carbocyclyl".

In addition, the "non-aromatic carbocyclyl" also includes a group having a bridge or a group to form a spiro ring as follows:

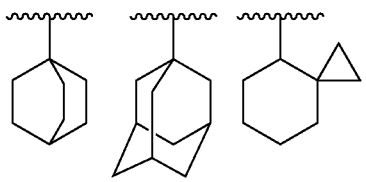

An embodiment of non-aromatic carbocyclyl which is monocyclic is C3 to C16, another embodiment is C3 to C12, and another embodiment is C3 to C8. For example, it includes cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl, and the like.

A non-aromatic carbocyclyl which is polycyclic having two or more rings includes, for example, indanyl, indenyl, acenaphthyl, tetrahydronaphthyl, fluorenyl, and the like.

"Non-aromatic carbocycle" includes a cyclic saturated hydrocarbon ring or a cyclic unsaturated non-aromatic hydrocarbon ring, which is monocyclic or polycyclic having two or more rings. "Non-aromatic carbocycle", which is polycyclic having two or more rings, includes a fused ring wherein the non-aromatic carbocycle, which is monocyclic or polycyclic having two or more rings, is fused with a ring of the above "aromatic carbocycle".

In addition, the "non-aromatic carbocycle" also includes a ring having a bridge or a ring to form a spiro ring as follows:

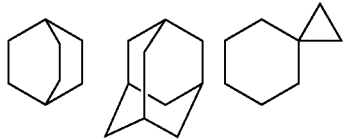

An embodiment of non-aromatic carbocycle which is monocyclic is C3 to C16, another embodiment is C3 to C12, and another embodiment is C4 to C8. For example, it includes cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene, and the like.

A non-aromatic carbocycle which is polycyclic having two or more rings includes, for example, indane, indene, acenaphthalene, tetrahydronaphthalene, fluorene, and the like.

"Aromatic heterocyclyl" includes an aromatic cyclyl, which is monocyclic or polycyclic having two or more rings, containing one or more, same or different of heteroatom(s) selected independently from oxygen atom, sulfur atom and nitrogen atom.

"Aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

An embodiment of aromatic heterocyclyl which is monocyclic is 5- to 8-membered, and another embodiment is 5- or 6-membered. For example, it includes pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl, and the like.

An aromatic heterocyclyl which is bicyclic includes, for example, indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl, and the like.

An aromatic heterocyclyl which is polycyclic having three or more rings includes, for example, carbazolyl, acridinyl, xanthenyl, phenothiazinyl, phenoxathiinyl, phenoxazinyl, dibenzofuryl, and the like.

"Aromatic heterocycle" includes an aromatic ring, which is monocyclic or polycyclic having two or more rings, containing one or more, same or different of heteroatom(s) selected independently from oxygen atom, sulfur atom and nitrogen atom.

"Aromatic heterocycle", which is polycyclic having two or more rings, includes a fused ring wherein an aromatic heterocycle, which is monocyclic or polycyclic having two or more rings, is fused with a ring of the above "aromatic carbocycle".

An embodiment of aromatic heterocycle which is monocyclic is 5- to 8-membered, and another embodiment is 5- or 6-membered. For example, it includes pyrrole, imidazole, pyrazole, pyridine, pyridazine, pyrimidine, pyrazine, triazole, triazine, tetrazole, furane, thiophen, isoxazole, oxazole, oxadiazole, isothiazole, thiazole, thiadiazole, and the like.

An aromatic heterocyclyl which is bicyclic includes, for example, indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, thiazolopyridine, and the like.

An aromatic heterocyclyl which is polycyclic having three or more rings includes, for example, carbazole, acridine, xanthene, phenothiazine, phenoxathiine, phenoxazine, dibenzofuran, and the like.

"Non-aromatic heterocyclyl" includes a non-aromatic heterocyclyl, which is monocyclic or polycyclic having two or more rings, containing one or more, same or different of heteroatom(s) selected independently from oxygen atom, sulfur atom and nitrogen atom.

"Non-aromatic heterocyclyl", which is polycyclic having two or more rings, includes a fused ring group wherein a non-aromatic heterocyclyl, which is monocyclic or polycyclic having two or more rings, is fused with a ring of the above "aromatic carbocyclyl", "non-aromatic carbocyclyl" and/or "aromatic heterocyclyl".

In addition, the "non-aromatic heterocyclyl" also includes a group having a bridge or a group to form a spiro ring as follows:

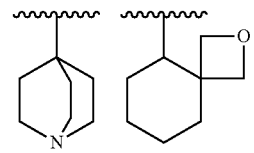

An embodiment of non-aromatic heterocyclyl which is monocyclic is 3- to 8-membered, and another embodiment is 5- or 6-membered. For example, it includes dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl, and the like.

A non-aromatic heterocyclyl which is polycyclic having two or more rings includes, for example, indolinyl, isoindolinyl, chromanyl, isochromanyl, and the like.

"Non-aromatic heterocycle" includes a cyclic non-aromatic ring, which is monocyclic or polycyclic having two or more rings, containing one or more, same or different of heteroatom(s) selected independently from oxygen atom, sulfur atom and nitrogen atom.

"Non-aromatic heterocycle", which is polycyclic having two or more rings, includes a fused ring wherein the non-aromatic heterocycle, which is monocyclic or polycyclic having two or more rings, is fused with a ring of the above "aromatic carbocycle", "non-aromatic carbocycle" and/or "aromatic heterocycle".

In addition, the "non-aromatic heterocycle" also includes a ring having a bridge or a ring to form a spiro ring as follows:

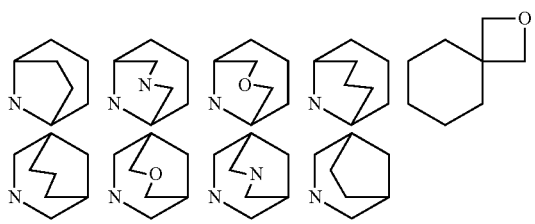

An embodiment of non-aromatic heterocycle which is non-bridged is 3 to 8-membered, another embodiment is 4 to 8-membered, and another embodiment is 5 or 6-membered.

An embodiment of non-aromatic heterocycle which is bridged is 6 to 10-membered, and another embodiment is 8 or 9-membered. Herein, a number of member means a number of all atoms which constitutes a bridged non-aromatic heterocycle.

An embodiment of non-aromatic heterocycle which is monocyclic is 3 to 8-membered, and another embodiment is 5 or 6-membered. For example, dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxoline, oxepane, thiolane, thiine, thiazine, and the like.

A non-aromatic heterocycle which is polycyclic having two or more rings includes, for example, indoline, isoindoline, chromane, isochromane, and the like.

The alkyl part of "aromatic carbocyclylalkyl", "non-aromatic carbocyclylalkyl", "aromatic heterocyclylalkyl", and "non-aromatic heterocyclylalkyl"; "aromatic carbocyclylalkyloxy", "non-aromatic carbocyclylalkyloxy", "aromatic heterocyclylalkyloxy", and "non-aromatic heterocyclylalkyloxy"; "aromatic carbocyclylalkyloxycarbonyl", "non-aromatic carbocyclylalkyloxycarbonyl", "aromatic heterocyclylalkyloxycarbonyl", and "non-aromatic heterocyclylalkyloxycarbonyl"; and "aromatic carbocyclylalkyloxyalkyl", "non-aromatic carbocyclylalkyloxyalkyl", "aromatic heterocyclylalkyloxyalkyl", and "non-aromatic heterocyclylalkyloxyalkyl" is also the same as above "alkyl".

"Aromatic carbocyclylalkyl" means an alkyl substituted with one or more "aromatic carbocyclyl" described above. For example, it includes benzyl, phenethyl, phenylpropyl, benzhydryl, trityl, naphthylmethyl, a group of the formula of

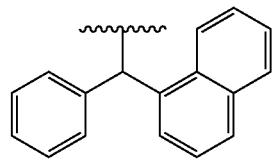 [SMILES: *C(c1ccccc1)c1cccc2ccccc12]

and the like.

An embodiment of "aromatic carbocyclylalkyl" is benzyl, phenethyl or benzhydryl.

"Non-aromatic carbocyclylalkyl" means an alkyl substituted with one or more "non-aromatic carbocyclyl" described above. "Non-aromatic carbocyclylalkyl" also includes "non-aromatic carbocyclylalkyl" wherein the alkyl part is substituted with the above "aromatic carbocyclyl". For example, it includes cyclopropylmethyl, cyclobutylmethyl, cyclopenthylmethyl, cyclohexylmethyl, a group of the formula of

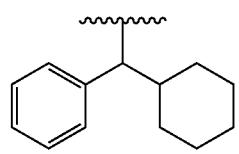 [SMILES: *C(c1ccccc1)C1CCCCC1]

and the like.

"Aromatic heterocyclylalkyl" means an alkyl substituted with one or more "aromatic heterocyclyl" described above. "Aromatic heterocyclylalkyl" also includes "aromatic heterocyclylalkyl" wherein the alkyl part is substituted with the above "aromatic carbocyclyl" and/or "non-aromatic carbocyclyl". For example, it includes pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, groups of the formula of

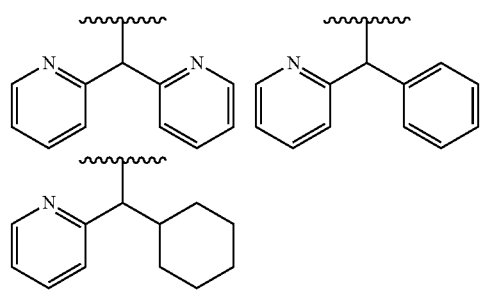

and the like.

"Non-aromatic heterocyclylalkyl" means an alkyl substituted with one or more "non-aromatic heterocyclyl" described above. "Non-aromatic heterocyclylalkyl" also includes "non-aromatic heterocyclylalkyl" wherein the alkyl part is substituted with the above "aromatic carbocyclyl", "non-aromatic carbocyclyl" and/or "aromatic heterocyclyl". For example, it includes tetrahydropyranylmethyl, morpholinylmethyl, morpholinylethyl, piperidinylmethyl, piperazinylmethyl, groups of the formula of

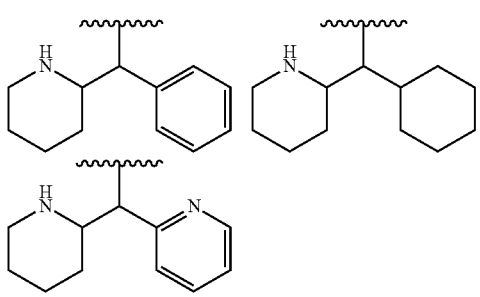

and the like.

The "aromatic carbocycle" part of "aromatic carbocyclyloxy", "aromatic carbocyclylcarbonyl", "aromatic carbocyclyloxycarbonyl", "aromatic carbocyclylsulfanyl", and "aromatic carbocyclylsulfonyl" is the same as above "aromatic carbocyclyl".

"Aromatic carbocyclyloxy" means a group wherein "aromatic carbocycle" is bonded to oxygen atom. For example, it includes phenyloxy, naphthyloxy, and the like.

"Aromatic carbocyclylcarbonyl" means a group wherein "aromatic carbocycle" is bonded to carbonyl group. For example, it includes phenylcarbonyl, naphthylcarbonyl, and the like.

"Aromatic carbocyclyloxycarbonyl" means a group wherein the above "aromatic carbocyclyloxy" is bonded to carbonyl group. For example, it includes phenyloxycarbonyl, naphthyloxycarbonyl, and the like.

"Aromatic carbocyclylsulfanyl" means a group wherein a hydrogen atom bonded to a sulfur atom of sulfanyl group is replaced with "aromatic carbocycle". For example, it includes phenylsulfanyl, naphthylsulfanyl, and the like.

"Aromatic carbocyclylsulfonyl" means a group wherein "aromatic carbocycle" is bonded to sulfonyl group. For example, it includes phenylsulfonyl, naphthylsulfonyl, and the like.

The "non-aromatic carbocycle" part of "non-aromatic carbocyclyloxy", "non-aromatic carbocyclylcarbonyl", "non-aromatic carbocyclyloxycarbonyl", "non-aromatic carbocyclylsulfanyl", and "non-aromatic carbocyclylsulfonyl" is the same as above "non-aromatic carbocyclyl".

"Non-aromatic carbocyclyloxy" means a group wherein "non-aromatic carbocycle" is bonded to oxygen atom. For example, it includes cyclopropyloxy, cyclohexyloxy, cyclohexenyloxy, and the like.

"Non-aromatic carbocyclylcarbonyl" means a group wherein "non-aromatic carbocycle" is bonded to carbonyl group. For example, it includes cyclopropylcarbonyl, cyclohexylcarbonyl, cyclohexenylcarbonyl, and the like.

"Non-aromatic carbocyclyloxycarbonyl" means a group wherein the above "non-aromatic carbocyclyloxy" is bonded to carbonyl group. For example, it includes cyclopropyloxycarbonyl, cyclohexyloxycarbonyl, cyclohexenyloxycarbonyl, and the like.

"Non-aromatic carbocyclylsulfanyl" means a group wherein a hydrogen atom bonded to a sulfur atom of sulfanyl group is replaced with "non-aromatic carbocycle". For example, it includes cyclopropylsulfanyl, cyclohexylsulfanyl, cyclohexenylsulfanyl, and the like.

"Non-aromatic carbocyclylsulfonyl" means a group wherein "non-aromatic carbocycle" is bonded to sulfonyl group. For example, it includes cyclopropylsulfonyl, cyclohexylsulfonyl, cyclohexenylsulfonyl, and the like.

The "aromatic heterocycle" part of "aromatic heterocyclyloxy", "aromatic heterocyclylcarbonyl", "aromatic heterocyclyloxycarbonyl", "aromatic heterocyclylsulfanyl", or "aromatic heterocyclylsulfonyl" is the same as above "aromatic heterocyclyl".

"Aromatic heterocyclyloxy" means a group wherein "aromatic heterocycle" is bonded to oxygen atom. For example, it includes pyridyloxy, oxazolyloxy, and the like.

"Aromatic heterocyclylcarbonyl" means a group wherein "aromatic heterocycle" is bonded to carbonyl group. For example, it includes pyridylcarbonyl, oxazolylcarbonyl, and the like.

"Aromatic heterocyclyloxycarbonyl" means a group wherein the above "aromatic heterocyclyloxy" is bonded to carbonyl group. For example, it includes pyridyloxycarbonyl, oxazolyloxycarbonyl, and the like.

"Aromatic heterocyclylsulfanyl" means a group wherein a hydrogen atom bonded to a sulfur atom of sulfanyl group is replaced with "aromatic heterocycle". For example, it includes pyridylsulfanyl, oxazolylsulfanyl, and the like.

"Aromatic heterocyclylsulfonyl" means a group wherein "aromatic heterocycle" is bonded to sulfonyl group. For example, it includes pyridylsulfonyl, oxazolylsulfonyl, and the like.

The "non-aromatic heterocycle" part of "non-aromatic heterocyclyloxy", "non-aromatic heterocyclylcarbonyl", "non-aromatic heterocyclyloxycarbonyl", "non-aromatic heterocyclylsulfanyl", or "non-aromatic heterocyclylsulfonyl" is the same as above "non-aromatic heterocyclyl". The "non-aromatic heterocycle" part of "$R^A$ and $R^B$ may be taken together with the nitrogen atom which is attached to them to form substituted or unsubstituted non-aromatic heterocycle" is the same as above "non-aromatic heterocyclyl".

"Non-aromatic heterocyclyloxy" means a group wherein "non-aromatic heterocycle" is bonded to oxygen atom. For example, it includes piperidinyloxy, tetrahydrofuryloxy, and the like.

"Non-aromatic heterocyclylcarbonyl" means a group wherein "non-aromatic heterocycle" is bonded to carbonyl group. For example, it includes piperidinylcarbonyl, tetrahydrofurylcarbonyl, and the like.

"Non-aromatic heterocyclyloxycarbonyl" means a group wherein the above "non-aromatic heterocyclyloxy" is bonded to carbonyl group. For example, it includes piperidinyloxycarbonyl, tetrahydrofuryloxycarbonyl, and the like.

"Non-aromatic heterocyclylsulfanyl" means a group wherein a hydrogen atom bonded to a sulfur atom of sulfanyl group is replaced with "non-aromatic heterocycle". For example, it includes piperidinylsulfanyl, tetrahydrofurylsulfanyl, and the like.

"Non-aromatic heterocyclylsulfonyl" means a group wherein "non-aromatic heterocycle" is bonded to sulfonyl group. For example, it includes piperidinylsulfonyl, tetrahydrofurylsulfonyl, and the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted alkylsulfonyl" in $R^3$, $R^5$, $R^6$ and $R^7$ include the following substituents. A carbon atom at any positions may be bonded to one or more group(s) selected from the following substituents.

Substituents: halogen, hydroxy, carboxy, amino, imino, formyl, sulfanyl, sulfino, sulfo, thioformyl, thiocarboxy, dithiocarboxy, thiocarbamoyl, cyano, nitro, azido, silyloxy optionally substituted with the substituent group A, alkylcarbonyloxy optionally substituted with the substituent group E, hydrazino optionally substituted with the substituent group A, ureido optionally substituted with the substituent group A, amidino optionally substituted with the substituent group A, guanidino optionally substituted with the substituent group A, amino optionally substituted with the substituent group B, imino optionally substituted with the substituent group D, alkyloxy, alkenyloxy, alkynyloxy, haloalkyloxy, haloalkenyloxy, haloalkynyloxy, alkylcarbonyl optionally substituted with the substituent group E, alkenylcarbonyl optionally substituted with the substituent group E, alkynylcarbonyl optionally substituted with the substituent group E, alkylsulfonyl, alkenylsulfonyl, alkynylsulfonyl, haloalkylsulfonyl, haloalkenylsulfonyl, haloalkynylsulfonyl, alkenylcarbonyloxy, alkynylcarbonyloxy, alkyloxycarbonyl, alkyloxycarbonyl, alkenyloxycarbonyl, alkynyloxycarbonyl, alkylsulfanyl, alkenylsulfanyl, alkynylsulfanyl, haloalkylsulfanyl, halo alkenylsulfanyl, halo alkynylsulfanyl, carbamoyl optionally substituted with the substituent group F, sulfamoyl optionally substituted with the substituent group F, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocyclyloxy optionally substituted with the substituent group C, non-aromatic carbocyclyloxy optionally substituted with the substituent group C, aromatic heterocyclyloxy optionally substituted with the substituent group C, non-aromatic heterocyclyloxy optionally substituted with the substituent group C, aromatic carbocyclylcarbonyl optionally substituted with the substituent group C, non-aromatic carbocyclylcarbonyl optionally substituted with the substituent group C, aromatic heterocyclylcarbonyl optionally substituted with the substituent group C, non-aromatic heterocyclylcarbonyl optionally substituted with the substituent group C, aromatic carbocyclyloxycarbonyl optionally substituted with the substituent group C, non-aromatic carbocyclyloxycarbonyl optionally substituted with the substituent group C, aromatic heterocyclyloxycarbonyl optionally substituted with the substituent group C, non-aromatic heterocyclyloxycarbonyl optionally substituted with the substituent group C, aromatic carbocyclylalkyloxy optionally substituted with the substituent group C, non-aromatic carbocyclylalkyloxy optionally substituted with the substituent group C, aromatic heterocyclylalkyloxy optionally substituted with the substituent group C, non-aromatic heterocyclylalkyloxy optionally substituted with the substituent group C, aromatic carbocyclylalkyloxycarbonyl optionally substituted with the substituent group C, non-aromatic carbocyclylalkyloxycarbonyl optionally substituted with the substituent group C, aromatic heterocyclylalkyloxycarbonyl optionally substituted with the substituent group C, non-aromatic heterocyclylalkyloxycarbonyl optionally substituted with the substituent group C, aromatic carbocyclylsulfanyl optionally substituted with the substituent group C, non-aromatic carbocyclylsulfanyl optionally substituted with the substituent group C, aromatic heterocyclylsulfanyl optionally substituted with the substituent group C, non-aromatic heterocyclylsulfanyl optionally substituted with the substituent group C, aromatic carbocyclylsulfonyl optionally substituted with the substituent group C, non-aromatic carbocyclylsulfonyl optionally substituted with the substituent group C, aromatic heterocyclylsulfonyl optionally substituted with the substituent group C, and non-aromatic heterocyclylsulfonyl optionally substituted with the substituent group C.

The substituent group A are alkyl and haloalkyl.

The substituent group B are hydroxy, cyano, alkyl, haloalkyl, alkylcarbonyl, haloalkylcarbonyl, alkylsulfonyl, haloalkylsulfonyl, alkyloxycarbonyl, carbamoyl optionally substituted with the substituent group A, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocyclylalkyl optionally substituted with the substituent group C, non-aromatic carbocyclylalkyl optionally substituted with the substituent group C, aromatic heterocyclylalkyl optionally substituted with the substituent group C, non-aromatic heterocyclylalkyl optionally substituted with the substituent group C, aromatic carbocyclylcarbonyl optionally substituted with the substituent group C, non-aromatic carbocyclylcarbonyl optionally substituted with the substituent group C, aromatic heterocyclylcarbonyl optionally substituted with the substituent group C, non-aromatic heterocyclylcarbonyl optionally substituted with the substituent group C, aromatic carbocyclyloxycarbonyl optionally substituted with the substituent group C, non-aromatic carbocyclyloxycarbonyl optionally substituted with the substituent group C, aromatic heterocyclyloxycarbonyl optionally substituted with the substituent group C, non-aromatic heterocyclyloxycarbonyl optionally substituted with the substituent group C, aromatic carbocyclylalkykoxycarbonyl optionally substituted with the substituent group C, non-aromatic carbocyclylalkyloxycarbonyl optionally substituted with the substituent group C, aromatic heterocyclylalkyloxycarbonyl optionally substituted with the substituent group C, non-aromatic heterocyclylalkyloxycarbonyl optionally substituted with the substituent group C, aromatic carbocyclylaminocarbonyl optionally substituted with the substituent group C, non-aromatic carbocyclylaminocarbonyl optionally substituted with the substituent group C, aromatic heterocyclylaminocarbonyl optionally substituted with the substituent group C, and non-aromatic heterocyclylaminocarbonyl optionally substituted with the substituent group C.

The substituent group C are halogen; hydroxy; cyano; carboxy; alkyl optionally substituted with halogen, hydroxy or cyano; alkyloxy optionally substituted with halogen, hydroxy or cyano; alkylcarbonyl optionally substituted with halogen, hydroxy or cyano; alkyloxycarbonyl optionally substituted with halogen, hydroxy or cyano; alkylcarbonyloxy optionally substituted with halogen, hydroxy or cyano; amino optionally substituted with alkyl or haloalkyl; alkylsulfonyl optionally substituted with halogen, hydroxy or cyano; alkylsulfanyl optionally substituted with halogen, hydroxy or cyano; alkylcarbonylamino optionally substituted with halogen, hydroxy or cyano; alkylcarbamoyl optionally substituted with halogen, hydroxy or cyano; alkylsulfonylamino optionally substituted with halogen, hydroxy or cyano; alkylsulfamoyl optionally substituted with halogen, hydroxy or cyano; non-aromatic carbocyclyl and non-aromatic heterocyclyl.

The substituent group D are hydroxy, alkyl, alkenyl, alkynyl, haloalkyl, haloalkenyl, haloalkynyl, alkyloxy, alkenyloxy, alkynyloxy, haloalkyloxy, haloalkenyloxy, haloalkynyloxy, alkyloxycarbonyl, alkenylcarbonyl, alkynylcarbonyl, haloalkylcarbonyl, haloalkenylcarbonyl, haloalkynylcarbonyl, amino, alkylamino, haloalkylamino, aromatic carbocyclyl optionally substituted with substituent group C, non-aromatic carbocyclyl optionally substituted with substituent group C, aromatic heterocyclyl optionally substituted with substituent group C, and non-aromatic heterocyclyl optionally substituted with substituent group C.

The substituent group E are halogen, hydroxy, cyano, alkyloxy, haloalkyloxy, hydroxyalkyloxy, alkylcarbonyloxy, amino optionally substituted with substituent group B, aromatic carbocyclyl optionally substituted with substituent group C, non-aromatic carbocyclyl optionally substituted with substituent group C, aromatic heterocyclyl optionally substituted with substituent group C, non-aromatic heterocyclyl optionally substituted with substituent group C, aromatic carbocyclyloxy optionally substituted with substituent group C, non-aromatic carbocyclyloxy optionally substituted with substituent group C, aromatic heterocyclyloxy optionally substituted with substituent group C, non-aromatic heterocyclyloxy optionally substituted with substituent group C, aromatic carbocyclylsulfonyl optionally substituted with substituent group C, non-aromatic carbocyclylsulfonyl optionally substituted with substituent group C, aromatic heterocyclylsulfonyl optionally substituted with substituent group C, non-aromatic heterocyclylsulfonyl optionally substituted with substituent group C, aromatic carbocyclylsulfanyl optionally substituted with substituent group C, non-aromatic carbocyclylsulfanyl optionally substituted with substituent group C, aromatic heterocyclylsulfanyl optionally substituted with substituent group C, non-aromatic heterocyclylsulfanyl optionally substituted with substituent group C.

The substituent group F are hydroxy, cyano, amino, alkylamino, alkyl, haloalkyl, hydroxyalkyl, alkylcarbonyl, alkylcarbonylamino, alkylsulfonyl, aromatic carbocyclyl optionally substituted with substituent group C, non-aromatic carbocyclyl optionally substituted with substituent group C, aromatic heterocyclyl optionally substituted with substituent group C, non-aromatic heterocyclyl optionally substituted with substituent group C, aromatic carbocyclylcarbonyl optionally substituted with substituent group C, non-aromatic carbocyclylcarbonyl optionally substituted with substituent group C, aromatic heterocyclylcarbonyl optionally substituted with substituent group C, non-aromatic heterocyclylcarbonyl optionally substituted with substituent group C, aromatic carbocyclylalkyl optionally substituted with substituent group C, non-aromatic carbocyclylalkyl optionally substituted with substituent group C, aromatic heterocyclylalkyl optionally substituted with substituent group C, and non-aromatic heterocyclylalkyl optionally substituted with substituent group C.

The substituent group G are hydroxy, cyano, amino, alkylamino, haloalkylamino, alkylcarbonylamino, haloalkylcarbonylamino, alkyl, haloalkyl, hydroxyalkyl, cyanoalkyl, alkylcarbonyl, haloalkylcarbonyl, alkylsulfonyl, aromatic carbocyclyl optionally substituted with substituent group C, non-aromatic carbocyclyl optionally substituted with substituent group C, aromatic heterocyclyl optionally substituted with substituent group C, non-aromatic heterocyclyl optionally substituted with substituent group C, aromatic carbocyclylalkyl optionally substituted with substituent group C, non-aromatic carbocyclylalkyl optionally substituted with substituent group C, aromatic heterocyclylalkyl optionally substituted with substituent group C, and non-aromatic heterocyclylalkyl optionally substituted with substituent group C.

The substituent group H are halogen, hydroxy, carboxy, carbamoyl, amino, imino, sulfo, cyano, nitro, hydrazino, hydrazide, ureido, guanidino, amidino optionally substituted with hydroxy, alkyloxy, haloalkyloxy, alkylamino, haloalkylamino, alkyloxycarbonyl, haloalkyloxycarbonyl, alkylcarbonylamino, and haloalkylcarbonylamino.

The substituents on the ring of "aromatic carbocycle", "non-aromatic carbocycle", "aromatic heterocycle" or "non-aromatic heterocycle" of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl" in $R^3$, $R^5$, $R^6$ and $R^7$ include the following substituents. An atom at any position(s) on the ring may be bonded to one or more group(s) selected from the following substituents.

Substituents: halogen, hydroxy, carboxy, amino, imino, formyl, sulfanyl, sulfino, sulfo, thioformyl, thiocarboxy, dithiocarboxy, thiocarbamoyl, cyano, nitro, azido, hydrazino optionally substituted with substituent group A, ureide optionally substituted with substituent group A, amidino optionally substituted with substituent group A, guanidino optionally substituted with substituent group A, amino optionally substituted with substituent group B, imino optionally substituted with substituent group D, alkyl optionally substituted with substituent group H, alkenyl optionally substituted with substituent group H, alkynyl optionally substituted with substituent group H, alkyloxy optionally substituted with substituent group H, alkenyloxy optionally substituted with substituent group H, alkynyloxy optionally substituted with substituent group H, alkylcarbonyl optionally substituted with substituent group E, alkenylcarbonyl optionally substituted with substituent group E, alkynylcarbonyl optionally substituted with substituent group E, alkylsulfonyl, alkenylsulfonyl, alkynylsulfonyl, haloalkylsulfonyl, haloalkenylsulfonyl, haloalkynylsulfonyl, alkylcarbonyloxy optionally substituted with substituent group E, alkenylcarbonyloxy optionally substituted with substituent group E, alkynylcarbonyloxy optionally substituted with substituent group E, alkyloxycarbonyl optionally substituted with substituent group E, alkenyloxycarbonyl optionally substituted with substituent group E, alkynyloxycarbonyl optionally substituted with substituent group E, alkyloxycarbonylalkyl, alkylsulfanyl, alkenylsulfanyl, alkynylsulfanyl, haloalkylsulfanyl, haloalkenylsulfanyl, haloalkynylsulfanyl, carbamoyl optionally substituted with substituent group F, aminocarbonyloxy optionally substituted with substituent group G, sulfamoyl optionally substituted with substituent group F, aromatic carbocyclyl optionally substituted with substituent group C, non-aromatic carbocyclyl optionally substituted with substituent group C, aromatic heterocyclyl optionally substituted with substituent group C, non-aromatic heterocyclyl optionally substituted with substituent group C, aromatic carbocyclyloxy optionally substituted with substituent group C, non-aromatic carbocyclyloxy optionally substituted with substituent group C, aromatic heterocyclyloxy optionally substituted with substituent group C, non-aromatic heterocyclyloxy optionally substituted with substituent group C, aromatic carbocyclylcarbonyl optionally substituted with substituent group C, non-aromatic carbocyclylcarbonyl optionally substituted with substituent group C, aromatic heterocyclylcarbonyl optionally substituted with substituent group C, non-aromatic heterocyclylcarbonyl optionally substituted with substituent group C, aromatic carbocyclyloxycarbonyl optionally substituted with substituent group C, non-aromatic carbocyclyloxycarbonyl optionally substituted with substituent group C, aromatic heterocyclyloxycarbonyl optionally substituted with substituent group C, non-aromatic heterocyclyloxycarbonyl optionally substituted with substituent group C, aromatic carbocyclylalkyl optionally substituted with substituent group C, non-aromatic carbocyclylalkyl optionally substituted with substituent group C, aromatic heterocyclylalkyl optionally substituted with substituent group C, non-aromatic heterocyclylalkyl optionally substituted with substituent group C, aromatic carbocyclylalkenyl optionally substituted with substituent group C, non-aromatic carbocyclylalkenyl optionally substituted with substituent group C, aromatic heterocyclylalkenyl optionally substituted with substituent group C, non-aromatic heterocyclylalkenyl optionally substituted with substituent group C, aromatic carbocyclylalkyloxy optionally substituted with substituent group C, non-aromatic carbocyclylalkyloxy, aromatic heterocyclylalkyloxy optionally substituted with substituent group C, non-aromatic heterocyclylalkyloxy optionally substituted with substituent group C, aromatic carbocyclylalkyloxycarbonyl optionally substituted with substituent group C, non-aromatic carbocyclylalkyloxycarbonyl optionally substituted with substituent group C, aromatic heterocyclylalkyloxycarbonyl optionally substituted with substituent group C, non-aromatic heterocyclylalkyloxycarbonyl optionally substituted with substituent group C, aromatic carbocyclylalkyloxyalkyl optionally substituted with substituent group C, non-aromatic carbocyclylalkyloxyalkyl optionally substituted with substituent group C, aromatic heterocyclylalkyloxyalkyl optionally substituted with substituent group C, non-aromatic heterocyclylalkyloxyalkyl optionally substituted with substituent group C, aromatic carbocyclylsulfanyl optionally substituted with substituent group C, non-aromatic carbocyclylsulfanyl optionally substituted with substituent group C, aromatic heterocyclylsulfanyl optionally substituted with substituent group C, non-aromatic heterocyclylsulfanyl optionally substituted with substituent group C, non-aromatic carbocyclylsulfonyl optionally substituted with substituent group C, aromatic carbocyclylsulfonyl optionally substituted with substituent group C, aromatic heterocyclylsulfonyl optionally substituted with substituent group C, and non-aromatic heterocyclylsulfonyl optionally substituted with substituent group C.

The substituents of "substituted or unsubstituted alkyl", "substituted or unsubstituted alkenyl", or "substituted or unsubstituted alkynyl" in $R^8$ include the following substituents H. A carbon atom at any positions may be bonded to one or more group(s) selected from the following substituents H.

The substituents of "substituted or unsubstituted alkyl", "substituted or unsubstituted alkenyl", or "substituted or unsubstituted alkynyl" in $R^{8a}$ include the following substituents H. A carbon atom at any positions may be bonded to one or more group(s) selected from the following substituents H.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on the same carbon atom are substituted as below.

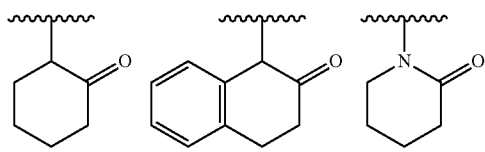

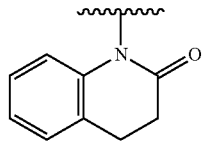

The non-aromatic carbocycle or non-aromatic heterocycle part of the above "substituted or unsubstituted non-aromatic carbocyclyloxy", "substituted or unsubstituted non-aromatic heterocyclyloxy", "substituted or unsubstituted non-aromatic carbocyclylcarbonyl", "substituted or unsubstituted non-aromatic heterocyclylcarbonyl", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfanyl", "substituted or unsubstituted non-aromatic heterocyclylsulfanyl", "substituted or unsubstituted non-aromatic carbocyclylsulfonyl", and "substituted or unsubstituted non-aromatic heterocyclylsulfonyl" may be substituted with "oxo" as above.

"Substituted or unsubstituted amino" in $R^3$, $R^5$, $R^6$ and $R^7$ includes amino optionally substituted with the above substituent group B at one or two position(s).

An embodiment of "substituted or unsubstituted amino" is amino, methylamino, dimethylamino, ethylamino, diethylamino, ethylmethylamino, cyclopropylamino, cyclohexylamino, benzylamino, acetylamino, benzoylamino, tert-butyloxycarbonylamino, methylsulfonylamino, tetrahydropyranylamino, tetrahydrofuranylamino, morpholinoamino, morpholinylamino, piperidinylamino, piperazinylamino and the like. Another embodiment of "substituted or unsubstituted amino" is amino, methylamino, dimethylamino, ethylmethylamino, diethylamino, acetylamino, methylsulfonylamino, tetrahydropyranylamino, tetrahydrofuranylamino, morpholinoamino, piperidinylamino and the like.

An embodiment of "substituted or unsubstituted amidino" and "substituted or unsubstituted guanidino" include amidino and guanidine optionally substituted with the above substituent group B at one or two position(s).

"Substituted or unsubstituted carbamoyl" in $R^3$, $R^5$, $R^6$ and $R^7$ includes aminocarbonyl optionally substituted with the above substituent group F at one or two position(s).

An embodiment of "substituted or unsubstituted carbamoyl" is carbamoyl, N-methylcarbamoyl, N,N-dimethylcarbamoyl, N-ethyl-N-methylcarbamoyl, N,N-diethylcarbamoyl, N-n-propylaminocarbamoyl, N-isopropylcarbamoyl, N-morpholinocarbamoyl, N-tetrahydrofuranylcarbamoyl, N-piperidylcarbamoyl, N-tetrahydropyranylcarbamoyl, N-benzylcarbamoyl, N-acetylcarbamoyl, N-methylsulfonylcarbamoyl, N-(2,2,2-trifluoroethyl)pcarbamoyl, N-(2-hydroxy-1-methylethyl)carbamoyl and the like. Another embodiment of "substituted or unsubstituted carbamoyl" is carbamoyl, N-methylcarbamoyl, N,N-dimethylcarbamoyl, N-n-propylaminocarbamoyl, N-isopropylcarbamoyl, N-morpholinocarbamoyl, N-tetrahydrofuranylcarbamoyl, N-piperidylcarbamoyl, N-tetrahydropyranylcarbamoyl, N-methylsulfonylcarbamoyl, N-(2,2,2-trifluoroethyl)carbamoyl, N-(2-hydroxy-1-methylethyl)carbamoyl, N-methyl-N-methyloxycarbamoyl and the like.

"Substituted or unsubstituted sulfamoyl" in $R^7$ includes aminosulfonyl optionally substituted with the above substituent group F.

An embodiment of "substituted or unsubstituted sulfamoyl" is sulfamoyl, N-methylsulfamoyl, N,N-dimethylsulfamoyl, N-ethyl-N-methylsulfamoyl, N,N-diethylsulfamoyl, N-n-propylaminosulfamoyl, N-isopropylsulfamoyl, N-morpholinosulfamoyl, N-tetrahydrofuranylsulfamoyl, N-piperidylsulfamoyl, N-tetrahydropyranylsulfamoyl, N-benzylsulfamoyl, N-acetylsulfamoyl, N-methylsulfonylsulfamoyl and the like. Another embodiment of "substituted or unsubstituted sulfamoyl" is sulfamoyl, N-methylsulfamoyl, N,N-dimethylsulfamoyl, N-n-propylaminosulfamoyl, N-isopropylsulfamoyl, N-morpholinosulfamoyl, N-tetrahydrofuranylsulfamoyl, N-piperidylsulfamoyl, N-tetrahydropyranylsulfamoyl, N-methylsulfonylsulfamoyl and the like.

The substituent of "substituted or unsubstituted alkyl" in $R^5$ includes one or more group(s) selected from, for example, cyano, non-aromatic heterocyclyl, halogen, carbamoyloxy, alkyloxy, hydroxy, alkylcarbonylamino.

The substituent of "substituted or unsubstituted alkyl" in $R^5$ includes one or more group(s) selected from, for example, hydroxyl, halogen.

The substituent of "substituted or unsubstituted alkyl" in $R^6$ includes one or more group(s) selected from, for example, hydroxy, halogen, alkyloxy.

The substituent of "substituted or unsubstituted alkyl" in $R^6$ includes one or more group(s) selected from, for example, hydroxy, halogen.

The substituent of "substituted or unsubstituted alkyl" in $R^7$, for example,
hydroxy;
halogen;
substituted with halogen, alkylsulfonyl, cyano or the like, or unsubstituted aromatic carocyclylamino;
substituted with haloalkyl or the like, or unsubstituted non-aromatic carocyclylamino;
substituted with halogen, cyano or the like, or unsubstituted aromatic heterocyclylamino;
substituted with halogen, hydroxyl, cyano, alkyloxy, non-aromatic carbocyclyl, non-aromatic heterocyclyl or the like, or unsubstituted alkylamino;
substituted with halogen or the like, or unsubstituted aromatic carocyclyloxy;
substituted with haloalkyl, oxo, halogen, hydroxy or the like, or unsubstituted non-aromatic heteroclyl;
substituted with halogen, non-aromatic carbocyclyl or the like, or unsubstituted alkyloxy;
substituted or unsubstituted alkylcarbonylamino;
substituted with nitro or the like, or unsubstituted aromatic carocyclylsulfonylamino; and
substituted with halogen or the like, or unsubstituted aromatic carocyclylsulfonyl or the like are exemplified. It may be optionally substituted with one or more group(s) selected from the above substituents.

The substituent of "substituted or unsubstituted amino" in $R^7$, for example,
substituted with halogen or the like, or unsubstituted aromatic carocyclylsulfonyl;
substituted with halogen or the like, or unsubstituted aromatic carocyclylcarbonyl; and
substituted or unsubstituted alkyloxycarbonyl or the like are exemplified. It may be optionally substituted with one or more group(s) selected from the above substituents.

The substituent of "substituted or unsubstituted alkenyl" in $R^7$, for example, hydroxyl; halogen; substituted with halogen or the like, or unsubstituted aromatic carocyclyl or the like are exemplified. It may be optionally substituted with one or more group(s) selected from the above substituents.

The substituent of "substituted or unsubstituted alkyloxy" in $R^7$, for example, halogen; substituted with halogen or the like, or unsubstituted aromatic carocyclyl or the like are exemplified. It may be optionally substituted with one or more group(s) selected from the above substituents.

The substituent of "substituted or unsubstituted alkylcarbonyl" and "substituted or unsubstituted alkylsulfonyl" in $R^7$, for example, substituted with halogen or the like, or unsubstituted aromatic carocyclyl or the like are exemplified. It may be optionally substituted with one or more group(s) selected from the above substituents.

The substituent of "substituted or unsubstituted carbamoyl" in $R^7$, for example, alkyl; alkyloxy;
substituted with alkyloxycarbonyl, haloalkyl, non-aromatic carbocyclylcarbonyl, alkylcarbonyl, haloalkylcarbonyl, alkylsulfonyl, alkylcarbonyloxyalkylcarbonyl, hydroxyalkylcarbonyl, alkyloxycarbonyl, alkyl or the like, or unsubstituted non-aromatic heterocyclyl;
substituted with halogen, haloalkyl, cyano, substituted with halogen or the like, or unsubstituted aromatic carbocyclyl or the like, or unsubstituted aromatic heterocyclyl;
substituted with halogen or the like, or unsubstituted aromatic heterocyclyl;
substituted with halogen, cyano, alkyl, haloalkyl, aromatic carbocyclyloxy, alkyloxy, haloalkyloxy, alkylamino or the like, or unsubstituted aromatic carbocyclyl; and
substituted with cyano, substituted with halogen or the like, or unsubstituted aromatic carbocyclyl, hydroxyl, halogen, alkyloxycarbonyl, non-aromatic heterocyclyl or the like, or unsubstituted alkyl or the like are exemplified. It may be optionally substituted with one or more group(s) selected from the above substituents.

The substituent of "substituted or unsubstituted sulfamoyl" in $R^7$, for example, substituted with halogen or the like, or unsubstituted aromatic carocyclyl or the like are exemplified. It may be optionally substituted with one or more group(s) selected from the above substituents.

The substituent of "substituted or unsubstituted non-aromatic heterocyclylcarbonyl" in $R^7$, for example,
oxo;
cyano;
hydroxy;
hydroxyimino;
carboxy;
substituted with alkylcarbonyl, hydroxyalkylcarbonyl, haloalkylcarbonyl, non-aromatic carbocyclylcarbonyl, alkyloxyalkylcarbonyl, oxo, haloalkyloxycaronyl, alkyl or the like, or unsubstituted non-aromatic carocyclyl;
substituted with alkyl, substituted with halogen, non-aromatic carbocyclyl, hydroxy, alkylamino, alkyloxy, substituted with alkyl or the like, or unsubstituted aromatic heterocyclyl, haloalkylamino, alkylcarbonylamino or the like, or unsubstituted
alkylcarbonyl;
alkylsulfonyl;
substituted with alkyl, alkyloxycarbonyl, haloalkyl, alkylsulfonyl, substituted with halogen, aromatic carbocyclyl or the like, or unsubstituted alkyloxycarbonyl,
substituted with haloalkyl or the like, or unsubstituted aromatic heterocyclyl, or unsubstituted amino;
substituted with carbamoyl, non-aromatic heterocyclylcarbonyl, hydroxy, alkyloxy, halogen, non-aromatic carbocyclyl or the like, or unsubstituted alkyloxyimino;
substituted with hydroxy or the like, or unsubstituted alkylcarbonyl;
substituted or unsubstituted non-aromatic carbocyclyloxyimino;

substituted with hydroxy, carboxy, substituted with alkylcarbonyl or the like, or unsubstituted amino, alkyloxycarbonyl, alkylamino, carbamoyl or the like, or unsubstituted alkyloxy;
substituted with hydroxy, halogen, alkyloxycarbonylamino, alkylcarbonylamino, cyano, alkyloxy, substituted with alkyl or the like, or unsubstituted carbamoyl, alkyloxycarbonyl or the like, or unsubstituted alkyl;
substituted with hydroxyalkyl non-aromatic carbocyclylalkyl, haloalkylamino, alkylcarbonylamino, amino, alkyloxycarbonylamino, halogen or the like, or unsubstituted alkyloxycarbonyl;
substituted with alkyloxycarbonyl, alkylcarbonyl or the like, or unsubstituted non-aromatic heterocyclyloxycarbonyl;
substituted with hydroxy, substituted with haloalkyl or the like, or unsubstituted aromatic heterocyclyl, substituted with alkyl, alkyloxy or the like, or unsubstituted carbamoyl, or unsubstituted non-aromatic heterocyclylcarbonyl or the like are exemplified.

The substituent of "substituted or unsubstituted non-aromatic carbocyclylcarbonyl" and "substituted or unsubstituted non-aromatic heterocyclylcarbonyl" in $R^7$, for example,
substituted with halogen, hydroxy, carboxy, hydrazide, cyano, carbamoyl, substituted with hydroxy or the like, or unsubstituted amidino, alkyloxycarbonyl or the like, or unsubstituted alkyloxy;
substituted with alkyl, alkyloxy, haloalkyl, hydroxyalkyl, cyanoalkyl, alkylcarbonylamino, substituted with hydroxy or the like, or unsubstituted non-aromatic carbocyclyl or the like, or unsubstituted aminocarbonyloxy;
substituted with alkyl, haloalkyl, alkyloxy, non-aromatic carbocyclyl, hydroxyalkyl, amino, alkylcarbonyl, alkyloxycarbonyl, haloalkylcarbamoyl, substituted with halogen or the like, or unsubstituted non-aromatic carbocyclylcarbamoyl or the like, or unsubstituted aromatic heterocyclyloxy;
substituted with alkyl, haloalkyl, alkyloxy or the like, or unsubstituted aromatic heterocyclylalkyloxy;
substituted with hydroxy or the like, or unsubstituted non-aromatic heterocyclylcarbonyloxy or the like are exemplified. It may be optionally substituted with one or more group(s) selected from the above substituents.

The substituent of "substituted or unsubstituted alkyl" in $R^8$, for example, hydroxy, carboxy, hydrazide cyano, carbamoyl, substituted with hydroxy or the like, or unsubstituted amidino, alkyloxycarbonyl or the like are exemplified. It may be optionally substituted with one or more group(s) selected from the above substituents.

The substituent of "substituted or unsubstituted aromatic heterocyclyl" and "substituted or unsubstituted aromatic carbocyclyl" in $R^8$, for example, alkyl, haloalkyl, alkyloxy, non-aromatic carbocyclyl or the like are exemplified. It may be optionally substituted with one or more group(s) selected from the above substituents.

Embodiments of the present invention are exemplified below.

A compound represented by formula (I);

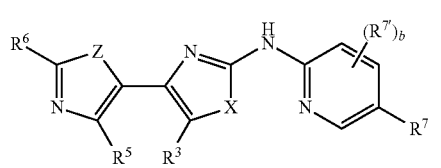

(I)

wherein each symbol is the same as above,
or a pharmaceutically acceptable salt thereof.

Embodiments of $R^5$, $R^6$, $R^7$, $R^{7'}$, X, Z and "b" are exemplified below. An embodiment of a compound represented by formula (I) includes the compound indicated by all possible combination of the following each substituent.

As $R^5$, substituted or unsubstituted alkyl are exemplified; hereinafter referred to as A-1.

$R^5$ includes, for example, substituted or unsubstituted methyl; hereinafter referred to as A-2.

$R^5$ includes, for example, methyl optionally substituted with one or more group(s) selected from cyano, non-aromatic heterocyclyl, halogen, carbamoyloxy, alkyloxy, hydroxy and alkylcarbonylamino; hereinafter referred to as A-3.

$R^5$ includes, for example, unsubstituted methyl; hereinafter referred to as A-4.

As $R^6$, substituted or unsubstituted alkyl or substituted or unsubstituted carbamoyl are exemplified; hereinafter referred to as B-1.

$R^6$ includes, for example, substituted or unsubstituted methyl; hereinafter referred to as B-2.

$R^6$ includes, for example, alkyl optionally substituted with one or more group(s) selected from hydroxy, halogen and alkyloxy, hereinafter referred to as B-3.

$R^6$ includes, for example, C1-C2 alkyl optionally substituted with one or more group(s) selected from hydroxy, halogen and alkyloxy, hereinafter referred to as B-4.

$R^6$ includes, for example, unsubstituted methyl; hereinafter referred to as B-5.

As $R^7$, cyano, substituted or unsubstituted amino, substituted alkyl, substituted or unsubstituted alkenyl, substituted or unsubstituted alkyloxy, substituted or unsubstituted alkylcarbonyl, substituted or unsubstituted alkylsulfonyl, substituted or unsubstituted carbamoyl, substituted or unsubstituted sulfamoyl or substituted or unsubstituted non-aromatic heterocyclylcarbonyl are exemplified; hereinafter referred to as C-1.

$R^7$ includes, for example, substituted or unsubstituted alkyl, substituted or unsubstituted carbamoyl or substituted or unsubstituted non-aromatic heterocyclylcarbonyl; hereinafter referred to as C-2.

$R^7$ includes, for example,
unsubstituted alkyl;
alkyl substituted with hydroxyl;
alkyl substituted with halogen;
alkyl substituted with non-aromatic heterocyclylamino; or
alkyl substituted with heterocyclylamino substituted with halogen, alkylsulfonyl or cyano;
alkyl substituted with unsubstituted non-aromatic carbocyclylamino; or
alkyl substituted with non-aromatic carbocyclylamino substituted with haloalkyl;
alkyl substituted with non-aromatic heterocyclylamino; or
alkyl substituted with heterocyclylamino substituted with halogen or cyano;
alkyl substituted with unsubstituted alkylamino; or
alkyl substituted with alkylamino substituted with halogen, hydroxyl, cyano,
alkyloxy, non-aromatic carbocyclyl or non-aromatic heterocyclyl;
alkyl substituted with unsubstituted non-aromatic carbocyclyloxy; or
alkyl substituted with aromatic carbocyclyloxy substituted with halogen; or
alkyl substituted with unsubstituted non-aromatic heterocyclyl; or
alkyl substituted with non-aromatic heterocyclyl substituted with haloalkyl, oxo, halogen or hydroxy;

alkyl substituted with unsubstituted alkyloxy; or
alkyl substituted with alkyloxy substituted with halogen or non-aromatic carbocyclyl;
alkyl substituted with substituted or unsubstituted alkylcarbonylamino;
alkyl substituted with unsubstituted aromatic carbocyclyl sulfonylamino; or
alkyl substituted with aromatic carbocyclyl sulfonylamino substituted with nitro;
or, alkyl substituted with unsubstituted non-aromatic carbocyclylsulfonyl; or
alkyl substituted with aromatic carbocyclylsulfonyl substituted with halogen;
hereinafter referred to as C-3.

$R^7$ includes, for example,
unsubstituted carbamoyl;
carbamoyl substituted with unsubstituted non-aromatic heterocyclyl; or
carbamoyl substituted with non-aromatic heterocyclyl substituted with alkyloxycarbonyl, haloalkyl, non-aromatic carocyclylcarbonyl, alkylcarbonyl, haloalkylcarbonyl, alkylsulfonyl, alkylcarbonyloxyalkylcarbonyl, hydroxyalkylcarbonyl, alkyloxycarbonyl or alkyl;
carbamoyl substituted with unsubstituted non-aromatic carbocyclyl; or
carbamoyl substituted with non-aromatic carbocyclyl substituted with halogen,
haloalkyl,
cyano,
aromatic carbocyclyl substituted with halogen,
or unsubstituted aromatic carbocyclyl;
carbamoyl substituted with non-aromatic heterocyclyl substituted with unsubstituted aromatic heterocyclyl; or
carbamoyl substituted with aromatic heterocyclyl substituted with halogen; carbamoyl substituted with unsubstituted aromatic carbocyclyl; or
carbamoyl substituted with aromatic carbocyclyl substituted with halogen, cyano, alkyl, haloalkyl, aromatic carbocyclyloxy, alkyloxy, haloalkyloxy or alkylamino;
or, carbamoyl substituted with unsubstituted alkyl; or
carbamoyl substituted with alkyl substituted with
cyano,
aromatic carbocyclyl substituted with halogen,
unsubstituted aromatic carbocyclyl,
hydroxyl,
halogen,
alkyloxycarbonyl
or non-aromatic heterocyclyl;
hereinafter referred to as C-4.

$R^7$ includes, for example,
unsubstituted non-aromatic heterocyclylcarbonyl;
non-aromatic heterocyclylcarbonyl substituted with oxo;
non-aromatic heterocyclylcarbonyl substituted with cyano;
non-aromatic heterocyclylcarbonyl substituted with hydroxy;
non-aromatic heterocyclylcarbonyl substituted with hydroxyimino;
non-aromatic heterocyclylcarbonyl substituted with non-aromatic heterocyclyl;
non-aromatic heterocyclylcarbonyl substituted with unsubstituted amino; or
non-aromatic heterocyclylcarbonyl substituted with amino substituted with alkyl,
alkylcarbonyl substituted with halogen, non-aromatic carbocyclyl or hydroxyl, unsubstituted alkylcarbonyl,
alkylsulfonyl,
alkyloxycarbonyl substituted with halogen or aromatic carbocyclyl,
or unsubstituted alkyloxycarbonyl,
non-aromatic heterocyclylcarbonyl substituted with unsubstituted alkyloxyimino; or
non-aromatic heterocyclylcarbonyl substituted with alkyloxyimino substituted with carbamoyl, non-aromatic heterocyclylcarbonyl, hydroxyl, alkyloxy, halogen or non-aromatic carbocyclyl;
on-aromatic heterocyclylcarbonyl substituted with unsubstituted alkylcarbonyl; or non-aromatic heterocyclylcarbonyl substituted with alkylcarbonyl substituted with hydroxy;
non-aromatic heterocyclylcarbonyl substituted with substituted or unsubstituted non-aromatic carbocyclyloxyimino;
non-aromatic heterocyclylcarbonyl substituted with unsubstituted alkyloxy; or
non-aromatic heterocyclylcarbonyl substituted with alkyloxy substituted with hydroxy, carboxy, amino substituted with alkylcarbonyl, unsubstituted amino, alkyloxycarbonyl, alkylamino or carbamoyl;
or non-aromatic heterocyclylcarbonyl substituted with unsubstituted alkyl; or non-aromatic heterocyclylcarbonyl substituted with alkyl substituted with hydroxy or halogen;
hereinafter referred to as C-5.

$R^7$ includes, for example, substituted or unsubstituted non-aromatic heterocyclylcarbonyl;
hereinafter referred to as C-6.

$R^7$ includes, for example,
non-aromatic heterocyclylcarbonyloxy substituted with alkyloxy optionally substituted with the substituent group H;
alkylcarbonyloxy optionally substituted with the substituent group E;
alkylcarbonyloxy optionally substituted with the substituent group G;
non-aromatic carbocyclyloxy optionally substituted with the substituent group C;
aromatic heterocyclyloxy optionally substituted with the substituent group C;
non-aromatic heterocyclyloxy optionally substituted with the substituent group C;
aromatic heterocyclylalkyloxy optionally substituted with the substituent group C;
non-aromatic heterocyclylcarbonyloxy optionally substituted with the substituent group C;
hereinafter referred to as C-7.

$R^7$ includes, for example,
non-aromatic heterocyclylcarbonyl substituted with
alkyloxy optionally substituted with the substituent group H;
alkylcarbonyloxy optionally substituted with the substituent group E;
alkylcarbonyloxy optionally substituted with the substituent group G;
aromatic heterocyclyloxy optionally substituted with the substituent group C;
aromatic heterocyclylalkyloxy optionally substituted with the substituent group C; or
non-aromatic heterocyclylcarbonyloxy optionally substituted with the substituent group C;
hereinafter referred to as C-8.

$R^7$ includes, for example,
non-aromatic heterocyclylcarbonyl substituted with
alkyloxy optionally substituted with the substituent group H;
aminocarbonyloxy optionally substituted with the substituent group G; or
aromatic heterocyclyloxy optionally substituted with the substituent group C;
hereinafter referred to as C-9.

$R^7$ includes, for example,
non-aromatic heterocyclylcarbonyl substituted with unsubstituted alkyloxy;
alkyloxy substituted with unsubstituted amidino, amidino substituted with hydroxy, halogen, hydroxy, carboxy, hydrazide, cyano, carbamoyl, or alkyloxycarbonyl;
unsubstituted alkylcarbonyloxy;
aminocarbonyloxy substituted with unsubstituted non-aromatic carbocyclyl, non-aromatic carbocyclyl substituted with hydroxy, alkyl, alkyloxy, haloalkyl, hydroxyalkyl, cyanoalkyl, or alkylcarbonylamino;
unsubstituted aromatic heterocyclyloxy;
aromatic heterocyclyloxy substituted with alkyl, haloalkyl, alkyloxy, or non-aromatic carbocyclyl;
unsubstituted aromatic heterocyclylalkyloxy;
aromatic heterocyclylalkyloxy substituted with alkyl, haloalkyl or alkyloxy;
unsubstituted non-aromatic heterocyclylcarbonyloxy; or
non-aromatic heterocyclylcarbonyloxy substituted with hydroxyl;
hereinafter referred to as C-10.

$R^7$ includes, for example,
non-aromatic heterocyclylcarbonyl substituted with unsubstituted alkyloxy;
alkyloxy substituted with unsubstituted amidino, amidino substituted with hydroxy, halogen, hydroxy, carboxy, hydrazide, cyano, carbamoyl, or alkyloxycarbonyl;
aminocarbonyloxy substituted with unsubstituted non-aromatic carbocyclyl, non-aromatic carbocyclyl substituted with hydroxy, alkyl, alkyloxy, haloalkyl, hydroxyalkyl, cyanoalkyl, or alkylcarbonylamino;
unsubstituted non-aromatic heterocyclyloxy; or
aromatic heterocyclyloxy substituted with alkyl, haloalkyl, alkyloxy, or non-aromatic carbocyclyl;
hereinafter referred to as C-11.

X is —NH— or —S—, preferably X is —S—.
Z is —O— or —S—, preferably Z is —S—.
As to "b", 0, 1 or 2 are exemplified; hereinafter referred to as D-1.
"b" includes, for example, 0; hereinafter referred to as D-2.
As to $R^{7'}$, each independently, hydroxy, halogen, cyano, substituted or unsubstituted amino, substituted or unsubstituted alkyl are exemplified; hereinafter referred to as E-1.

The compounds of formula (I) or formula (III) are not limited to specific isomers but include all possible isomers (e.g., keto-enol isomers, imine-enamine isomers, diastereoisomers, enantiomers, rotamers or the like), racemates or mixtures thereof.

In the description, in the group represented by the following formula:

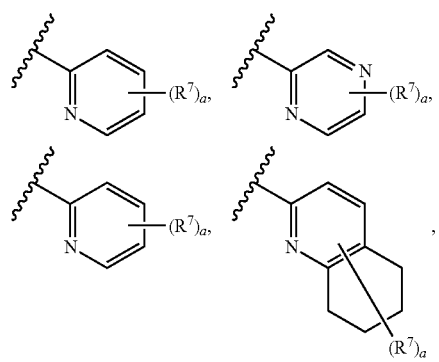

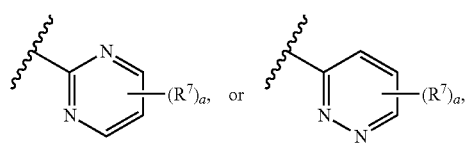

$R^7$ of the numbers of "a" can be each independently attached to substitutable atom that consists of the ring. In the case of the condensed ring, $R^7$ of the numbers of "a" can be attached to substitutable atom that consists of the rings.

Similarly, in the description, in the group represented by the following formula:

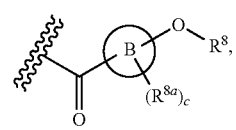

$R^{8a}$ of the numbers of "c" can be each independently attached to substitutable atom that consists of the ring. In the case of the condensed ring, bridged ring, or having spiro ring, $R^{8a}$ of the numbers of "c" can be each independently attached to substitutable atom that consists of the rings.

Similarly, in the description, in the group represented by the following formula:

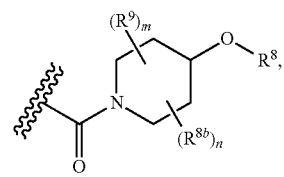

$R^9$ of the numbers of "m" can be each independently attached to substitutable atom that consists of the ring. Also, $R^{8b}$ of the numbers of "n" can be each independently attached to substitutable atom that consists of the ring.

Similarly, in the description, in the group represented by the following formula:

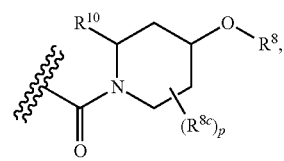

$R^{8c}$ of the numbers of "p" can be each independently attached to substitutable atom that consists of the ring.

Similarly, in the description, the bridge that two $R^9$ may be taken together to form or $R^{9a}$ and $R^{9b}$ may be taken together to form includes two kinds of steric structure (Up/Down) relative to the piperazine ring.

For example, the following steric structures (Up) are included.

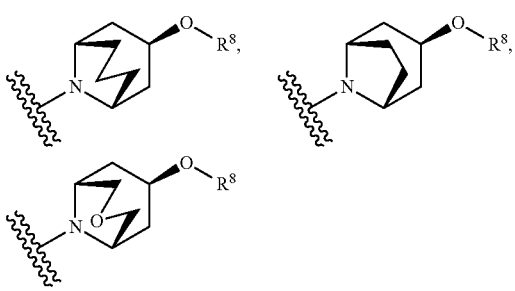

For example, the following steric structures (Down) are included.

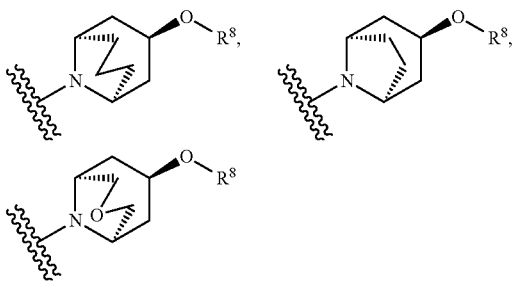

One or more hydrogen, carbon and/or other atom(s) in the compounds of formula (I) or formula (III) may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds of formula (I) or formula (III) include the compounds replaced with these isotopes. The compounds replaced with the above isotopes are useful as medicines and include all of radiolabeled compounds of the compound of formula (I) or formula (III). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds of formula (I) or formula (III) can be prepared using well-known methods in this field of the invention. For example, a tritium-labeled compound of formula (I) or formula (III) can be prepared by introducing a tritium to a certain compound of formula (I) or formula (III), through a catalytic dehalogenation reaction using a tritium. This method comprises reacting with an appropriately-halogenated precursor of the compound of formula (I) or formula (III) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds of formula (I) or formula (III) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, diethanolamine, ethylenediamine, pyridine, picoline, quinoline or the like), salts with amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds of formula (I) or formula (III) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds of formula (I) or formula (III). When the compounds of formula (I) or formula (III) or pharmaceutically acceptable salts thereof are allowed to stand in the atmosphere, the compounds may absorb water, resulting in attachment of adsorbed water or formation of hydrates. Recrystallization of the compounds of formula (I) or formula (III) or pharmaceutically acceptable salts thereof may produce crystal polymorphs.

The compounds of formula (I) or formula (III) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds of formula (I) or formula (III) through enzymatic oxidation, reduction, hydrolysis or the like under physiological conditions in vivo, compounds that are converted to the compounds of formula (I) or formula (III) through hydrolysis by gastric acid etc., and the like. Methods for selecting and preparing suitable prodrug derivatives are described in, for example, "Design of Prodrugs, Elsevier, Amsterdam, 1985". Prodrugs themselves may have some activity.

When the compounds of formula (I) or formula (III) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-$PhSO_3-$, $PhSO_3-$ and p-$CH_3PhSO_3$.

General procedures for the synthesis of the compounds of the present invention are described below. Starting materials and reaction reagents used in such synthesis are commercially available or can be synthesized according to methods well known in the art using compounds commercially available.

In the following all steps, when a substituent which impedes a reaction, e.g. hydroxy, mercapto, amino, formyl, carbonyl, carboxy, is possessed, the substituent is protected by the method described in Protective Groups in organic Synthesis, and Theodora W Greene (John Wiley & Sons, hereinafter referred to as literature A) in advance, and the protecting group may be removed at a desirable stage. In addition, in the all steps, an order of steps to be implemented may be appropriately changed, and each intermediate may be isolated, and used in a next step. All of reaction time, reaction temperature, solvents, reagents, protecting groups, etc. are mere exemplification and not limited as long as they do not cause an adverse effect on a reaction.

For example, the compounds of formula (I) or formula (III) of the present invention can be prepared by the general synthetic methods described below.

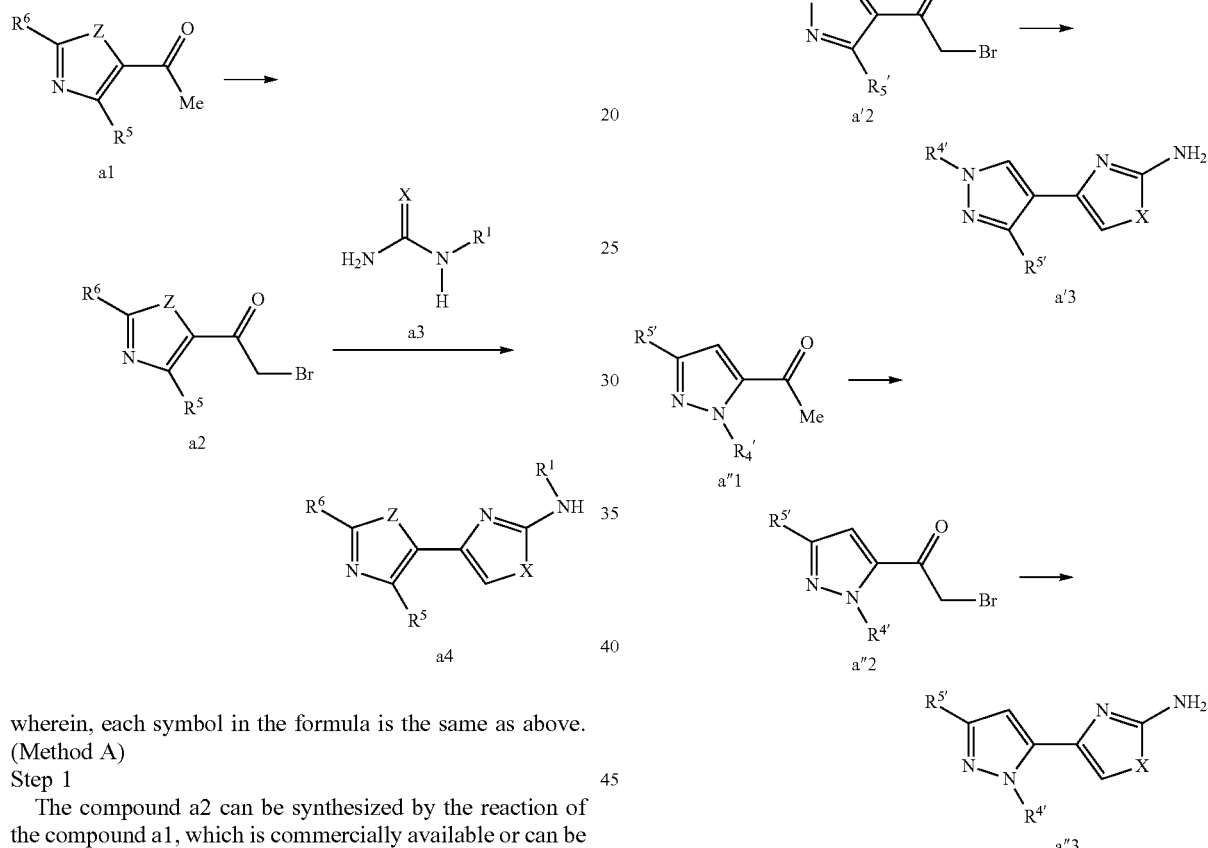

wherein, each symbol in the formula is the same as above.
(Method A)
Step 1

The compound a2 can be synthesized by the reaction of the compound a1, which is commercially available or can be synthesized according to the known methods, with a brominating agent.

The reaction temperature is −20° C. to the reflux temperature, preferably 25° C. to the reflux temperature.

The reaction time is 0.1 to 12 hours, preferably 0.5 to 8 hour(s).

As the brominating agent, pyridinium tribromide, tetrabutylammonium bromide, bromide and the like are exemplified, and 1 to 2 mole equivalent(s) can be used per an equivalent of the compound a1.

As the reaction solvent, dichloromethane, chloroform and the like are exemplified.
Step 2

The compound a4 can be synthesized by the reaction of the compound a2 with the compound a3.

The reaction temperature is 0° C. to the reflux temperature, preferably 10° C. to the reflux temperature.

The reaction time is 0.1 to 24 hours, preferably 0.5 to 12 hour(s).

1 to 2 mole equivalent(s) of the compound a3 can be used per an equivalent of the compound a2.

As the reaction solvent, methanol, ethanol, THF, DMF and the like are exemplified.

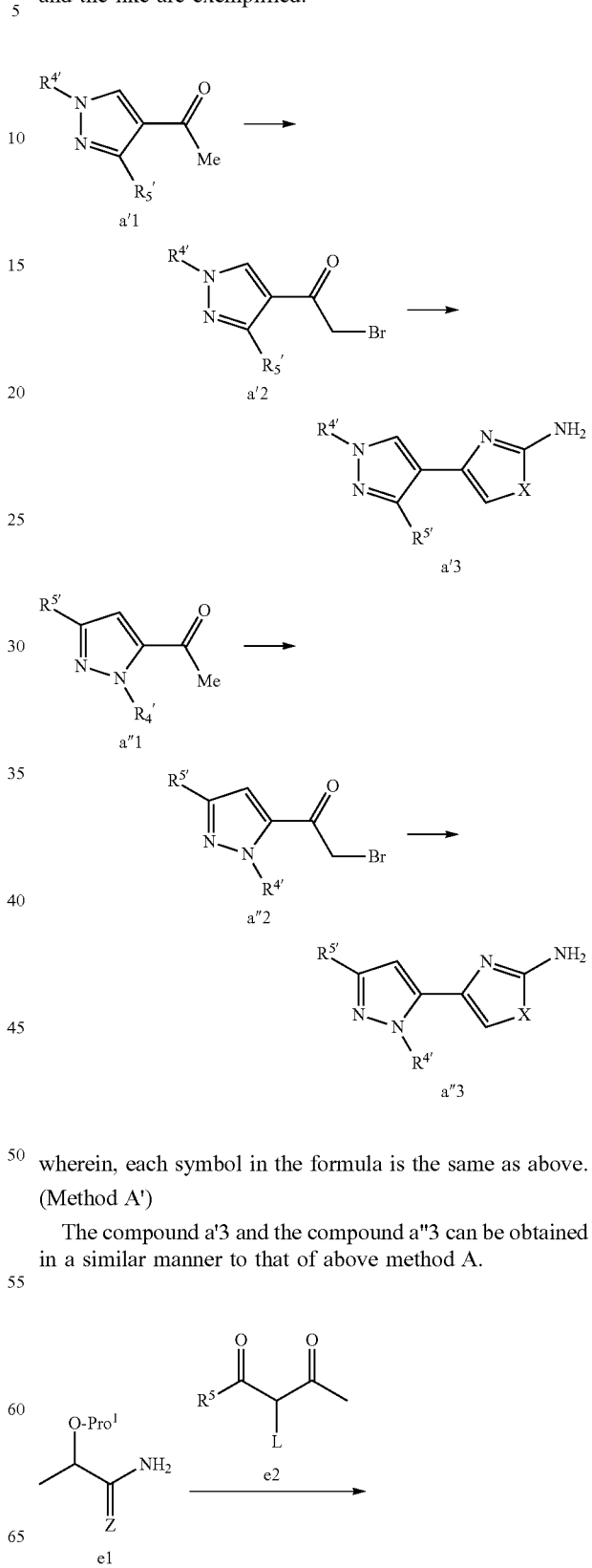

wherein, each symbol in the formula is the same as above.
(Method A')

The compound a'3 and the compound a"3 can be obtained in a similar manner to that of above method A.

-continued

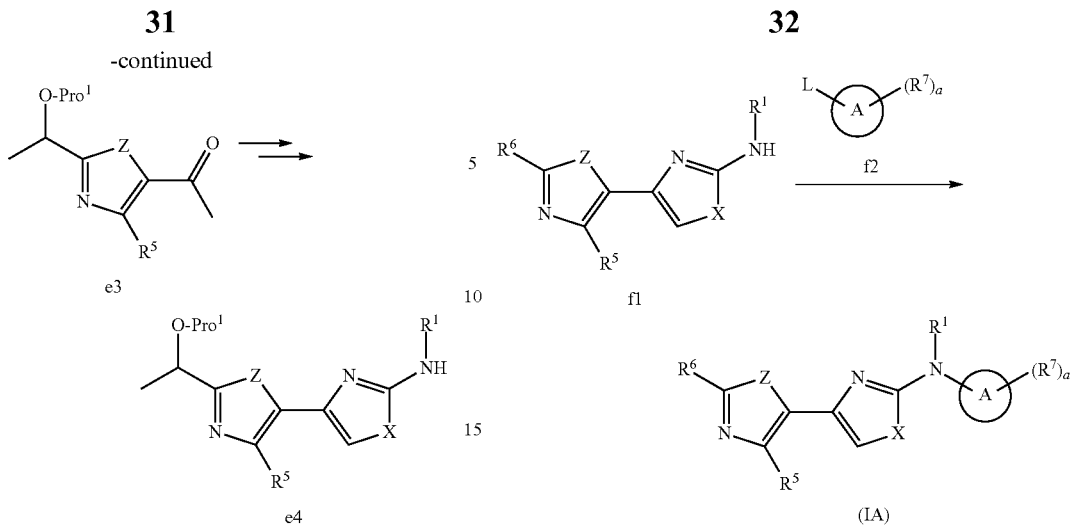

wherein $R^1$, $R^5$, X and Z are the same as the above; L is a leaving group (halogen, tosylate, mesylate or the like); $Pro^1$ is a protecting group of hydroxy group (Ac, TBS, or the like)

(Method E)

Step 1

The compound e3 can be synthesized by the reaction of the compound e1 with the compound e2.

1 to 5 mole equivalent(s) of the compound e2 can be used per an equivalent of the compound e1.

The reaction temperature is 20° C. to the reflux temperature, preferably 50° C. to the reflux temperature.

The reaction time is 0.1 to 48 hour(s), preferably 0.5 to 12 hour(s).

As the reaction solvent, ethanol, isopropanol, water and the like are exemplified. The reaction solvent may be used alone or in combination.

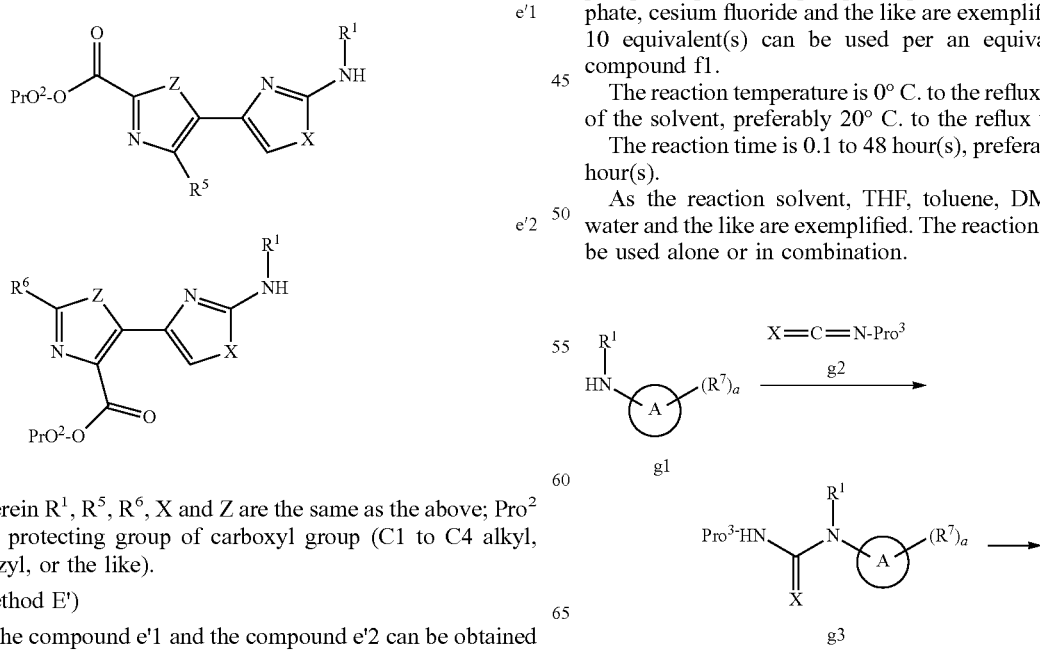

wherein $R^1$, $R^5$, $R^6$, X and Z are the same as the above; $Pro^2$ is a protecting group of carboxyl group (C1 to C4 alkyl, benzyl, or the like).

(Method E')

The compound e'1 and the compound e'2 can be obtained in a similar manner to that of above method E.

wherein $R^1$, $R^5$, $R^6$, $R^7$, X, Z, ring A and "a" are the same as above; L is a leaving group (halogen, tosylate, mesylate or the like).

(Method F)

Compound (IA) can be synthesized by reaction of Compound f1 and Compound f2 in the presence of a metal catalyst, a phosphine ligand and a base.

As the metal catalyst, palladium acetate, bis(dibenzylideneacetone)palladium, tetrakis(triphenylphosphine)palladium, bis(triphenylphosphine)palladium(II) dichloride, bis(tri-tert-butylphosphine)palladium, bis(di-tert-butyl(4-dimethylaminophenyl)phosphine)dichloropalladium(II) and the like are exemplified, and it can be used at 1 to 5 mole equivalent(s) relative to Compound f1.

As the phosphine ligand, X-Phos, Xantphos, t-BuBrettPhos, RuPhos and the like are exemplified, and it can be used at 0.001 to 0.5 mole equivalent(s) relative to Compound f1.

As the base, lithium hydroxide, sodium hydroxide, potassium hydroxide, potassium tert-butoxide, sodium tert-butoxide, sodium carbonate, potassium carbonate, sodium hydrogen carbonate, sodium phosphate, sodium hydrogen phosphate, potassium phosphate, potassium hydrogen phosphate, cesium fluoride and the like are exemplified, and 1 to 10 equivalent(s) can be used per an equivalent of the compound f1.

The reaction temperature is 0° C. to the reflux temperature of the solvent, preferably 20° C. to the reflux temperature.

The reaction time is 0.1 to 48 hour(s), preferably 0.5 to 24 hour(s).

As the reaction solvent, THF, toluene, DMF, dioxane, water and the like are exemplified. The reaction solvent may be used alone or in combination.

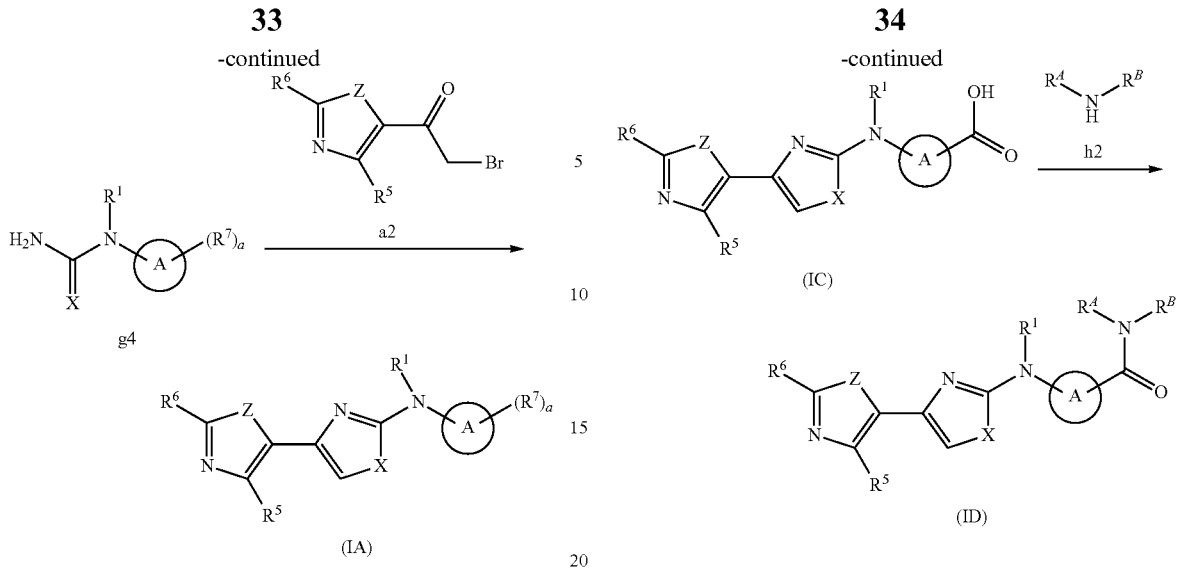

wherein $R^1$, $R^5$, $R^6$, $R^7$, Z, ring A, ring D and "a" are the same as above; X is O or S; $Pro^3$ is a protecting group of amino group (Bz, Boc, Cbz or the like).

(Method G)
Step 1
The compound g3 can be synthesized by the reaction of the compound g1 with the compound g2.

The reaction temperature is 0° C. to the reflux temperature, preferably 10° C. to the reflux temperature.

The reaction time is 0.1 to 24 hours, preferably 0.5 to 12 hour(s).

1 to 2 mole equivalent(s) of the compound g2 can be used per an equivalent of the compound g1.

As the reaction solvent, methanol, ethanol, THF, DMF and the like are exemplified.

Step 2
Compound g4 can be obtained by deprotection of amino protecting group of Compound g3. For example, amino protecting group can be suitably removed using a method described in the literature A and the like.

Step 3
Compound (IA) can be synthesized by reaction of Compound g4 and Compound a2 in a similar manner to that of above method A step 2.

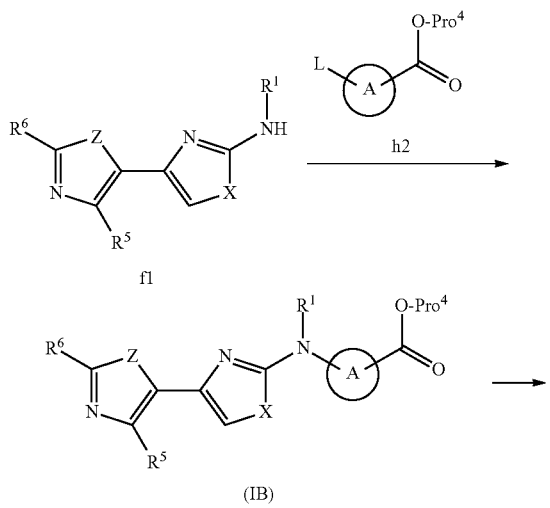

wherein $R^1$, $R^5$, $R^6$, X, Z and ring A are the same as above; $Pro^4$ is a protecting group of carboxyl group (C1 to C4 alkyl, benzyl or the like); $R^A$ and $R^B$ are each independently hydrogen atom, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or $R^A$ and $R^B$ may be taken together with the nitrogen atom which is attached to them to form substituted or unsubstituted non-aromatic heterocycle.

(Method H)
Step 1
Compound (IB) can be synthesized by reaction of Compound h1 and Compound h2 in the presence of a metal catalyst, a phosphine ligand and a base in a similar manner to that of above method F.

Step 2
Compound (IC) can be obtained by deprotection of amino protecting group of Compound IB. For example, amino protecting group can be suitably removed using a method described in the literature A and the like.

Compound (ID) can be synthesized by reaction of Compound (IC) and Compound h2 in the presence of a condensing agent and a base.

As the condensing agent, COMU, EDC and the like are exemplified, and it can be used at 1 to 5 mole equivalent(s) relative to Compound (IC).

As the base, pyridine, triethylamine, diisopropylethylamine and the like are exemplified, and it can be used at 1 to 5 mole equivalent(s) relative to Compound (IC)

The reaction temperature is 20° C. to the reflux temperature, preferably 50° C. to the reflux temperature.

The reaction time is 0.1 to 48 hour(s), preferably 0.5 to 12 hour(s).

As the reaction solvent, THF, toluene, DMF, DMSO, NMP, dioxane, water and the like are exemplified, and it can be used alone or in combination.

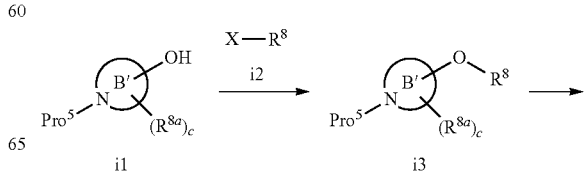

-continued

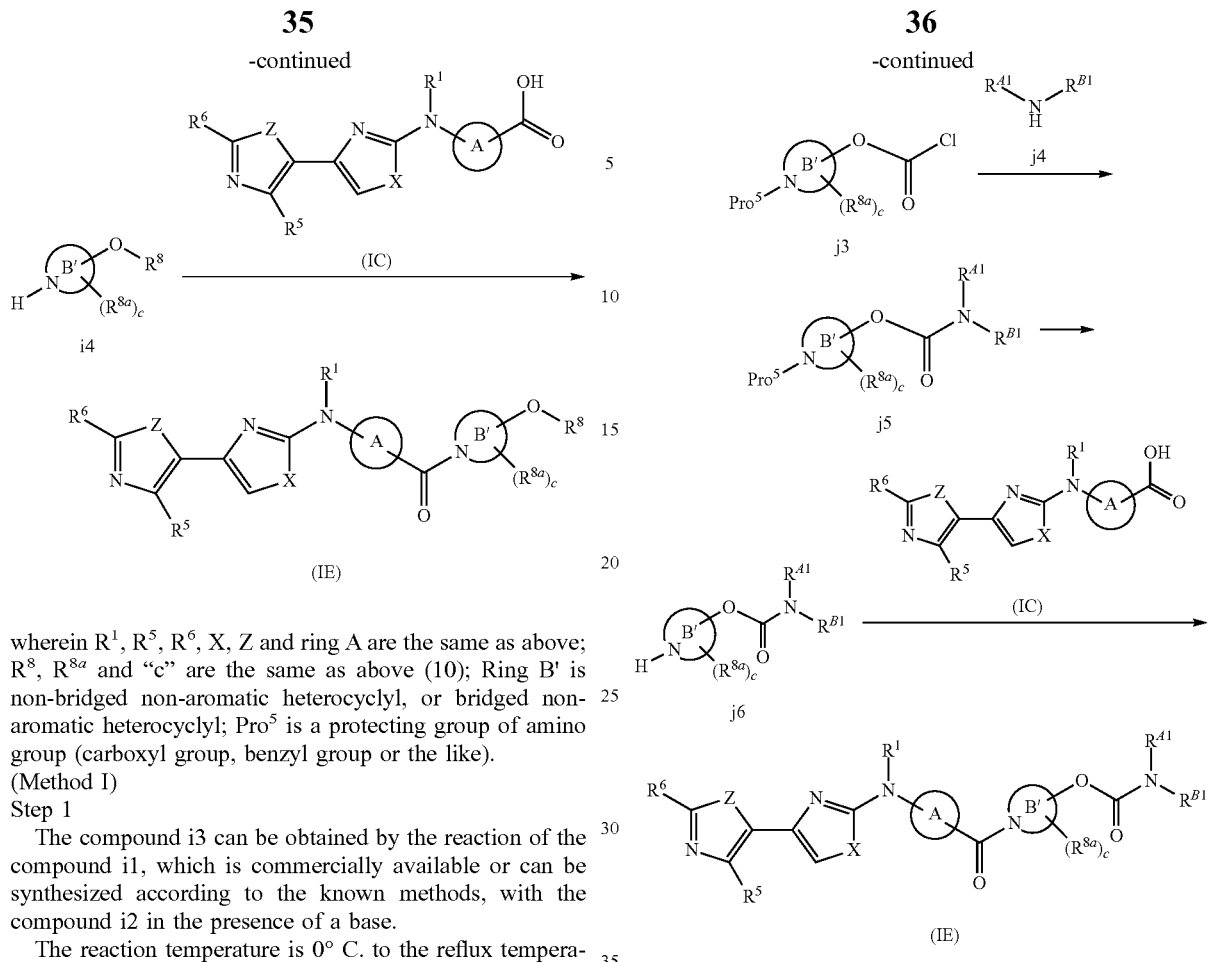

wherein $R^1$, $R^5$, $R^6$, X, Z and ring A are the same as above; $R^8$, $R^{8a}$ and "c" are the same as above (10); Ring B' is non-bridged non-aromatic heterocyclyl, or bridged non-aromatic heterocyclyl; $Pro^5$ is a protecting group of amino group (carboxyl group, benzyl group or the like).

(Method I)
Step 1

The compound i3 can be obtained by the reaction of the compound i1, which is commercially available or can be synthesized according to the known methods, with the compound i2 in the presence of a base.

The reaction temperature is 0° C. to the reflux temperature, preferably 10° C. to the reflux temperature.

The reaction time is 0.1 to 12 hour(s), preferably 0.5 to 8 hour(s).

1 to 2 mole equivalent(s) of the compound i2 can be used per an equivalent of the compound i1.

As the base, sodium hydride, sodium t-butoxy, potassium t-butoxy, trimethylamine, diisopropylethylamine or the like are exemplified.

As the reaction solvent, THF, DMF, DMSO, and the like are exemplified.

Step 2

Compound i4 can be obtained by deprotection of protecting group, which is carboxyl group or benzyl group or the like, of Compound i3. For example, protecting group can be suitably removed using a method described in the literature A and the like Step 3

Compound (1E) can be synthesized by reaction of Compound (IC) and Compound i4 in the presence of a condensing agent and a base in a similar manner to that of above step 3 of method H.

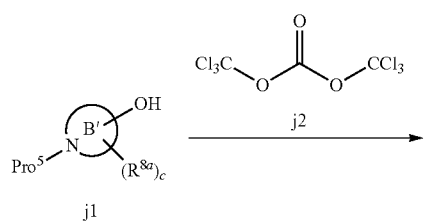

wherein $R^1$, $R^5$, $R^6$, X, Z, ring A, $R^{8a}$, "c", Ring B' and $Pro^5$ are the same as above; $R^{A1}$ and $R^{B1}$ are each independently hydrogen atom, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or $R^{A1}$ and $R^{B1}$ may be taken together with the nitrogen atom which are attached to them to form substituted or unsubstituted non-aromatic heterocycle.

(Method J)
Step 1

The compound j3 can be obtained by the reaction of the compound j1, which is commercially available or can be synthesized according to the known methods, with the compound j2 in the presence of a base.

The reaction temperature is 0° C. to room temperature.

The reaction time is 0.1 to 12 hour(s), preferably 0.5 to 5 hour(s).

0.5 to 1 mole equivalent(s) of the compound a8 can be used per an equivalent of the compound a1.

As the base, pyridine, trimethylamine, diisopropylethylamine or the like are exemplified.

As the reaction solvent, dichloromethane, chloroform and the like are exemplified.

Step 2

The compound j5 can be obtained by the reaction of the compound j3 and the compound j4 in the presence of a base.

The reaction temperature is 0° C. to the reflux temperature, preferably 10° C. to the reflux temperature.

The reaction time is 0.1 to 12 hour(s), preferably 0.5 to 5 hour(s).

1 to 2 mole equivalent(s) of the compound j4 can be used per an equivalent of the compound j3.

As the base, pyridine, trimethylamine, diisopropylethylamine or the like are exemplified.

As the reaction solvent, dichloromethane, chloroform, THF, DMF, and the like are exemplified.

Step 3

Compound j6 can be obtained by deprotection of protecting group, which is carboxyl group or benzyl group or the like, of Compound j5. For example, protecting group can be suitably removed using a method described in the literature A and the like.

Step 4

Compound (1E) can be synthesized by reaction of Compound (IC) and Compound j6 in the presence of a condensing agent and a base in a similar manner to that of above step 3 of method H.

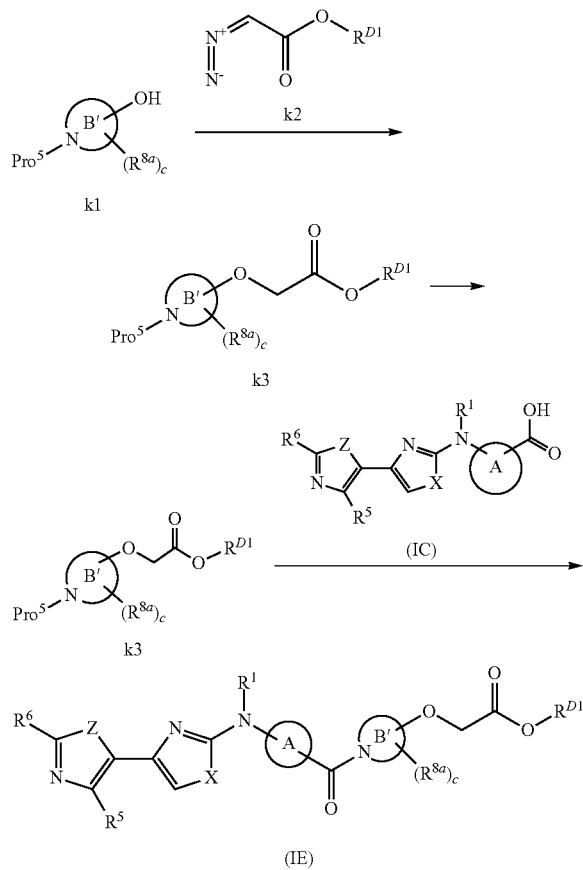

wherein $R^1$, $R^5$, $R^6$, X, Z, Ring A, $R^{8a}$, "c", Ring B' and $Pro^5$ are the same as above; $R^{D1}$ is hydrogen atom, substituted or unsubstituted alkyl or the like.

(Method k)

Step 1

The compound k3 can be obtained by the reaction of the compound k1, which is commercially available or can be synthesized according to the known methods, with the ester diazoacetate or the like (the compound k2).

The reaction temperature is −20° C. to the reflux temperature, preferably 25° C. to the reflux temperature.

The reaction time is 0.1 to 12 hour(s), preferably 0.5 to 8 hour(s).

As the ester diazoacetate, methyl diazoacetate, ethyl, t-butyl, benzyl or the like are exemplified.

1 to 2 mole equivalent(s) of the ester diazoacetate can be used per an equivalent of the compound k1.

As the reaction solvent, dichloromethane, chloroform, and the like are exemplified.

Step 2

Compound k4 can be obtained by deprotection of protecting group, which is carboxyl group or benzyl group or the like, of Compound k3. For example, protecting group can be suitably removed using a method described in the literature A and the like.

Step 3

Compound (1E) can be synthesized by reaction of Compound (IC) and Compound k4 in the presence of a condensing agent and a base in a similar manner to that of above step 3 of method H.

Compounds of formula (I), formula (I') or formula (I''), formula (I'''), formula (II) or formula (III) of the present invention prepared by above general synthetic method can be purified by referring to the known methods (e.g., chromatography, recrystallization and the like).

In another embodiment, the invention provides a pharmaceutical composition comprising an effective amount of Compound of the invention, in combination with a pharmaceutically acceptable carrier.

For use of Compound of the invention as a medicament, a pharmaceutical composition can be prepared according to conventional methods, using pharmaceutically acceptable carriers well known in the art, such as excipients, binders, disintegrants, lubricants, colourants, flavors, odor improving agents, surfactants, etc.

For the pharmaceutical composition of the invention to be administered in the treatment of mammals including human, an appropriate unit dosage form may be selected depending on the purpose of the treatment and the route of administration. Specifically, such unit dosage form includes oral formulations such as tablet, coated tablet, powder, granule, capsule, liquid, pill, suspension, emulsion, etc., and parenteral formulations such as injectable solution, suppository, ointment, patch, aerosol, etc. Such unit dosage form can be formulated according to methods well known in the art.

The amount of Compound in a formulation can be varied depending on its dosage form, route for administration, dosing regimen, etc.

Route for administration of the pharmaceutical composition can be determined depending on dosage form, age, sex, body weight, severity of the disease, and other factors, etc., and may be selected from various routes such as oral, subcutaneous, transdermal, rectal, intranasal, buccal, etc.

Dose of Compound of the invention in a pharmaceutical composition of the invention can be determined depending on the choice of route for administration, age, sex, body weight, severity of the disease, Compound to be administered, and other factors, etc., and can be generally from 0.05 to 1000 mg/kg/day, preferably from 0.1 to 10 mg/kg/day, for oral administration to adults. For parenteral administration, dose can be varied widely depending on its route but generally from 0.005 to 100 mg/kg/day, preferably from 0.01 to 1 mg/kg/day. Such pharmaceutical composition of the invention may be administered once a day or in several times at a divided dosage in a day.

Following examples illustrate the present invention in more detail, however the present invention is not limited to these examples. In NMR data shown in Examples and Reference Examples, not all measured peaks may be described. The meaning of each abbreviation is as follows.
Me: methyl
Et: ethyl
n-: normal
t-Bu: tert-butyl
i-Pr: isopropyl
$CF_3$: trifluoromethyl
Ph: phenyl
Bn: benzyl
Bz: benzoyl
Ac: acetyl
Ms: methanesulfonyl
Ts: p-toluenesulfonyl
Boc: tert-butoxycarbonyl
$Boc_2O$: di-tert-butyldicarbonate
COMU: (1-cyano-2-ethoxy-2-oxoethylideneaminooxy)dimethylamino(morpholino)carbenium hexafluorophosphate
DMSO: dimethyl sulfoxide
DMA: N,N-dimethylacetamide
DMF: N,N-dimethylformamide
THF: tetrahydrofuran
NMP: N-methylpyrrolidone
CDI: carbonyldiimidazole
DIEA: N,N-diisopropylethylamine
Py: pyridine
$Et_3N$: triethylamine
TFA: trifluoroacetic acid
EDCI: 1-(3-Dimethylaminopropyl)-3-ethylcarbodiimide hydrochloride
EDC: 1-ethyl-3-(3-dimethylaminopropyl)carbodiimide
HATU: O-(7-azabenzotriazol-1-yl)-N,N,N'N'-tetramethyluronium hexafluorophosphate
$Pd_2(dba)_3$-tris(dibenzylideneacetone)dipalladium (0)
$PdCl_2(dppf)$: [1,1',1'-bis(diphenylphosphino)ferrocene]dichloropalladium (II) complex with dichloromethane
HPLC: High performance liquid chromatography
X-Phos: 2-(dicyclohexylphosphino)-2',4',6'-triisopropylbiphenyl
Xantphos: 4,5-bis(diphenylphosphino)-9,9-dimethylxanthene
t-BuBrettPhos: 2-(Di-tert-butylphosphino)-2',4',6'-triisopropyl-3,6-dimethoxy-1,1'-biphenyl
TBS: tert-butyldimethylsilyl
Cbz: benzyloxycarbonyl
TMSOTf: trimethylsilyl trifluoromethanesulfonate
NBS: N-bromosuccinimide
DMAP: 4-dimethylaminopyridine
DIBAL: diisobutylaluminum hydride
"Wedged bond" and "dashed bond" in the chemical formula represent configuration.
(Method of Identification for Compound)
LC/MS data of Compound of the present invention were measured under any one of the following ten conditions (Methods 1 to 10), and a retention time and MS (m/z) were shown.
(Method 1)
Column: Shim-pack XR-ODS (2.2 μm, i.d. 50×3.0 mm) (Shimadzu)
Flow rate: 1.6 mL/min
UV detection wavelength: 254 nm
Mobile phase: [A] is 0.1% formic acid containing aqueous solution, and [B] is 0.1% formic acid containing acetonitrile solution
Gradient: Linear gradient of 10% to 100% solvent [B] for 3 minutes was performed, and 100% solvent [B] was maintained for 0.5 minute.

(Method 5)
Column: ACQUITY UPLC® BEH C18 (1.7 μm, i.d. 2.1×50 mm) (Waters)
Flow rate: 0.8 mL/min
UV detection wavelength: 254 nm
Mobile phase: [A] is 0.1% formic acid containing aqueous solution, and [B] is 0.1% formic acid containing acetonitrile solution
Gradient: Linear gradient of 5% to 100% solvent [B] for 3.5 minutes was performed, and 100% solvent [B] was maintained for 0.5 minute.

Example 1

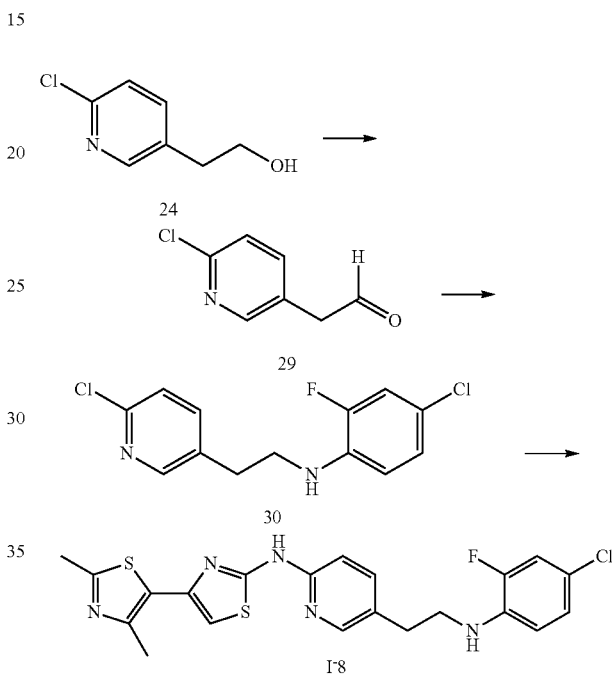

Step 1 Synthesis of Compound 29

Under an atmosphere of nitrogen, the commercially available compound 24 (822 mg, 5.22 mmol) was dissolved in dichloromethane (24 mL), and then sodium bicarbonate (4382 mg, 52.2 mmol) was added. The reaction mixture was stirred at room temperature for 5 minutes, 0.3 mol/L Dess-Martin reagent (26.1 mL, 7.82 mmol) in dichloromethane solution was added dropwise, and then stirred for 2 hours at the same temperature. 10% sodium thiosulfate aq. (15 mL) was added at room temperature, and the reaction mixture was stirred for 30 minutes. The saturated sodium hydroxide aq. (20 mL) was added to the reaction mixture, and extracted with chloroform (80 mL), and then dried over anhydrous magnesium sulfate. The solvent was evaporated, and the obtained residue was diluted with diethyl ether to be solidified. The precipitate was removed by filtration, the filtrate was evaporated to obtain compound 29 (800 mg, 98.6%).
LC/MS (Method 1) RT=0.86, $[M+H]^+$=155.95.

Step 2 Synthesis of Compound 30

Under an atmosphere of nitrogen, the compound 29 (800 mg, 5.14 mmol) was dissolved in a mixture of dichloromethane (4 mL) and acetic acid (4 mL). 4-Chloro-2-fluoroaniline (823 mg, 5.66 mmol) and Sodium Triacetoxyborohydride (1635 mg, 7.71 mmol) were added at room temperature, and then the reaction mixture was stirred for 16 hours at the same temperature. Saturated sodium bicarbonate aq. (30 mL) was added to the reaction mixture, and then extracted with chloroform (90 mL), and then dried over anhydrous magnesium sulfate. The solvent was evaporated, and the obtained residue was diluted with diethyl ether, and the obtained residue was purified with column chromatography on SiO₂ (ethyl acetate-hexane) to obtain the compound 30 (462 mg, 31.5%).

LC/MS (Method 1) RT=2.31, [M+H]⁺=285.00.

Example 2

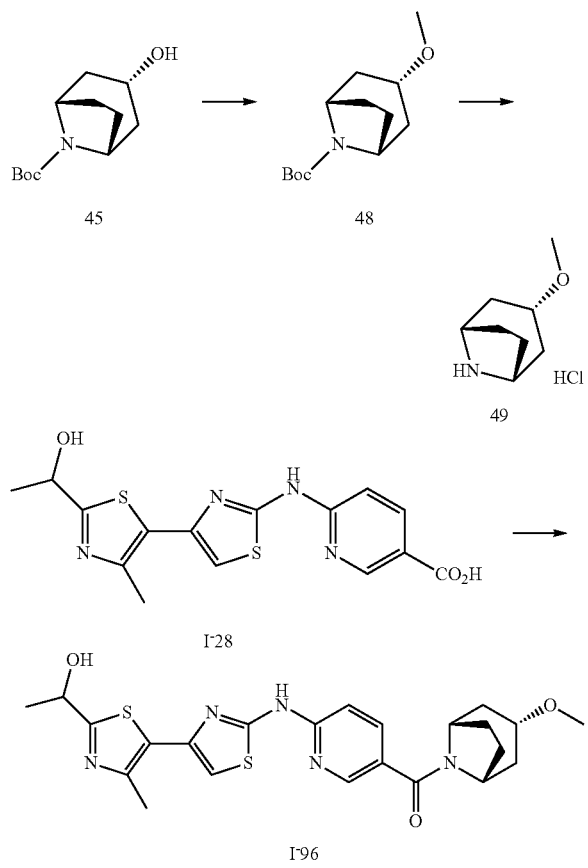

Step 1 Synthesis of Compound I-96

Under an atmosphere of nitrogen, the compound 45 (300 mg, 1.32 mmol) was dissolved in tetrahydrofuran (3 mL) and sodium hydride (60% oil suspensions, 58.1 mg, 1.45 mmol) was added at 0° C. and then the reaction mixture was stirred for 15 minutes at the same temperature. And then 4-methylbenzene sulfonic acid methyl ester (0.240 mL, 1.58 mmol) was added at 0° C. and then stirred at room temperature. After the all-night stand at room temperature, stirred for 5 hours at room temperature. Water and saturated sodium bicarbonate aq. were added to the reaction mixture, and was extracted with Ethyl acetate. The organic layer was washed with brine, and dried over anhydrous magnesium sulfate. The solvent was evaporated to obtain the compound 48 (467 mg).

The compound 48 (319 mg) was dissolved into 4 mol/L hydrogen chloride in dioxane solution (6 mL), and the reaction solution was stirred at room temperature for 1.5 hours. The solvent was evaporated, and the obtained residue was diluted with diethyl ether to be solidified. The precipitation was filtered and the compound 49 (212 mg) was obtained as the crude product.

H-NMR (DMSO-D₆) δ: 1.55-1.67 (m, 2H), 1.78-1.98 (m, 4H), 2.02-2.11 (m, 2H), 3.22 (s, 3H), 3.52-3.64 (m, 1H), 3.95-4.00 (m, 2H), 8.98 (s, 2H).

The compound I-28 (100 mg, 0.276 mmol) and the compound 49 (98 mg, 0.195 mmol) were dissolved into DMF (1 mL), and then triethylamine (0.076 mL, 0.552 mmol) and COMU (236 mg, 0.552 mmol) were added and the reaction mixture was stirred at room temperature for 1.5 hours. Water and saturated sodium bicarbonate aq. were added to the reaction mixture, and was extracted with ethyl acetate. The organic layer was washed with saturated sodium bicarbonate aq., water, and brine, and dried over anhydrous magnesium sulfate. The solvent was evaporated, and the obtained residue was purified with column chromatography on SiO₂ (Ethyl acetate-Methanol). The collected elution was evaporated and the obtained residue was solidified in diisopropyl ether-ethyl acetate. And the precipitate was filtered to obtain the compound I-96 (83 mg, yield 61.9%).

The following Compounds were obtained in accordance with the general synthetic methods and examples. The chemical structures and the physical properties (LC/MS data) of Compounds are described below.

In the following tables, Compound with "HCl" in the chemical structure means that Compound forms "HCl salt". Compound with plural "HCl" in the chemical structure means that Compound forms plural "HCl salt".

TABLE 1

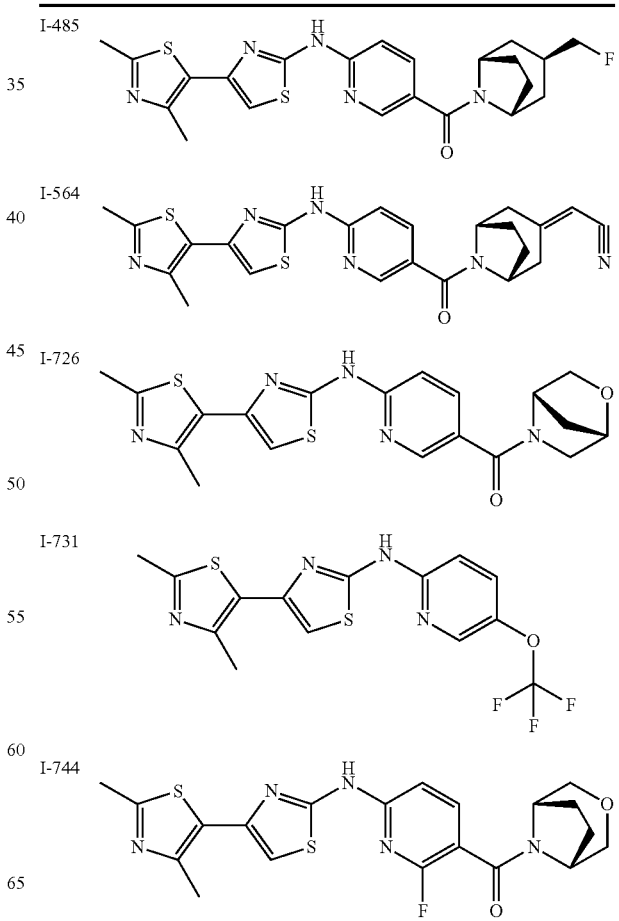

TABLE 1-continued
I-175 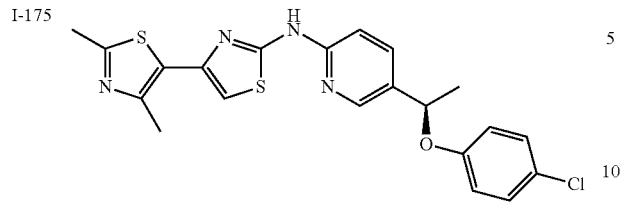
I-45 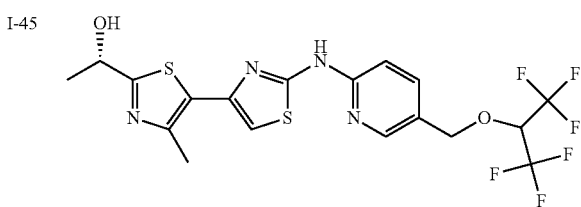
I-176 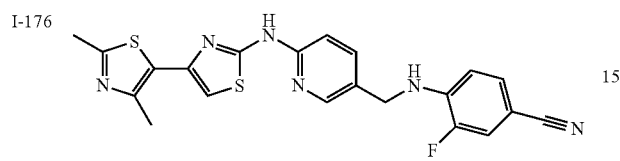
I-150 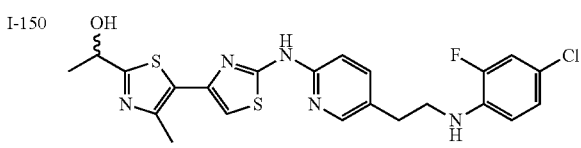
I-764 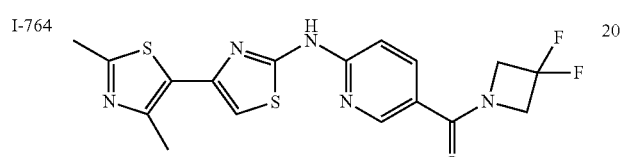
I-6 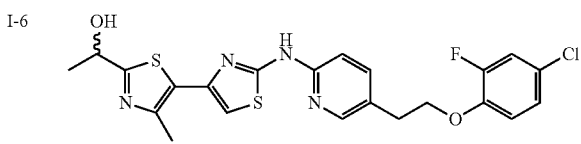
I-140 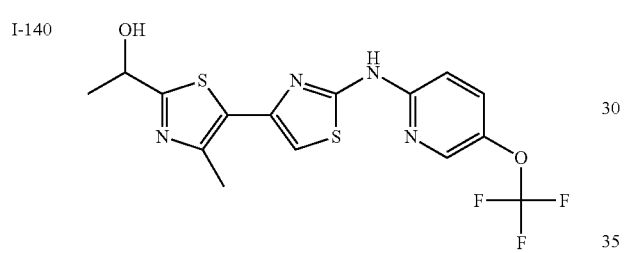
I-226 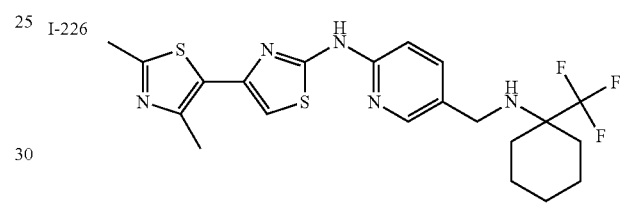
I-141 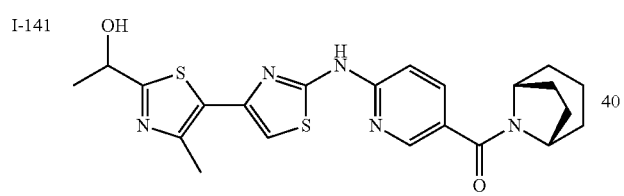
I-203 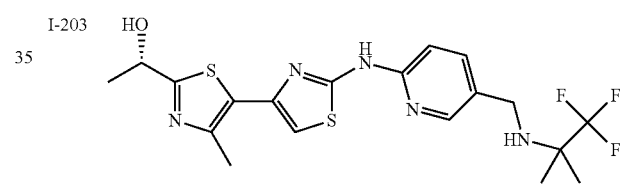
I-248 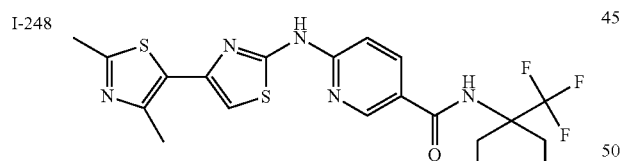
I-204 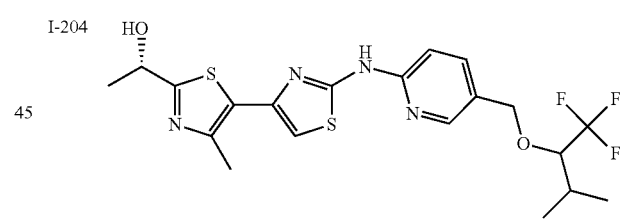
I-308 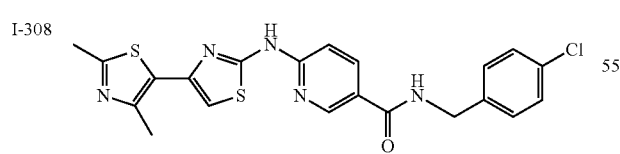
I-96 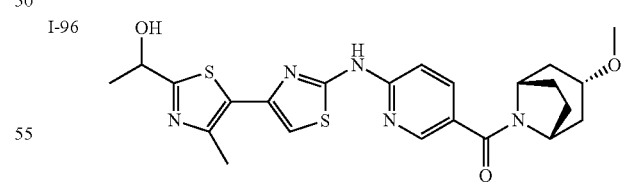
I-187 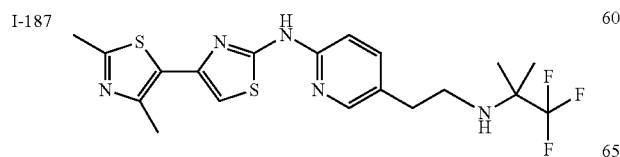
I-132 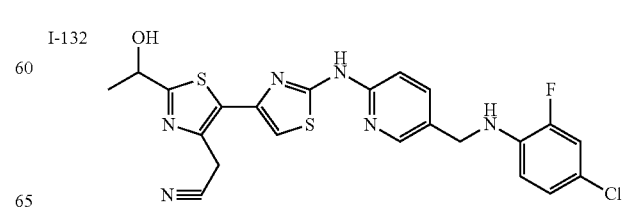

TABLE 1-continued
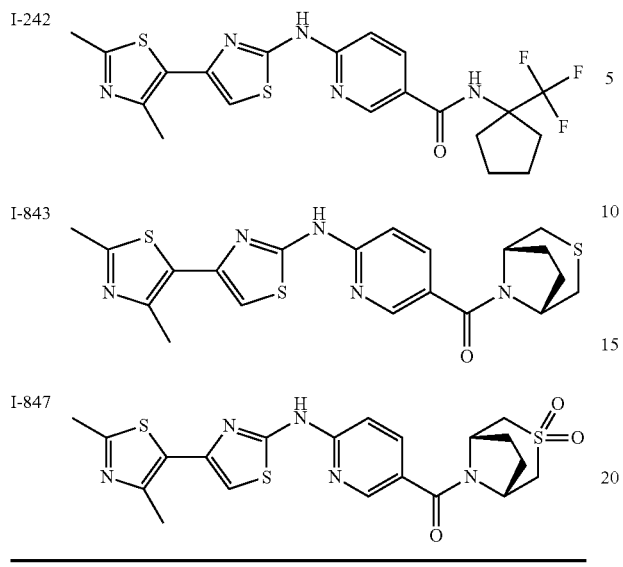
TABLE 2
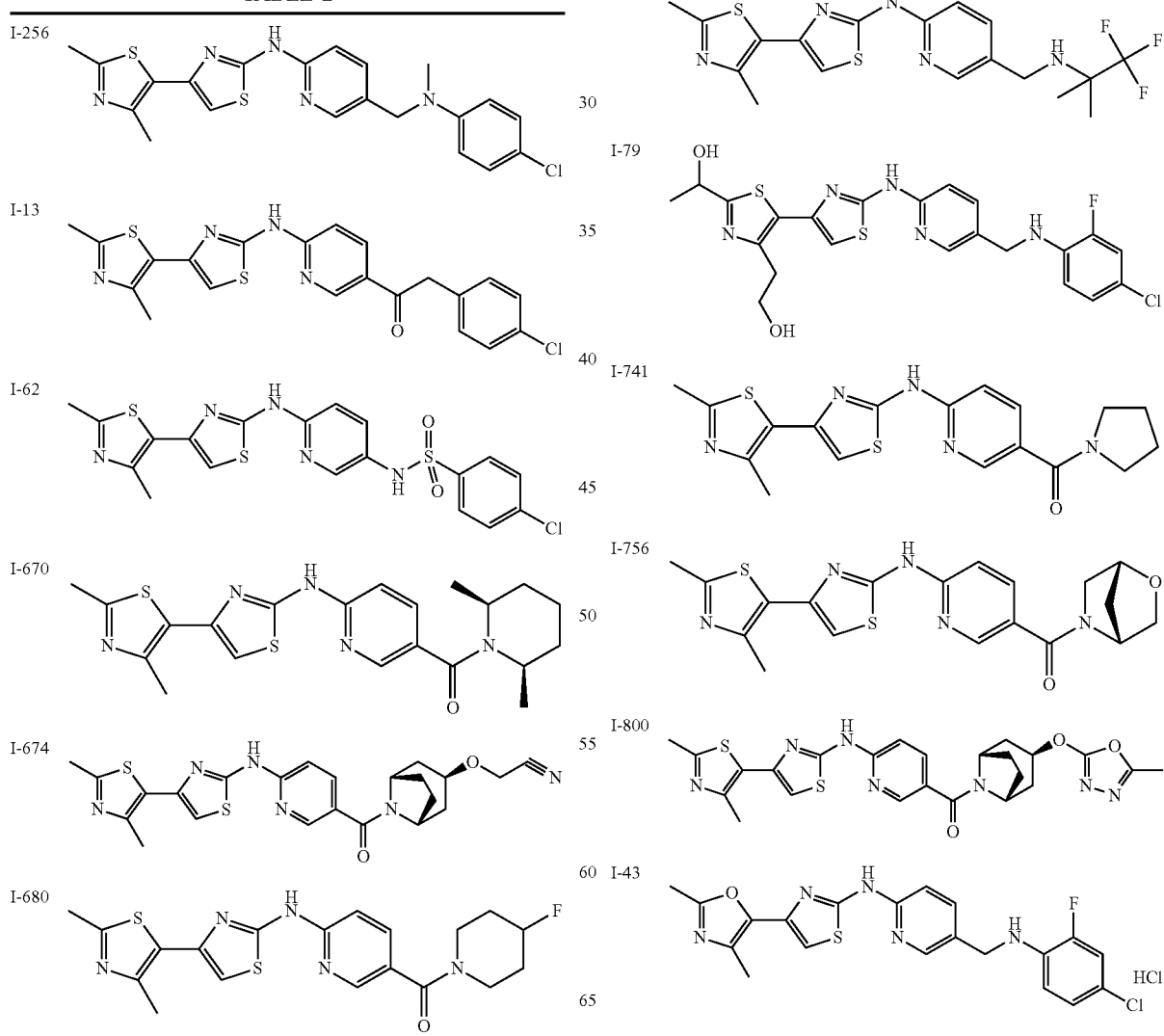
TABLE 2-continued
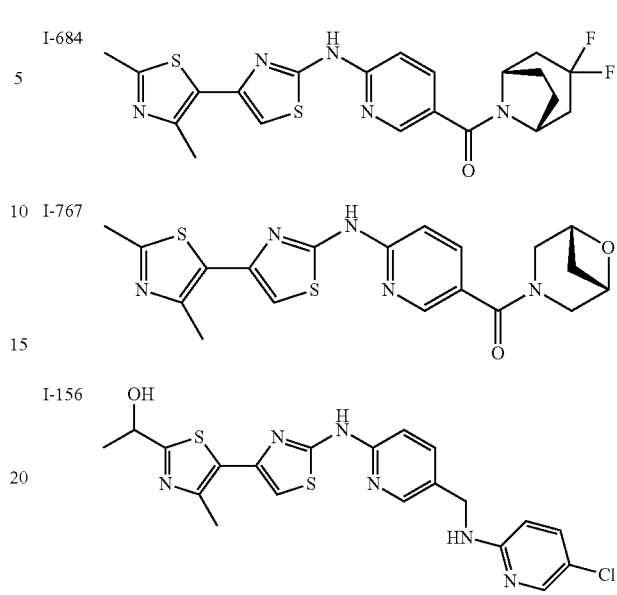

TABLE 2-continued
I-177 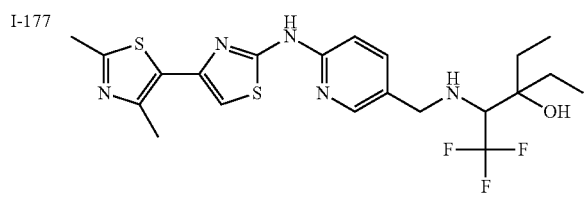
I-144 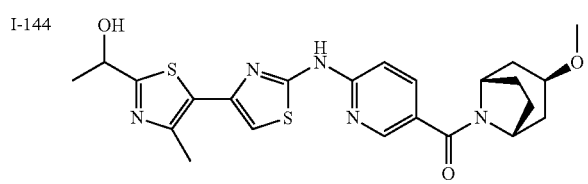
I-196 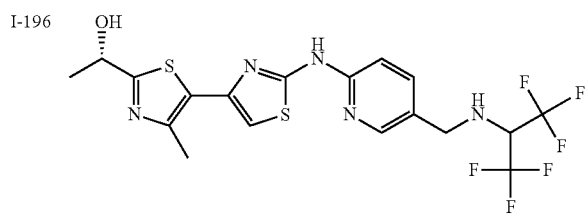
I-117 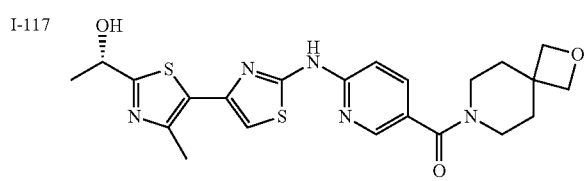
I-693 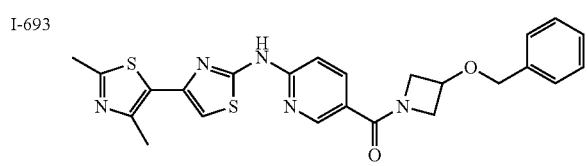
I-706 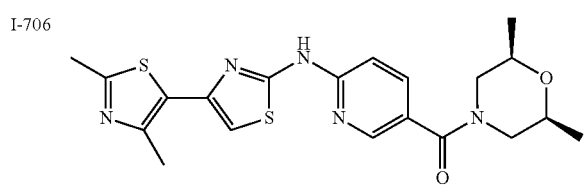
I-851 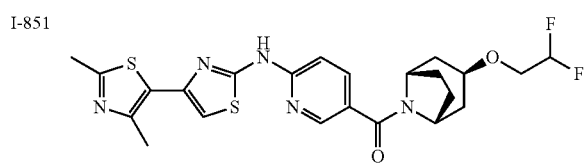
TABLE 3
I-303 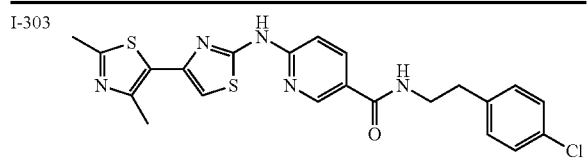
TABLE 3-continued
I-252 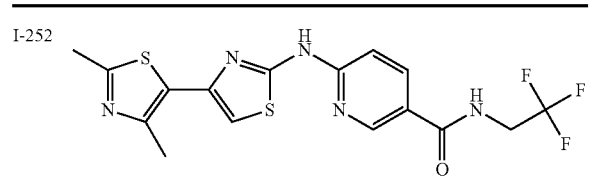
I-307 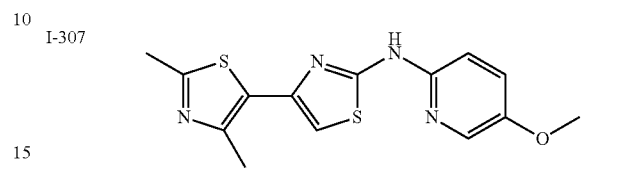
I-294 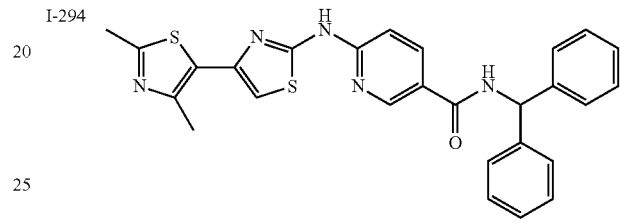
I-594 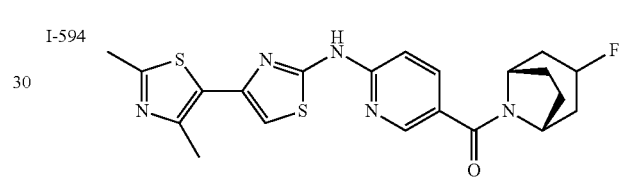
I-719 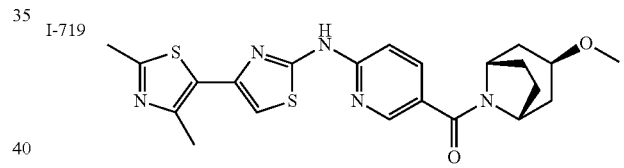
I-725 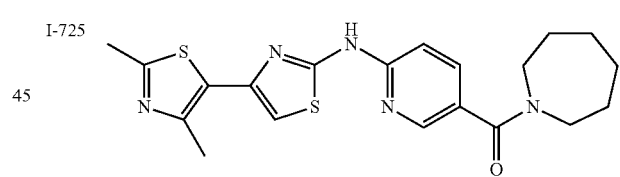
I-228 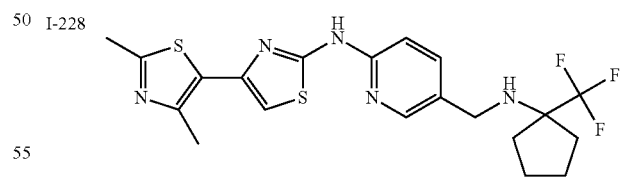
I-197 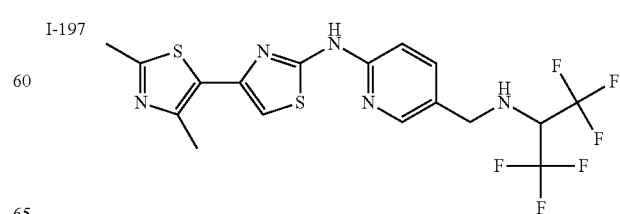

TABLE 3-continued

| ID | Structure |
|---|---|
| I-69 | 2-(1-hydroxyethyl)-4-(1,2-dihydroxyethyl)thiazole linked to thiazole-NH-pyridine-CH2NH-(4-chloro-2-fluorophenyl) |
| I-135 | 2-(1-hydroxyethyl)-4-methylthiazole linked to thiazole-NH-pyridine-C(O)NH-(4-cyanophenyl), HCl |
| I-185 | 2-(1-hydroxyethyl)-4-(cyanomethyl)thiazole linked to thiazole-NH-pyridine-CH2O-CH(CF3)2 |
| I-195 | 2,4-dimethylthiazole linked to thiazole-NH-pyridine-C(O)NH-CH(CN)-(2,3-dichlorophenyl) |
| I-74 | 2-(1-hydroxyethyl)-4-ethylthiazole linked to thiazole-NH-pyridine-CH2NH-(4-chloro-2-fluorophenyl) |
| I-113 | 2-(1-hydroxyethyl)-4-methylthiazole linked to thiazole-NH-pyridine-C(O)NH-(1-(trifluoromethyl)cyclopropyl), HCl |
| I-162 | 2-(1-hydroxyethyl)-4-methylthiazole linked to thiazole-NH-pyridine-C(O)-(4-piperidin-1-yl-piperidine) |
| I-163 | 2-(1-hydroxyethyl)thiazole-4-methyl linked to thiazole-NH-pyridine-C(O)-(4-morpholin-4-yl-piperidine) |
| I-269 | 2,4-dimethylthiazole linked to thiazole-NH-pyridine-C(O)-morpholine |
| I-270 | 2,4-dimethylthiazole linked to thiazole-NH-pyridine-C(O)NH-(4-phenoxyphenyl) |
| I-277 | 2,4-dimethylthiazole linked to thiazole-NH-pyridine-C(O)NH-(2-ethylphenyl) |

TABLE 4

| ID | Structure |
|---|---|
| I-302 | 2,4-dimethylthiazole linked to thiazole-NH-pyridine-C(O)NH-(tetrahydropyran-4-yl) |
| I-240 | 2,4-dimethylthiazole linked to thiazole-NH-pyridine-C(O)NH-(3,3-difluorocyclobutyl) |
| I-241 | 2-(1-hydroxyethyl)-4-methylthiazole linked to thiazole-NH-pyridine-C(O)NH-(4-chloro-2-fluorophenyl) |
| I-251 | 2,4-dimethylthiazole linked to thiazole-NH-pyridine-C(O)NH-(2-chlorophenyl) |

TABLE 4-continued
I-213
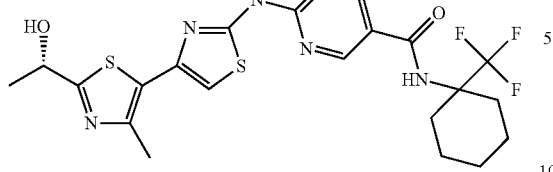
I-246
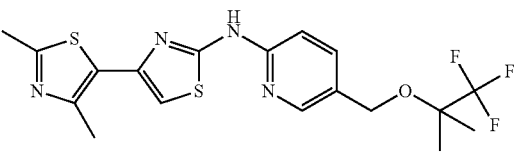 [SMILES: Cc1nc(C)c(-c2csc(Nc3ccc(COC(C)(C)C(F)(F)F)cn3)n2)s1]
I-55
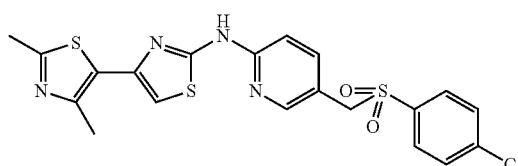
I-295
I-267
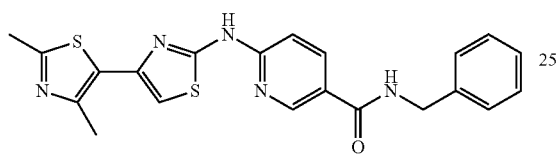
I-427
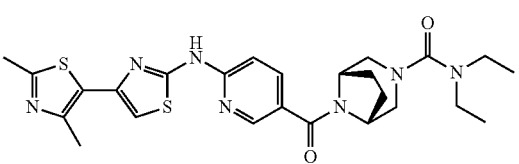 [SMILES: CCN(CC)C(=O)N1C[C@H]2CC[C@@H](C1)N2C(=O)c1ccc(Nc2nc(-c3sc(C)nc3C)cs2)nc1]
I-106
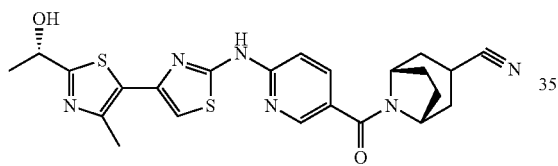
I-592
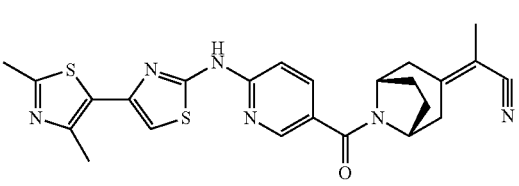 [SMILES: C/C(C#N)=C1/C[C@H]2CC[C@@H](C1)N2C(=O)c1ccc(Nc2nc(-c3sc(C)nc3C)cs2)nc1]
I-199
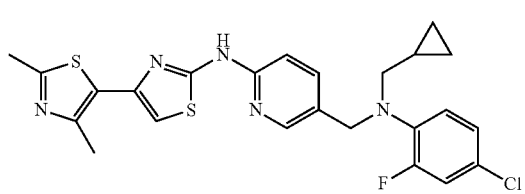
I-653
I-134
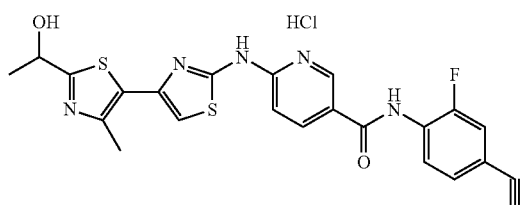
I-662
I-245
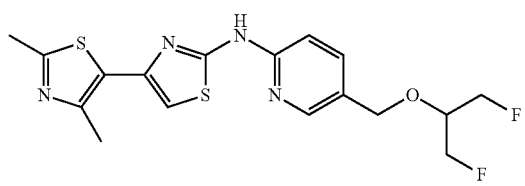
I-728
I-778
I-290

TABLE 4-continued
I-580 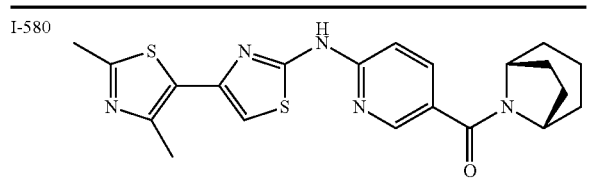
I-669 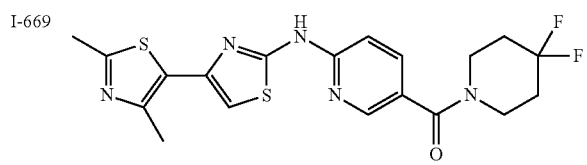
I-682 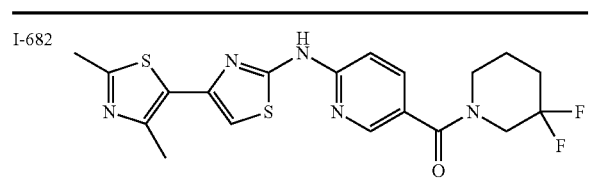
I-685 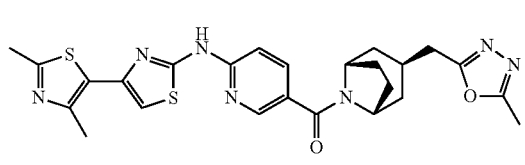
TABLE 5
I-54 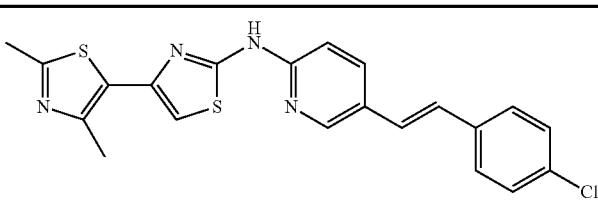
I-265 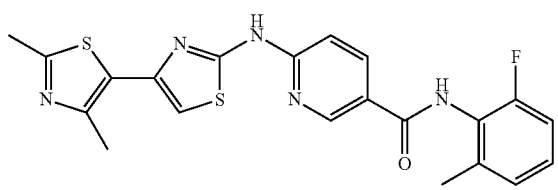 [SMILES: Cc1nc(C)c(-c2csc(Nc3ccc(C(=O)Nc4c(C)cccc4F)cn3)n2)s1]
I-304 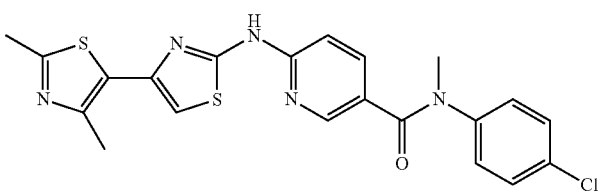 [SMILES: Cc1nc(C)c(-c2csc(Nc3ccc(C(=O)N(C)c4ccc(Cl)cc4)cn3)n2)s1]
I-309 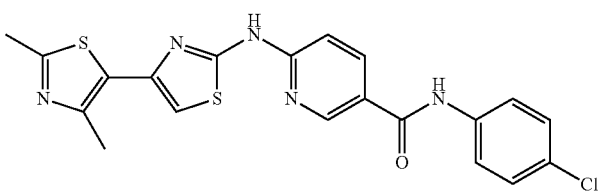 [SMILES: Cc1nc(C)c(-c2csc(Nc3ccc(C(=O)Nc4ccc(Cl)cc4)cn3)n2)s1]
I-95 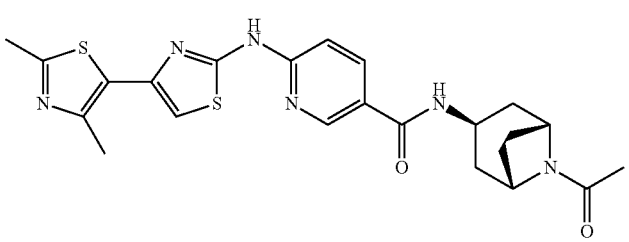 [SMILES: CC(=O)N1[C@@H]2CC[C@H]1C[C@@H](NC(=O)c1ccc(Nc3nc(-c4sc(C)nc4C)cs3)nc1)C2]
I-190 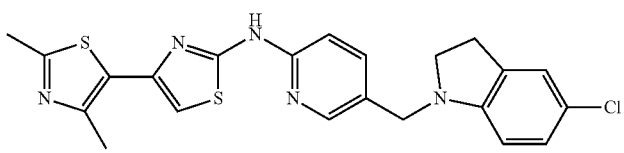 [SMILES: Cc1nc(C)c(-c2csc(Nc3ccc(CN4CCc5cc(Cl)ccc54)cn3)n2)s1]

TABLE 5-continued
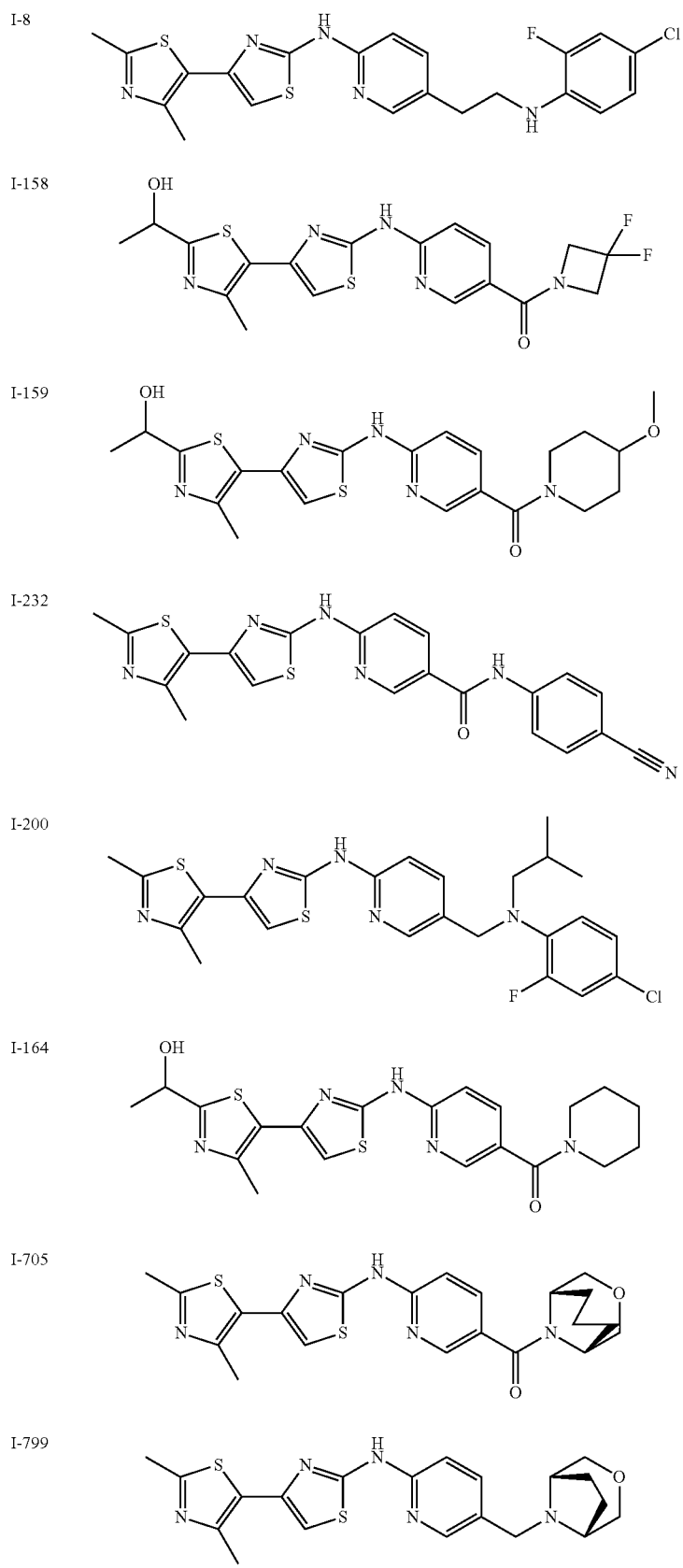

TABLE 5-continued
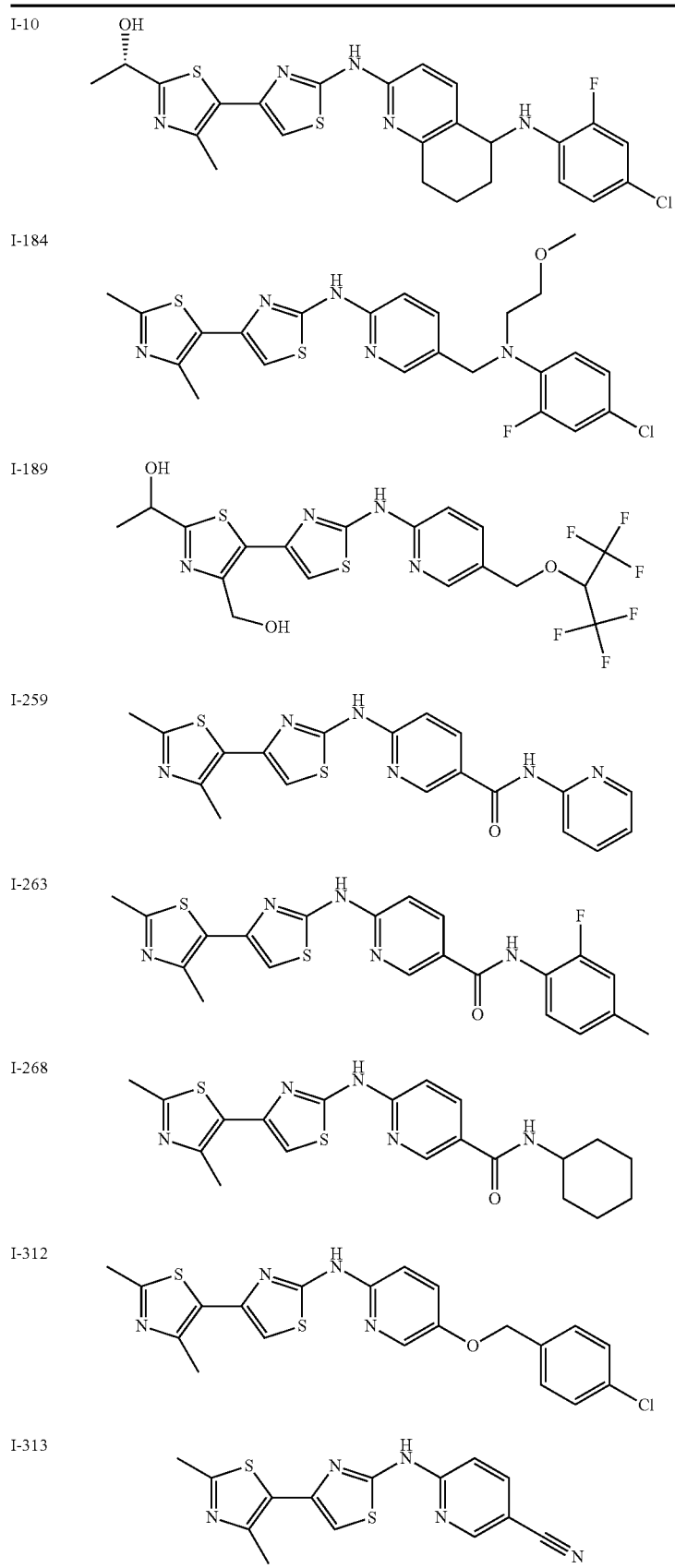

TABLE 5-continued
I-257 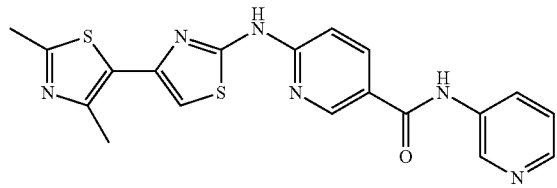 [SMILES: Cc1nc(C)c(-c2csc(Nc3ccc(C(=O)Nc4cccnc4)cn3)n2)s1]
I-53 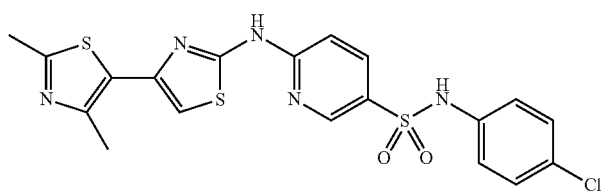 [SMILES: Cc1nc(C)c(-c2csc(Nc3ccc(S(=O)(=O)Nc4ccc(Cl)cc4)cn3)n2)s1]
TABLE 6
I-41 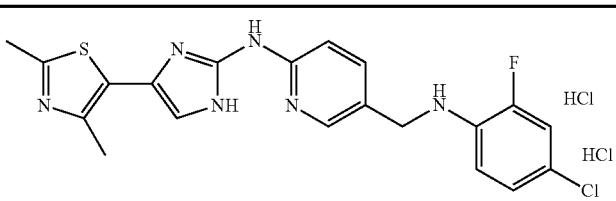
I-215 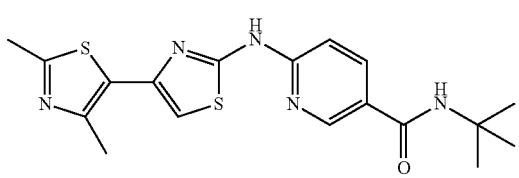 [SMILES: Cc1nc(C)c(-c2csc(Nc3ccc(C(=O)NC(C)(C)C)cn3)n2)s1]
I-258 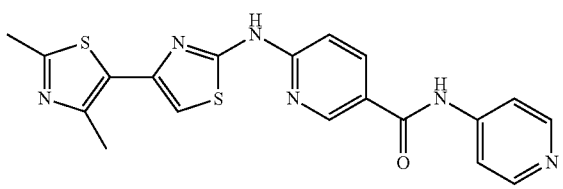 [SMILES: Cc1nc(C)c(-c2csc(Nc3ccc(C(=O)Nc4ccncc4)cn3)n2)s1]
I-827 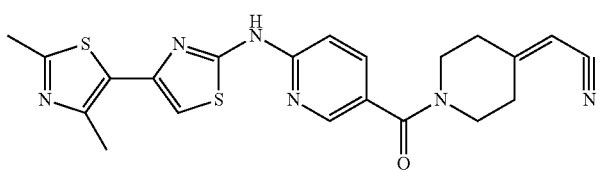 [SMILES: Cc1nc(C)c(-c2csc(Nc3ccc(C(=O)N4CCC(=CC#N)CC4)cn3)n2)s1]
I-830 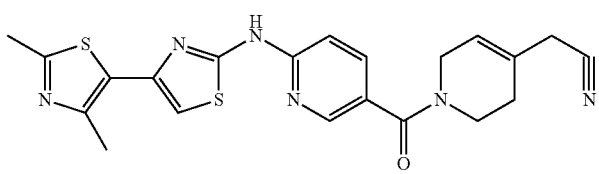 [SMILES: Cc1nc(C)c(-c2csc(Nc3ccc(C(=O)N4CC=C(CC#N)CC4)cn3)n2)s1]
I-686 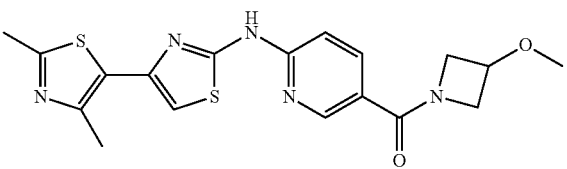

TABLE 6-continued
I-703 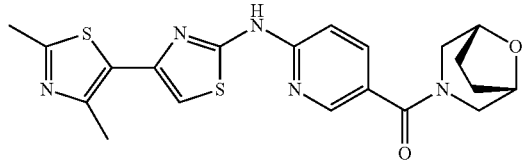 [SMILES: Cc1nc(C)c(-c2csc(Nc3ccc(C(=O)N4C[C@H]5CC[C@@H](C4)O5)cn3)n2)s1]
I-108 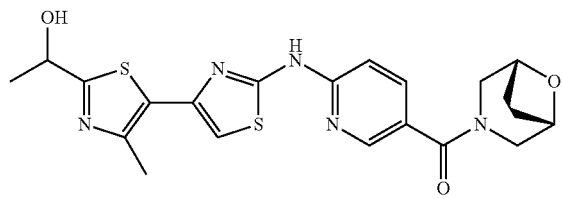 [SMILES: Cc1nc(C(C)O)sc1-c1csc(Nc2ccc(C(=O)N3C[C@H]4CC[C@@H](C3)O4)cn2)n1]
I-811 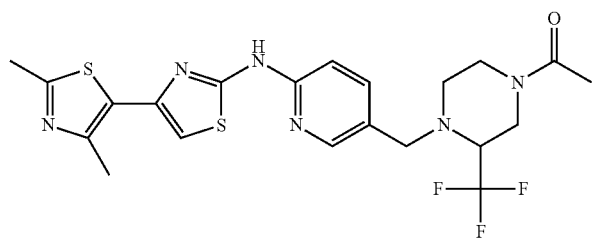 [SMILES: CC(=O)N1CCN(Cc2ccc(Nc3nc(-c4sc(C)nc4C)cs3)nc2)C(C(F)(F)F)C1]
I-118 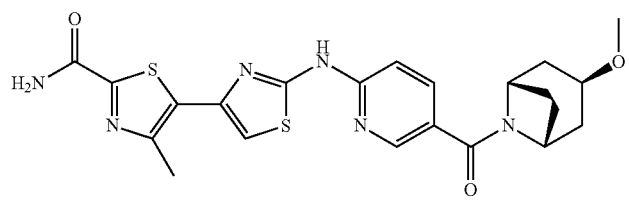 [SMILES: CO[C@H]1C[C@H]2CC[C@@H](C1)N2C(=O)c1ccc(Nc2nc(-c3sc(C(N)=O)nc3C)cs2)nc1]
I-151 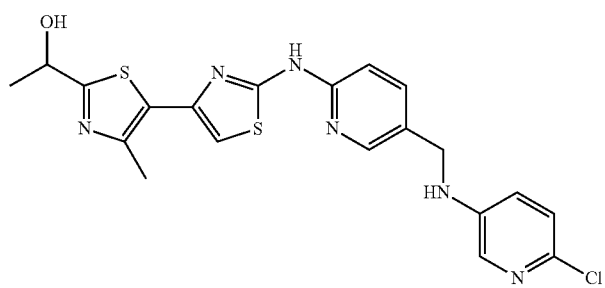 [SMILES: Cc1nc(C(C)O)sc1-c1csc(Nc2ccc(CNc3ccc(Cl)nc3)cn2)n1]
I-157 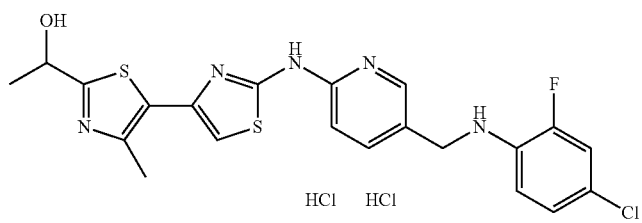 [SMILES: Cc1nc(C(C)O)sc1-c1csc(Nc2ccc(CNc3ccc(Cl)cc3F)cn2)n1 ; Cl ; Cl]
I-430 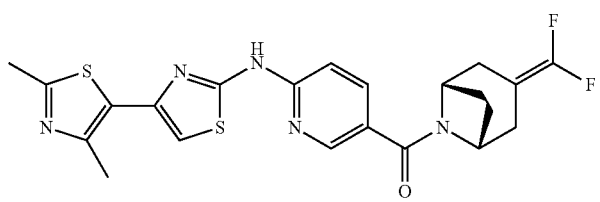 [SMILES: Cc1nc(C)c(-c2csc(Nc3ccc(C(=O)N4[C@@H]5CC[C@H]4CC(=C(F)F)C5)cn3)n2)s1]

TABLE 6-continued
I-296 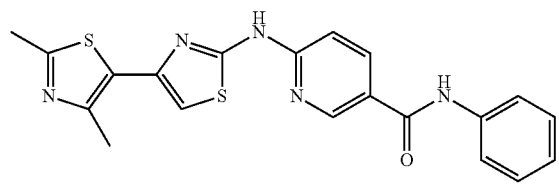 [SMILES: Cc1nc(C)c(-c2csc(Nc3ccc(C(=O)Nc4ccccc4)cn3)n2)s1]
I-298 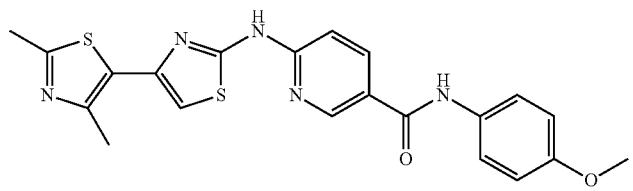
I-49 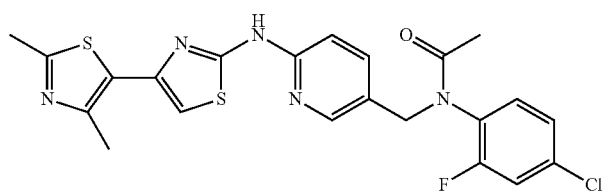 [SMILES: CC(=O)N(Cc1ccc(Nc2nc(-c3sc(C)nc3C)cs2)nc1)c1ccc(Cl)cc1F]
I-208 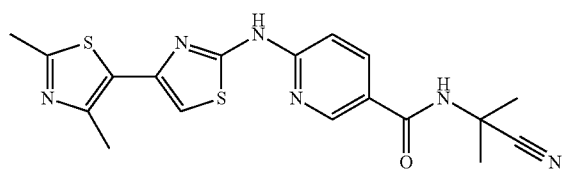 [SMILES: Cc1nc(C)c(-c2csc(Nc3ccc(C(=O)NC(C)(C)C#N)cn3)n2)s1]
I-209 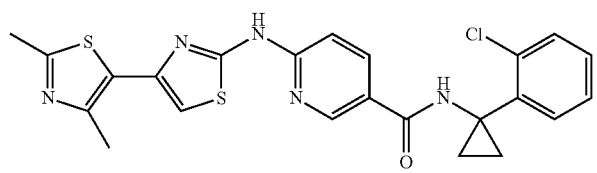 [SMILES: Cc1nc(C)c(-c2csc(Nc3ccc(C(=O)NC4(c5ccccc5Cl)CC4)cn3)n2)s1]
I-254 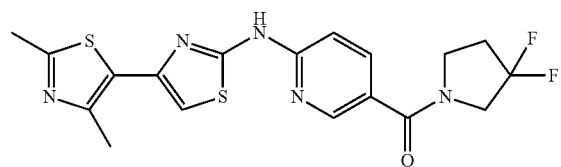 [SMILES: Cc1nc(C)c(-c2csc(Nc3ccc(C(=O)N4CCC(F)(F)C4)cn3)n2)s1]
I-212 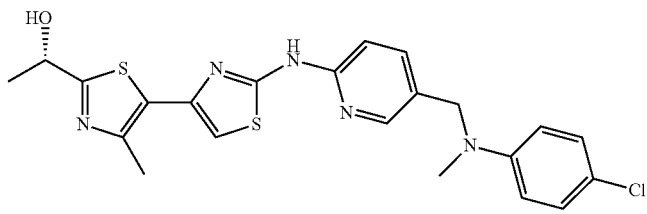 [SMILES: Cc1nc([C@H](C)O)sc1-c1csc(Nc2ccc(CN(C)c3ccc(Cl)cc3)cn2)n1]
I-393 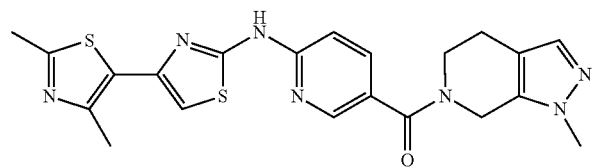 [SMILES: Cc1nc(C)c(-c2csc(Nc3ccc(C(=O)N4CCc5cnn(C)c5C4)cn3)n2)s1]

TABLE 6-continued
I-260 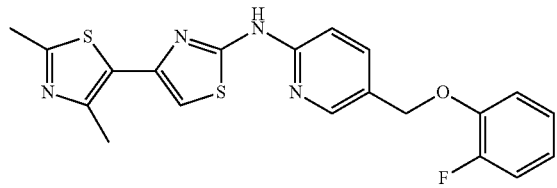 [SMILES: Cc1nc(C)c(-c2csc(Nc3ccc(COc4ccccc4F)cn3)n2)s1]
I-262 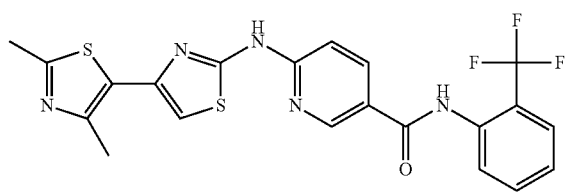 [SMILES: Cc1nc(C)c(-c2csc(Nc3ccc(C(=O)Nc4ccccc4C(F)(F)F)cn3)n2)s1]
I-271 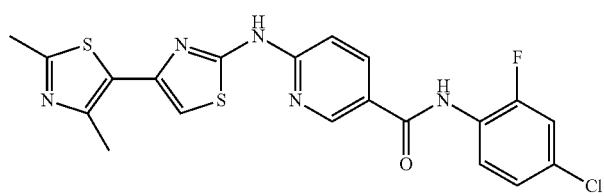 [SMILES: Cc1nc(C)c(-c2csc(Nc3ccc(C(=O)Nc4ccc(Cl)cc4F)cn3)n2)s1]
TABLE 7
I-227 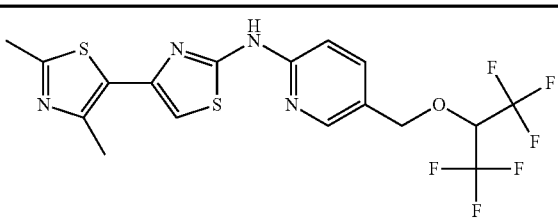
I-52 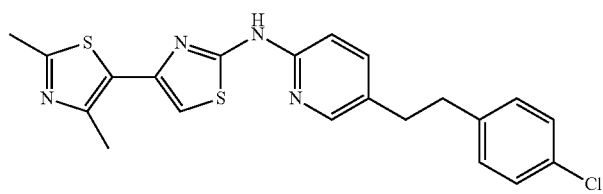 [SMILES: Cc1nc(C)c(-c2csc(Nc3ccc(CCc4ccc(Cl)cc4)cn3)n2)s1]
I-331 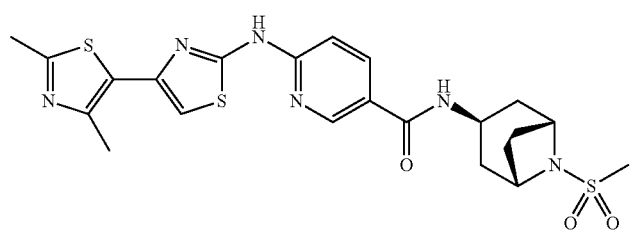
I-357 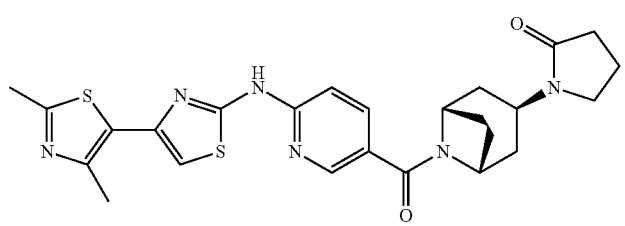 [SMILES: Cc1nc(C)c(-c2csc(Nc3ccc(C(=O)N4[C@@H]5CC[C@H]4C[C@@H](N4CCCC4=O)C5)cn3)n2)s1]

TABLE 7-continued
I-573 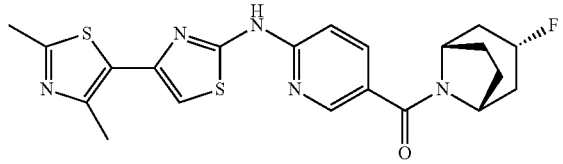 [SMILES: Cc1nc(C)c(-c2csc(Nc3ccc(C(=O)N4[C@@H]5CC[C@H]4C[C@H](F)C5)cn3)n2)s1]
I-831 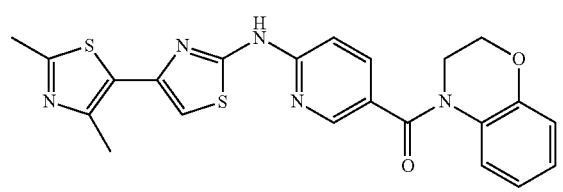 [SMILES: Cc1nc(C)c(-c2csc(Nc3ccc(C(=O)N4CCOc5ccccc54)cn3)n2)s1]
I-727 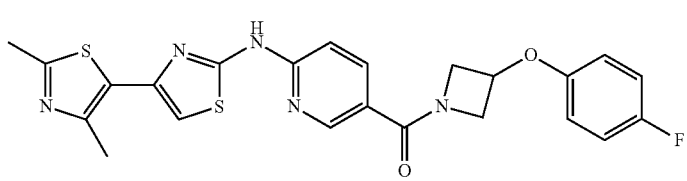 [SMILES: Cc1nc(C)c(-c2csc(Nc3ccc(C(=O)N4CC(Oc5ccc(F)cc5)C4)cn3)n2)s1]
I-735 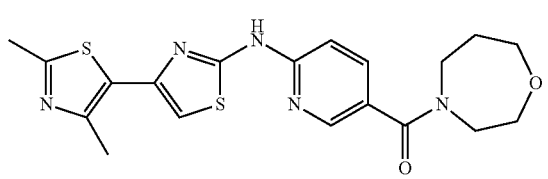 [SMILES: Cc1nc(C)c(-c2csc(Nc3ccc(C(=O)N4CCCOCC4)cn3)n2)s1]
I-845 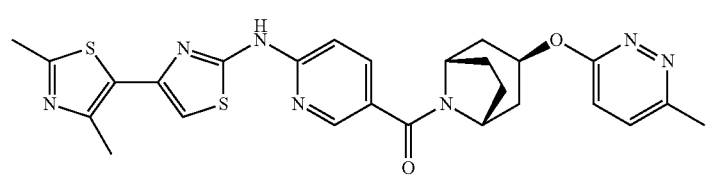
I-849 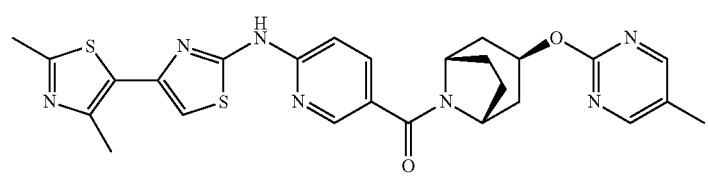
I-152 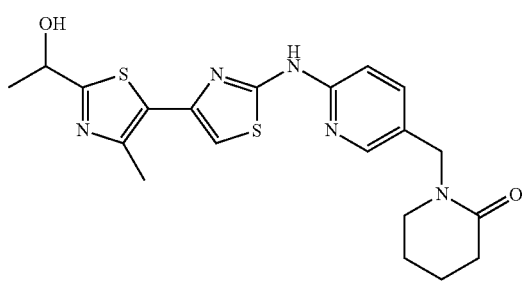 [SMILES: Cc1nc(C(C)O)sc1-c1csc(Nc2ccc(CN3CCCCC3=O)cn2)n1]
I-305 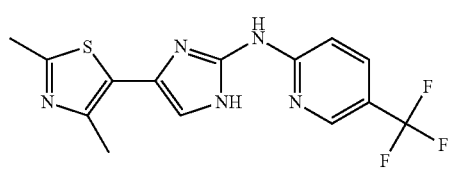 [SMILES: Cc1nc(C)c(-c2c[nH]c(Nc3ccc(C(F)(F)F)cn3)n2)s1]

TABLE 7-continued
I-155 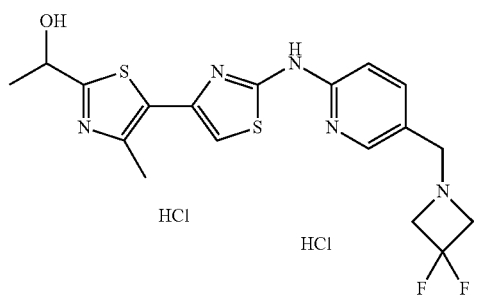 [SMILES: Cc1nc(C(C)O)sc1-c1csc(Nc2ccc(CN3CC(F)(F)C3)cn2)n1 ; Cl ; Cl]
I-224 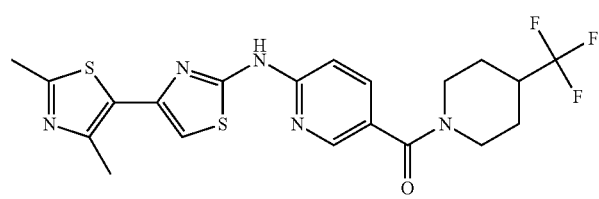 [SMILES: Cc1nc(C)c(-c2csc(Nc3ccc(C(=O)N4CCC(C(F)(F)F)CC4)cn3)n2)s1]
I-238 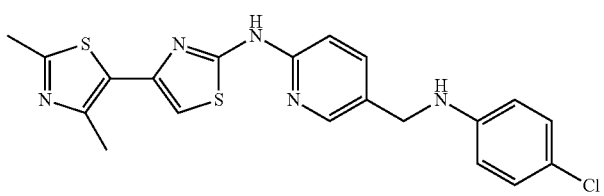 [SMILES: Cc1nc(C)c(-c2csc(Nc3ccc(CNc4ccc(Cl)cc4)cn3)n2)s1]
I-198 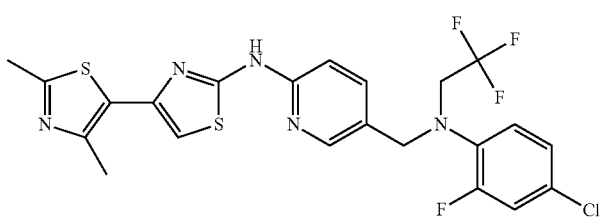 [SMILES: Cc1nc(C)c(-c2csc(Nc3ccc(CN(CC(F)(F)F)c4ccc(Cl)cc4F)cn3)n2)s1]
I-206 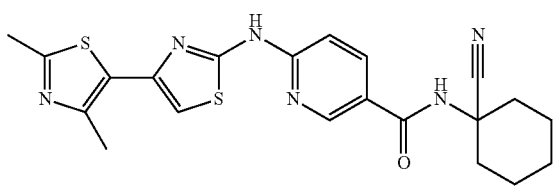 [SMILES: Cc1nc(C)c(-c2csc(Nc3ccc(C(=O)NC4(C#N)CCCCC4)cn3)n2)s1]
I-167 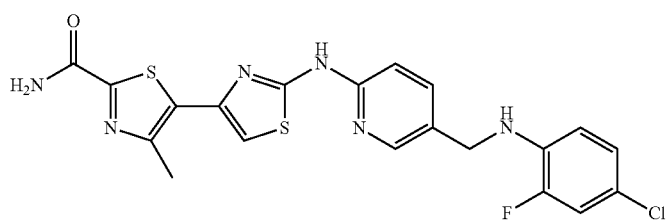 [SMILES: Cc1nc(C(N)=O)sc1-c1csc(Nc2ccc(CNc3ccc(Cl)cc3F)cn2)n1]
I-17 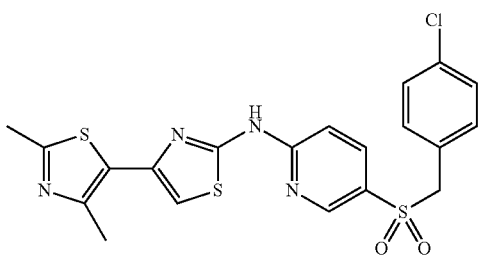 [SMILES: Cc1nc(C)c(-c2csc(Nc3ccc(S(=O)(=O)Cc4ccc(Cl)cc4)cn3)n2)s1]

TABLE 7-continued
I-250 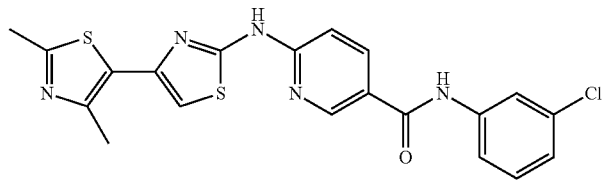 [SMILES: Cc1nc(C)c(-c2csc(Nc3ccc(C(=O)Nc4cccc(Cl)c4)cn3)n2)s1]
I-214 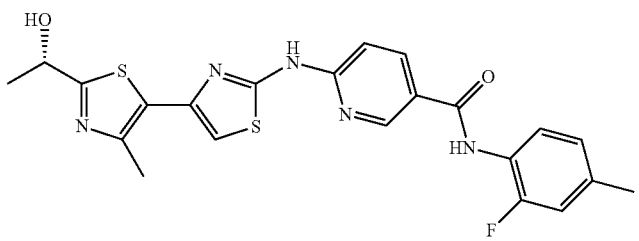 [SMILES: Cc1ccc(NC(=O)c2ccc(Nc3nc(-c4sc([C@H](C)O)nc4C)cs3)nc2)c(F)c1]
I-272 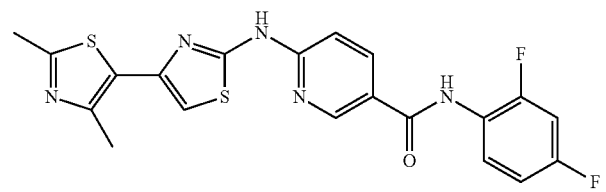 [SMILES: Cc1nc(C)c(-c2csc(Nc3ccc(C(=O)Nc4ccc(F)cc4F)cn3)n2)s1]
TABLE 8
I-278 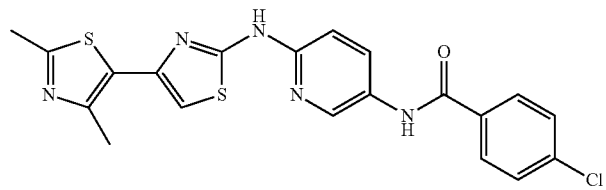 [SMILES: Cc1nc(C)c(-c2csc(Nc3ccc(NC(=O)c4ccc(Cl)cc4)cn3)n2)s1]
I-284 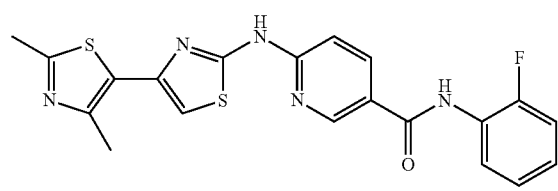 [SMILES: Cc1nc(C)c(-c2csc(Nc3ccc(C(=O)Nc4ccccc4F)cn3)n2)s1]
I-285 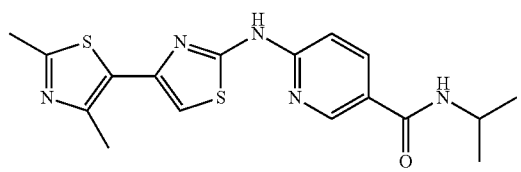 [SMILES: Cc1nc(C)c(-c2csc(Nc3ccc(C(=O)NC(C)C)cn3)n2)s1]
I-329 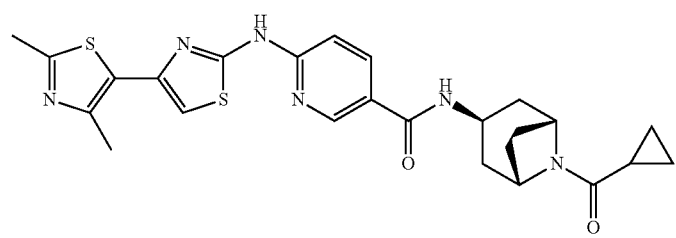 [SMILES: Cc1nc(C)c(-c2csc(Nc3ccc(C(=O)N[C@H]4C[C@H]5CC[C@@H](C4)N5C(=O)C4CC4)cn3)n2)s1]

TABLE 8-continued
I-629 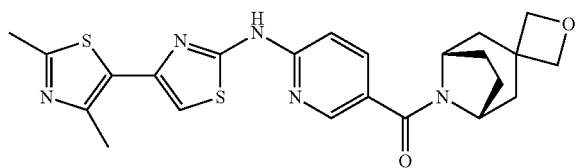 [SMILES: Cc1nc(C)c(-c2csc(Nc3ccc(C(=O)N4[C@@H]5CC[C@H]4CC4(COC4)C5)cn3)n2)s1]
I-638 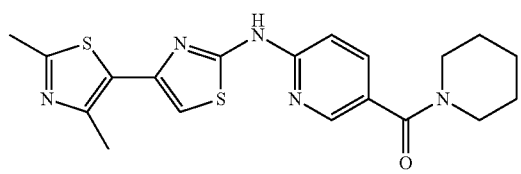 [SMILES: Cc1nc(C)c(-c2csc(Nc3ccc(C(=O)N4CCCCC4)cn3)n2)s1]
I-658 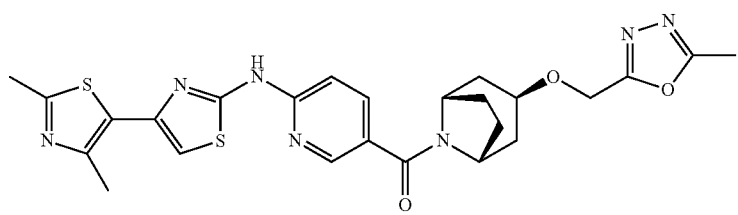
I-696 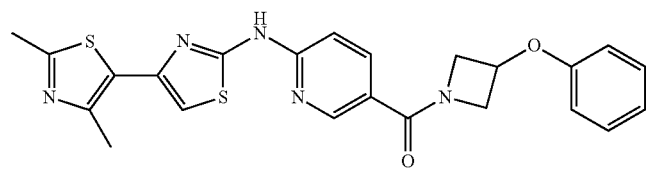 [SMILES: Cc1nc(C)c(-c2csc(Nc3ccc(C(=O)N4CC(Oc5ccccc5)C4)cn3)n2)s1]
I-850 
I-852 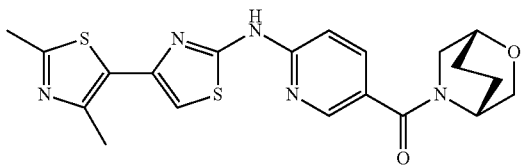 [SMILES: Cc1nc(C)c(-c2csc(Nc3ccc(C(=O)N4C[C@H]5CC[C@@H]4CO5)cn3)n2)s1]
I-315 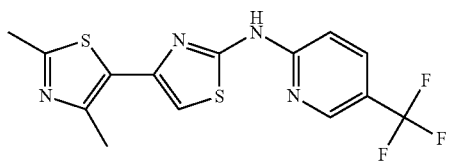 [SMILES: Cc1nc(C)c(-c2csc(Nc3ccc(C(F)(F)F)cn3)n2)s1]
I-274 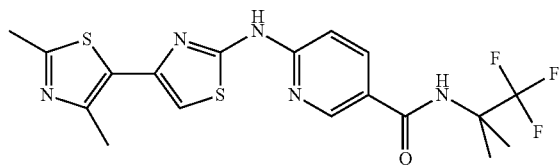 [SMILES: Cc1nc(C)c(-c2csc(Nc3ccc(C(=O)NC(C)(C)C(F)(F)F)cn3)n2)s1]
I-174 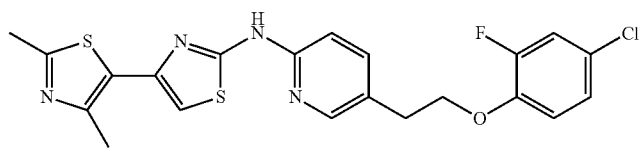 [SMILES: Cc1nc(C)c(-c2csc(Nc3ccc(CCOc4ccc(Cl)cc4F)cn3)n2)s1]

TABLE 8-continued
I-813
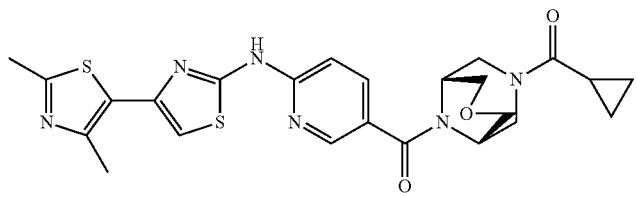 [SMILES: Cc1nc(C)c(-c2csc(Nc3ccc(C(=O)N4[C@@H]5COC[C@H]4CN(C(=O)C4CC4)C5)cn3)n2)s1]
I-188
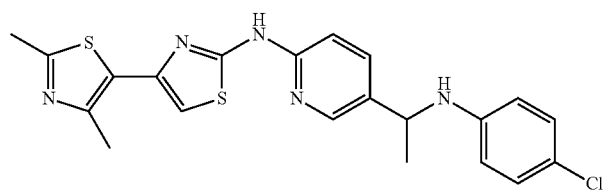 [SMILES: Cc1nc(C)c(-c2csc(Nc3ccc(C(C)Nc4ccc(Cl)cc4)cn3)n2)s1]
I-231
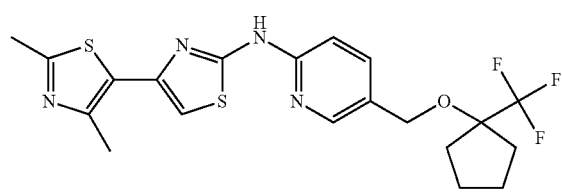 [SMILES: Cc1nc(C)c(-c2csc(Nc3ccc(COC4(C(F)(F)F)CCCC4)cn3)n2)s1]
I-48
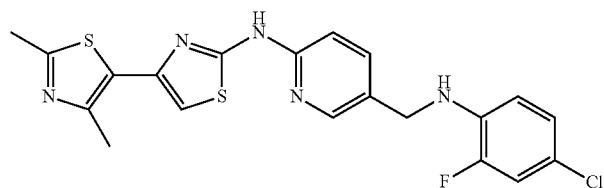 [SMILES: Cc1nc(C)c(-c2csc(Nc3ccc(CNc4ccc(Cl)cc4F)cn3)n2)s1]
I-205
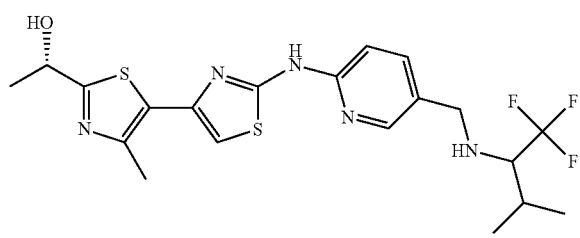
I-207
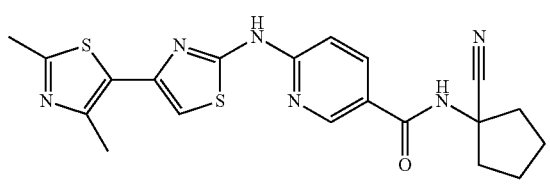 [SMILES: Cc1nc(C)c(-c2csc(Nc3ccc(C(=O)NC4(C#N)CCCC4)cn3)n2)s1]
I-166
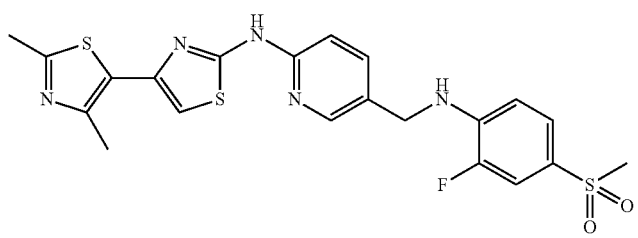 [SMILES: Cc1nc(C)c(-c2csc(Nc3ccc(CNc4ccc(S(C)(=O)=O)cc4F)cn3)n2)s1]

TABLE 8-continued
I-168 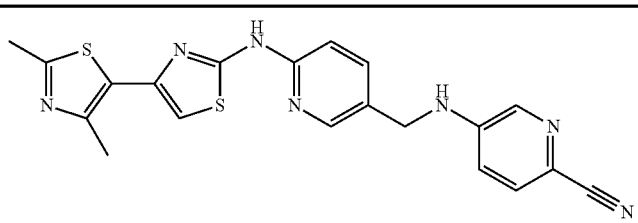
I-306 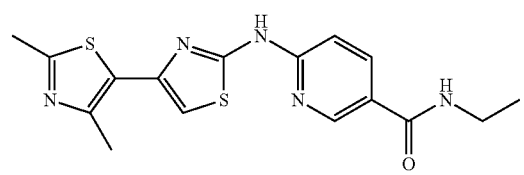
I-920 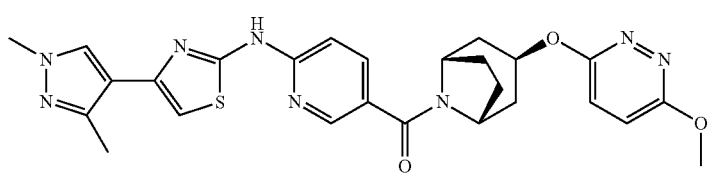
I-1046 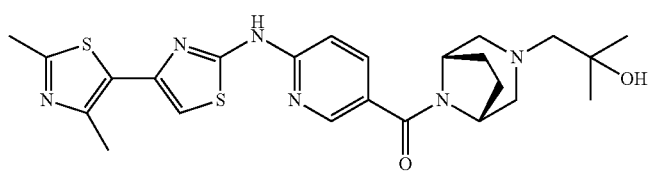 [SMILES: Cc1nc(C)c(-c2csc(Nc3ccc(C(=O)N4[C@@H]5CC[C@H]4CN(CC(C)(C)O)C5)cn3)n2)s1]
TABLE 9
I-275 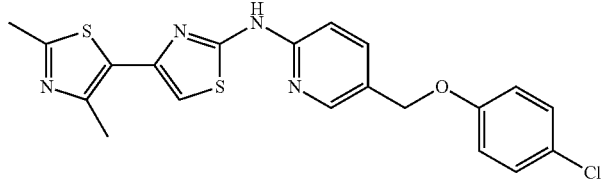 [SMILES: Cc1nc(C)c(-c2csc(Nc3ccc(COc4ccc(Cl)cc4)cn3)n2)s1]
I-276 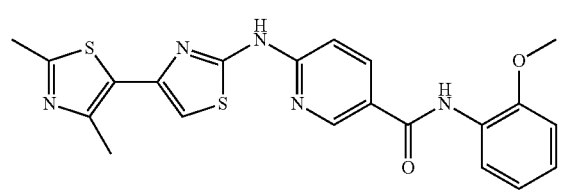
I-283 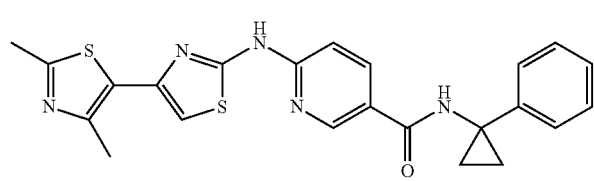 [SMILES: Cc1nc(C)c(-c2csc(Nc3ccc(C(=O)NC4(c5ccccc5)CC4)cn3)n2)s1]
I-292 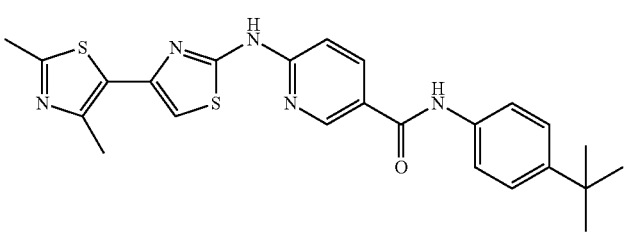 [SMILES: Cc1nc(C)c(-c2csc(Nc3ccc(C(=O)Nc4ccc(C(C)(C)C)cc4)cn3)n2)s1]

TABLE 9-continued
I-297 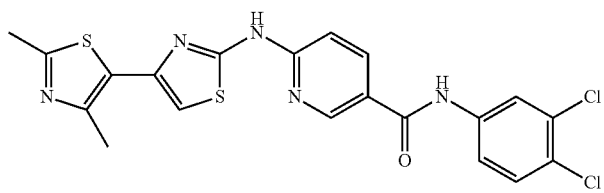 [SMILES: Cc1nc(C)c(-c2csc(Nc3ccc(C(=O)Nc4ccc(Cl)c(Cl)c4)cn3)n2)s1]
I-457 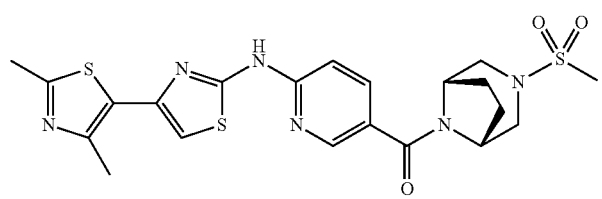
I-897 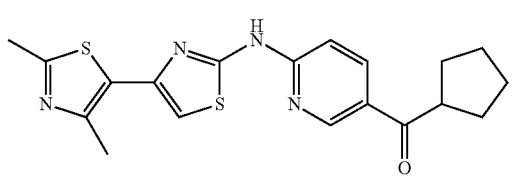 [SMILES: Cc1nc(C)c(-c2csc(Nc3ccc(C(=O)C4CCCC4)cn3)n2)s1]
I-913 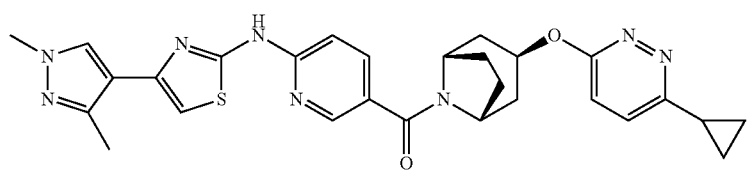 [SMILES: Cc1nn(C)cc1-c1csc(Nc2ccc(C(=O)N3[C@@H]4CC[C@H]3C[C@@H](Oc3ccc(C5CC5)nn3)C4)cn2)n1]
I-918 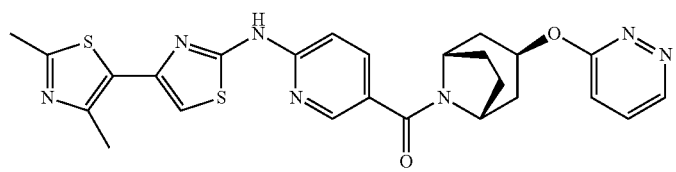 [SMILES: Cc1nc(C)c(-c2csc(Nc3ccc(C(=O)N4[C@@H]5CC[C@H]4C[C@@H](Oc4cccnn4)C5)cn3)n2)s1]
I-899 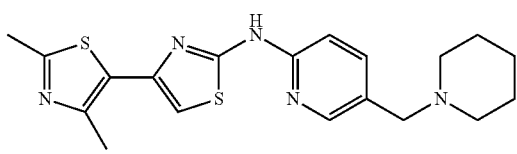 [SMILES: Cc1nc(C)c(-c2csc(Nc3ccc(CN4CCCCC4)cn3)n2)s1]
I-927 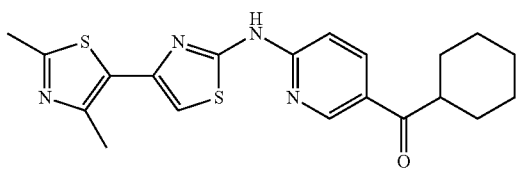 [SMILES: Cc1nc(C)c(-c2csc(Nc3ccc(C(=O)C4CCCCC4)cn3)n2)s1]
I-945 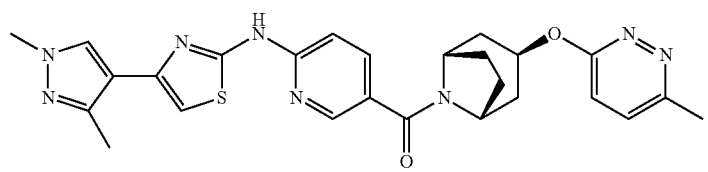
I-919 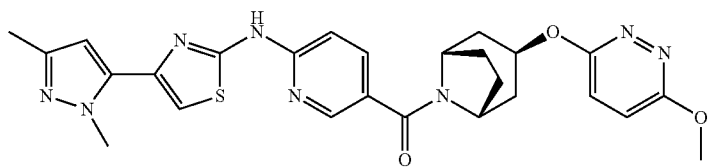

TABLE 9-continued

I-1048
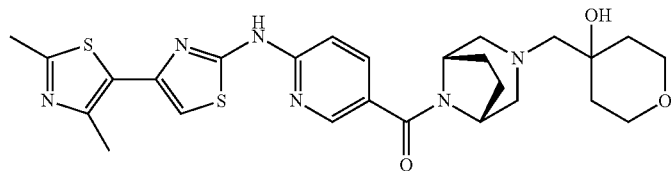 [SMILES: Cc1nc(C)c(-c2csc(Nc3ccc(C(=O)N4[C@@H]5CC[C@H]4CN(CC4(O)CCOCC4)C5)cn3)n2)s1]

I-1017
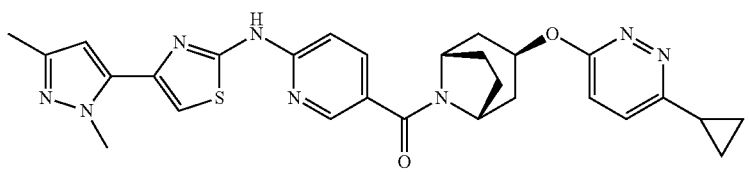 [SMILES: Cc1cc(-c2csc(Nc3ccc(C(=O)N4[C@@H]5CC[C@H]4C[C@@H](Oc4ccc(C6CC6)nn4)C5)cn3)n2)n(C)n1]

I-901
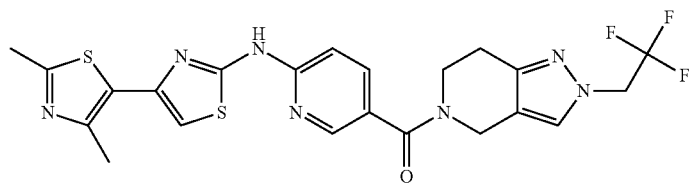 [SMILES: Cc1nc(C)c(-c2csc(Nc3ccc(C(=O)N4CCc5nn(CC(F)(F)F)cc5C4)cn3)n2)s1]

The physical properties (LC/MS data) of Compounds are described below.

TABLE 10

| No. | [M + H] | RT (min) | LC/MS method | No. | [M + H] | RT (min) | LC/MS method |
|---|---|---|---|---|---|---|---|
| I-485 | 474.2 | 1.85 | 5 | I-190 | 455.1 | 2.65 | 1 |
| I-564 | 463.2 | 1.76 | 5 | I-8 | 460.1 | 2.54 | 1 |
| I-726 | 414.1 | 1.33 | 1 | I-158 | 438.1 | 1.59 | 1 |
| I-731 | 372.9 | 2.27 | 1 | I-159 | 460.1 | 1.50 | 1 |
| I-744 | 446.1 | 1.64 | 1 | I-232 | 433.0 | 1.95 | 1 |
| I-175 | 443.1 | 2.57 | 1 | I-200 | 502.2 | 3.05 | 1 |
| I-176 | 437.1 | 2.02 | 1 | I-164 | 430.1 | 1.68 | 1 |
| I-764 | 408.0 | 1.68 | 1 | I-41 | 429.2 | 1.74 | 1 |
| I-140 | 403.0 | 2.14 | 1 | I-215 | 388.1 | 1.86 | 1 |
| I-141 | 456.1 | 1.78 | 1 | I-258 | 408.9 | 1.13 | 1 |
| I-187 | 442.1 | 1.60 | 1 | I-259 | 408.9 | 1.26 | 1 |
| I-45 | 499.1 | 2.17 | 1 | I-263 | 440.1 | 2.05 | 1 |
| I-150 | 490.1 | 2.37 | 1 | I-268 | 414.0 | 2.00 | 1 |
| I-6 | 491.1 | 2.37 | 1 | I-312 | 429.0 | 2.50 | 1 |
| I-226 | 468.1 | 2.76 | 1 | I-313 | 314.0 | 1.77 | 1 |
| I-203 | 458.1 | 1.59 | 5 | I-257 | 408.9 | 1.66 | 1 |
| I-204 | 473.1 | 2.46 | 5 | I-53 | 476.1 | 2.12 | 1 |
| I-96 | 486.2 | 1.57 | 1 | I-430 | 474.2 | 2.15 | 5 |
| I-132 | 501.1 | 2.29 | 1 | I-296 | 408.0 | 1.94 | 1 |
| I-242 | 468.1 | 2.13 | 1 | I-298 | 438.0 | 1.90 | 1 |
| I-248 | 482.1 | 2.25 | 1 | I-827 | 437.2 | 1.67 | 5 |
| I-308 | 456.0 | 2.03 | 1 | I-830 | 437.2 | 1.88 | 5 |
| I-256 | 442.1 | 2.55 | 1 | I-686 | 402.1 | 1.46 | 1 |
| I-13 | 441.0 | 2.38 | 1 | I-703 | 428.1 | 1.49 | 1 |
| I-62 | 477.0 | 1.99 | 1 | I-108 | 458.2 | 1.74 | 5 |
| I-670 | 428.2 | 2.02 | 1 | I-811 | 497.1 | 1.80 | 1 |
| I-674 | 481.2 | 1.72 | 1 | I-118 | 485.1 | 1.75 | 1 |
| I-680 | 418.1 | 1.63 | 1 | I-151 | 459.1 | 1.77 | 1 |
| I-684 | 462.1 | 1.90 | 1 | I-157 | 476.0 | 2.60 | 5 |
| I-767 | 414.1 | 1.32 | 1 | I-227 | 469.1 | 2.32 | 1 |
| I-843 | 444.0 | 1.81 | 1 | I-49 | 488.1 | 2.10 | 1 |
| I-847 | 476.1 | 1.42 | 1 | I-208 | 399.1 | 1.59 | 1 |
| I-741 | 386.0 | 1.57 | 1 | I-209 | 482.1 | 2.12 | 1 |
| I-756 | 414.0 | 1.33 | 1 | I-254 | 422.1 | 1.69 | 1 |
| I-800 | 524.2 | 1.62 | 1 | I-212 | 472.0 | 2.43 | 5 |
| I-43 | 430.1 | 2.40 | 1 | I-393 | 452.3 | 1.43 | 5 |

TABLE 11

| No. | [M + H] | RT (min) | LC/MS method | No. | [M + H] | RT (min) | LC/MS method |
|---|---|---|---|---|---|---|---|
| I-177 | 486.2 | 2.29 | 1 | I-260 | 413.1 | 2.27 | 1 |
| I-144 | 486.2 | 1.73 | 1 | I-262 | 476.1 | 2.02 | 1 |
| I-196 | 498.1 | 2.09 | 1 | I-271 | 459.0 | 2.17 | 1 |
| I-117 | 472.2 | 1.37 | 1 | I-305 | 340.0 | 1.14 | 1 |
| I-156 | 459.1 | 1.78 | 1 | I-52 | 427.1 | 2.60 | 1 |
| I-236 | 428.1 | 1.96 | 1 | I-331 | 520.3 | 1.50 | 5 |
| I-79 | 506.1 | 2.05 | 1 | I-357 | 509.2 | 1.57 | 1 |
| I-303 | 470.0 | 2.08 | 1 | I-573 | 444.2 | 1.76 | 5 |
| I-252 | 414.3 | 1.75 | 1 | I-831 | 450.1 | 1.96 | 1 |
| I-307 | 319.0 | 1.77 | 1 | I-727 | 482.1 | 2.00 | 1 |
| I-294 | 498.0 | 2.23 | 1 | I-735 | 416.1 | 1.41 | 1 |
| I-594 | 444.2 | 1.85 | 5 | I-845 | 534.2 | 1.56 | 1 |
| I-719 | 456.1 | 1.82 | 1 | I-849 | 534.2 | 1.80 | 1 |
| I-725 | 414.1 | 1.87 | 1 | I-152 | 430.1 | 1.48 | 1 |
| I-693 | 478.1 | 1.95 | 1 | I-155 | 424.1 | 1.19 | 1 |
| I-706 | 430.1 | 1.67 | 1 | I-224 | 468.1 | 1.93 | 1 |
| I-851 | 506.2 | 1.99 | 1 | I-238 | 428.0 | 2.30 | 1 |
| I-135 | 463.1 | 1.84 | 5 | I-198 | 528.1 | 2.66 | 1 |
| I-185 | 524.1 | 2.18 | 1 | I-206 | 439.1 | 1.89 | 1 |
| I-195 | 515.1 | 2.19 | 1 | I-167 | 455.1 | 2.14 | 1 |
| I-74 | 490.1 | 2.41 | 1 | I-17 | 477.0 | 2.12 | 1 |
| I-113 | 470.1 | 1.70 | 1 | I-250 | 441.9 | 2.22 | 1 |
| I-162 | 513.2 | 0.98 | 1 | I-214 | 470.1 | 2.02 | 5 |
| I-163 | 515.2 | 0.90 | 1 | I-272 | 443.1 | 1.94 | 1 |
| I-228 | 454.1 | 2.43 | 1 | I-278 | 441.1 | 2.04 | 1 |
| I-197 | 468.1 | 2.24 | 1 | I-284 | 425.0 | 1.92 | 1 |
| I-69 | 522.1 | 1.96 |  | I-285 | 374.0 | 1.61 | 1 |
| I-302 | 416.0 | 1.41 | 1 | I-329 | 510.3 | 1.58 | 5 |
| I-240 | 422.1 | 1.73 | 1 | I-629 | 468.2 | 1.55 | 1 |
| I-241 | 490.0 | 2.03 | 1 | I-638 | 400.1 | 1.79 | 1 |
| I-251 | 441.9 | 2.15 | 1 | I-658 | 538.2 | 1.58 | 1 |
| I-213 | 512.1 | 2.17 | 5 | I-696 | 464.1 | 1.98 | 1 |
| I-55 | 477.0 | 1.98 | 1 | I-850 | 488.2 | 1.88 | 1 |
| I-267 | 422.0 | 1.87 | 1 | I-852 | 428.1 | 1.43 | 1 |
| I-269 | 402.0 | 1.43 | 1 | I-174 | 497.1 | 2.14 | 1 |
| I-270 | 500.1 | 2.37 | 1 | I-813 | 511.3 | 1.43 | 5 |

TABLE 12

| No. | [M + H] | RT (min) | LC/MS method | No. | [M + H] | RT (min) | LC/MS method |
|---|---|---|---|---|---|---|---|
| I-277 | 435.1 | 2.00 | 1 | I-188 | 442.1 | 2.36 | 1 |
| I-295 | 422.0 | 2.06 | 1 | I-231 | 455.1 | 2.58 | 1 |
| I-427 | 466.3 | 1.66 | 5 | I-48 | 446.1 | 2.42 | 1 |
| I-592 | 526.2 | 1.78 | 1 | I-205 | 472.1 | 2.23 | 5 |
| I-653 | 477.3 | 1.88 | 5 | I-207 | 425.1 | 1.76 | 1 |
| I-662 | 428.1 | 1.52 | 1 | I-166 | 490.1 | 1.77 | 1 |
| I-728 | 500.1 | 2.02 | 1 | I-168 | 447.1 | 2.35 | 1 |
| I-778 | 450.0 | 1.32 | 1 | I-306 | 360.0 | 1.46 | 1 |
| I-106 | 481.2 | 1.51 | 1 | I-315 | 357.0 | 2.27 | 1 |
| I-199 | 500.1 | 2.90 | 1 | I-274 | 422.1 | 1.98 | 1 |
| I-134 | 481.1 | 1.85 | 5 | I-275 | 429.1 | 2.50 | 1 |
| I-245 | 397.1 | 1.86 | 1 | I-276 | 437.1 | 2.04 | 1 |
| I-246 | 429.1 | 2.34 | 1 | I-283 | 507.0 | 2.18 | 1 |
| I-54 | 425.1 | 2.75 | 1 | I-292 | 464.0 | 2.44 | 1 |
| I-265 | 440.1 | 1.86 | 1 | I-297 | 476.0 | 2.39 | 1 |
| I-304 | 456.0 | 2.02 | 1 | I-457 | 505.1 | 1.53 | 1 |
| I-309 | 442.0 | 2.16 | 1 | I-897 | 385.1 | 2.35 | 1 |
| I-95 | 483.3 | 1.40 | 5 | I-913 | 543.2 | 1.66 | 1 |
| I-290 | 476.0 | 2.29 | 1 | I-920 | 533.2 | 1.72 | 1 |
| I-580 | 426.1 | 1.88 | 1 | I-1046 | 499.2 | 1.16 | 1 |
| I-669 | 436.1 | 1.77 | 1 | I-918 | 520.2 | 1.60 | 1 |
| I-681 | 436.1 | 1.74 | 1 | I-899 | 386.0 | 1.14 | 1 |
| I-685 | 522.3 | 1.55 | 5 | I-927 | 399.1 | 2.48 | 1 |
| I-705 | 442.1 | 1.69 | 1 | I-945 | 517.2 | 1.42 | 1 |
| I-799 | 414.1 | 1.01 | 1 | I-919 | 533.2 | 1.83 | 1 |
| I-10 | 516.1 | 2.64 | 1 | I-1048 | 541.2 | 1.19 | 1 |
| I-184 | 504.2 | 2.59 | 1 | I-1017 | 543.3 | 1.76 | 1 |
| I-189 | 515.3 | 2.02 | 1 | I-901 | 520.1 | 1.67 | 1 |

NMR spectra were indicated in the following tables.

TABLE 13

| | NMR |
|---|---|
| I-485 | 1H-NMR (CDCl3) δ: 1.58-1.71 (m, 5H), 2.08-2.10 (br m, 3H), 2.61 (s, 3H), 2.67 (s, 3H), 4.23 (s, 1H), 4.44 (dd, J = 47.3, 7.0 Hz, 2H), 4.83 (s, 1H), 5.30 (s, 1H), 6.81 (d, J = 8.5 Hz, 1H), 6.84 (s, 1H), 7.79 (dd, J = 8.5, 2.1 Hz, 1H), 8.53 (d, J = 1.8 Hz, 1H), 8.83 (s, 1H). |
| I-564 | 1H-NMR (CDCl3) δ: 1.60 (s, 3H), 1.65-1.74 (m, 2H), 2.08 (br s, 2H), 2.33-2.36 (m, 1H), 2.61 (s, 3H), 2.66 (s, 3H), 2.86-2.88 (m, 2H), 5.34 (s, 1H), 6.80 (d, J = 8.5 Hz, 1H), 6.85 (s, 1H), 7.80 (dd, J = 8.5, 2.1 Hz, 1H), 8.56 (d, J = 1.9 Hz, 1H), 8.95 (s, 1H). |
| I-45 | 1H-NMR (CDCl3) δ: 1.64 (d, J = 6.4 Hz, 3H), 2.62 (s, 3H), 2.89 (s, 1H), 4.12-4.18 (m, 1H), 4.84 (s, 2H), 5.10 (q, J = 6.4 Hz, 1H), 6.84-6.86 (m, 2H), 7.66 (d, J = 8.5 Hz, 1H), 8.35 (s, 1H). |
| I-6 | 1H-NMR (CDCl3) δ: 1.63 (d, J = 6.5 Hz, 3H), 2.60 (s, 3H), 3.08 (t, J = 6.1 Hz, 2H), 4.19 (t, J = 6.1 Hz, 2H), 5.10 (q, J = 6.4 Hz, 1H), 6.84 (dd, J = 16.3, 7.5 Hz, 2H), 7.06 (dd, J = 30.1, 9.8 Hz, 3H), 7.65 (d, J = 8.0 Hz, 1H), 8.27 (s, 1H). |
| I-96 | 1H-NMR (DMSO-D6) δ: 1.26-1.58 (m, 5H), 1.64-1.77 (m, 2H), 1.81-2.11 (m, 4H), 2.54 (s, 3H), 3.22 (s, 3H), 3.65-3.77 (m, 1H), 4.09-4.29 (br, 1H), 4.51-4.67 (br, 1H), 4.83-4.93 (m, 1H), 6.04 (d, J = 5.0 Hz, 1H), 7.10-7.19 (m, 2H), 7.85 (dd, J = 8.7, 2.1 Hz, 1H), 8.44 (d, J = 2.0 Hz, 1H), 11.72 (s, 1H). |
| I-132 | 1H-NMR (DMSO-D6) δ: 1.47 (d, J = 6.5 Hz, 3H), 4.30 (d, J = 6.5 Hz, 2H), 4.43-4.51 (m, 2H), 4.88-4.97 (m, 1H), 6.21 (d, J = 5.0 Hz, 1H), 6.32-6.39 (m, 1H), 6.68 (t, J = 9.2 Hz, 1H), 6.97 (d, J = 8.8 Hz, 1H), 7.06 (d, J = 8.5 Hz, 1H), 7.19 (dd, J = 11.7, 2.4 Hz, 1H), 7.22 (s, 1H), 7.72 (dd, J = 8.5, 2.3 Hz, 1H), 8.29-8.33 (m, 1H), 11.44 (s, 1H). |
| I-248 | 1H-NMR (DMSO-d6) δ: 1.19-1.31 (m, 1H), 1.38-1.51 (m, 4H), 1.58-1.70 (m, 3H), 2.53 (s, 3H), 2.60 (s, 3H), 2.69-2.79 (m, 2H), 7.12 (d, J = 8.8 Hz, 1H), 7.18 (s, 1H), 7.98 (s, 1H), 8.08 (d, J = 8.7 Hz, 1H), 8.82 (s, 1H), 11.9 (s, 1H). |
| I-13 | 1H-NMR (DMSO-D6) δ: 2.53 (s, 3H), 2.60 (s, 3H), 4.41 (s, 2H), 7.16 (d, J = 8.8 Hz, 1H), 7.22 (s, 1H), 7.28-7.33 (m, 2H), 7.36-7.41 (m, 2H), 8.23 (dd, J = 8.7, 2.4 Hz, 1H), 9.09 (d, J = 2.0 Hz, 1H), 12.04 (s, 1H). |
| I-62 | 1H-NMR (CDCl3) δ: 2.58 (s, 3H), 2.65 (s, 3H), 6.57 (br s, 1H), 6.76-6.78 (m, 2H), 7.44-7.46 (m, 3H), 7.65-7.68 (m, 1H), 7.96 (d, J = 2.5 Hz, 1H), 8.59 (br s, 1H). |

TABLE 13-continued

| | NMR |
|---|---|
| I-43 | 1H-NMR (DMSO-D6 + CD3OD) δ: 2.39 (s, 3H), 2.41 (s, 3H), 4.29 (s, 2H), 6.68 (t, J = 9.1 Hz, 1H), 6.97 (d, J = 8.7 Hz, 1H), 7.06 (d, J = 4.8 Hz, 2H), 7.20 (d, J = 11.8 Hz, 1H), 7.72 (d, J = 8.4 Hz, 1H), 8.30 (s, 1H). |
| I-79 | 1H-NMR (DMSO-D6) δ: 1.44 (d, J = 6.5 Hz, 3H), 3.04-3.08 (m, 2H), 3.75 (dd, J = 12.5, 6.8 Hz, 2H), 4.29 (d, J = 6.3 Hz, 2H), 4.71 (t, J = 5.5 Hz, 1H), 4.83-4.92 (m, 1H), 6.03 (d, J = 5.0 Hz, 1H), 6.32-6.38 (m, 1H), 6.68 (t, J = 9.2 Hz, 1H), 6.95-6.99 (m, 1H), 7.05 (d, J = 8.3 Hz, 1H), 7.15-7.21 (m, 2H), 7.71 (dd, J = 8.4, 2.1 Hz, 1H), 8.29-8.32 (m, 1H), 11.40 (s, 1H) |
| I-594 | 1H-NMR (CDCl3) δ: 2.06-2.08 (m, 4H), 2.19 (d, J = 7.5 Hz, 4H), 2.60 (s, 3H), 2.68 (s, 3H), 4.23 (br s, 1H), 4.81 (br s, 1H), 4.94 (d, J = 47.4 Hz, 1H), 6.83 (s, 1H), 6.86 (d, J = 8.7 Hz, 1H), 7.79 (dd, J = 8.5, 2.2 Hz, 1H), 8.52 (d, J = 1.9 Hz, 1H), 8.95 (br s, 1H). |
| I-135 | 1H-NMR (DMSO-D6) δ: 1.46 (d, J = 6.5 Hz, 3H), 2.55 (s, 3H), 4.89 (q, J = 6.4 Hz, 1H), 7.21 (s, 1H), 7.83 (d, J = 8.5 Hz, 2H), 8.00 (d, J = 8.8 Hz, 2H), 8.24 (dd, J = 8.7, 2.4 Hz, 1H), 8.99 (d, J = 2.0 Hz, 1H), 10.64 (s, 1H), 11.93 (s, 1H). |
| I-185 | 1H-NMR (CDCl3) δ: 1.66 (d, J = 6.4 Hz, 3H), 2.73 (d, J = 3.8 Hz, 1H), 4.13-4.19 (m, 1H), 4.29 (s, 2H), 4.85 (s, 2H), 5.11-5.13 (m, 1H), 6.91 (d, J = 7.9 Hz, 2H), 7.71 (d, J = 7.9 Hz, 1H), 8.31 (s, 1H), 8.36 (s, 1H). |

TABLE 14

| | NMR |
|---|---|
| I-74 | 1H-NMR (DMSO-D6) δ: 1.25 (dd, J = 9.5, 5.3 Hz, 3H), 1.46 (d, J = 6.5 Hz, 3H), 2.93 (ddd, J = 14.9, 7.5, 2.6 Hz, 2H), 4.20-4.45 (m, 2H), 4.91-4.95 (m, 1H), 6.69 (t, J = 9.2 Hz, 1H), 6.97 (dq, J = 8.7, 1.1 Hz, 1H), 7.07-7.13 (m, 2H), 7.19 (dd, J = 11.7, 2.4 Hz, 1H), 7.74 (d, J = 8.8 Hz, 1H), 8.29-8.33 (m, 1H), 11.54 (s, 1H) |
| I-197 | 1H-NMR (DMSO-d6) δ: 2.52 (s, 3H), 2.59 (s, 3H), 3.79-3.86 (m, 1H), 3.91 (d, J = 5.8 Hz, 2H), 4.63-4.75 (m, 1H), 7.06 (d, J = 8.3 Hz, 1H), 7.07 (s, 1H), 7.69 (dd, J = 8.5, 2.3 Hz, 1H), 8.24 (d, J = 1.8 Hz, 1H), 11.5 (s, 1H). |
| I-69 | 1H-NMR (DMSO-D6) δ: 1.46 (d, J = 6.5 Hz, 3H), 3.65-3.80 (m, 2H), 4.30 (s, 2H), 4.87-4.94 (m, 2H), 6.69 (t, J = 9.2 Hz, 1H), 6.95-6.99 (m, 1H), 7.07 (d, J = 8.5 Hz, 1H), 7.19 (dd, J = 11.5, 2.3 Hz, 1H), 7.26 (d, J = 4.5 Hz, 1H), 7.73 (dd, J = 8.5, 2.3 Hz, 1H), 8.30-8.32 (m, 1H), |
| I-241 | 1H-NMR (DMSO-D6) δ: 1.46 (d, J = 6.5 Hz, 3H), 2.55 (s, 3H), 4.89 (t, J = 5.6 Hz, 1H), 6.11 (d, J = 5.0 Hz, 1H), 7.19 (d, J = 9.0 Hz, 1H), 7.20 (s, 1H), 7.34 (d, J = 7.8 Hz, 1H), 7.55 (d, J = 9.5 Hz, 1H), 7.67 (t, J = 8.7 Hz, 1H), 8.23 (d, J = 8.5 Hz, 1H), 8.95 (s, 1H), 10.23 (s, 1H). |
| I-55 | 1H-NMR (DMSO-d6) δ: 2.52 (s, 3H), 2.59 (s, 3H), 4.72 (s, 2H), 7.01 (d, J = 8.7 Hz, 1H), 7.11 (s, 1H), 7.48 (d, J = 8.5 Hz, 1H), 7.71 (d, J = 8.7 Hz, 2H), 7.74 (d, J = 8.7 Hz, 2H), 8.06 (s, 1H). |
| I-427 | 1H-NMR (CDCl3) δ: 1.50 (dd, J = 13.4, 5.9 Hz, 1H), 1.58 (s, 3H), 1.76 (t, J = 11.4 Hz, 2H), 2.14 (t, J = 7.0 Hz, 2H), 2.32 (s, 1H), 2.52 (d, J = 7.4 Hz, 2H), 2.61 (s, 3H), 2.66 (s, 3H), 4.26 (br s, 1H), 4.84 (br s, 1H), 6.80 (d, J = 8.5 Hz, 1H), 6.84 (s, 1H), 7.78 (dd, J = 8.5, 2.2 Hz, 1H), 8.52 (t, J = 3.5 Hz, 1H), 8.81 (s, 1H). |
| I-653 | 1H-NMR (CDCl3) δ: 1.57 (s, 1H), 1.70 (s, 1H), 1.93 (s, 3H), 2.05 (s, 2H), 2.38 (s, 3H), 2.61 (d, J = 4.4 Hz, 3H), 2.68 (d, J = 4.4 Hz, 3H), 2.86 (s, 1H), 4.45 (br s, 1H), 4.86 (br s, 1H), 6.82 (d, J = 4.3 Hz, 1H), 7.13 (d, J = 3.8 Hz, 1H), 7.76 (s, 1H), 8.53 (s, 1H), 10.98 (s, 1H). |
| I-134 | 1H-NMR (DMSO-D6) δ: 1.46 (d, J = 6.5 Hz, 3H), 2.55 (s, 3H), 4.89 (q, J = 6.4 Hz, 1H), 7.20 (t, J = 6.7 Hz, 2H), 7.74 (d, J = 8.3 Hz, 1H), 7.95-8.03 (m, 2H), 8.23 (d, J = 8.8 Hz, 1H), 8.96 (s, 1H), 10.46 (s, 1H), 11.94 (s, 1H). |
| I-54 | 1H-NMR (DMSO-D6) δ: 2.53 (s, 3H), 2.60 (s, 3H), 7.09-7.13 (m, 2H), 7.21 (d, J = 16.3 Hz, 1H), 7.27 (d, J = 16.3 Hz, 1H), 7.44 (d, J = 8.5 Hz, 2H), 7.60 (d, J = 8.5 Hz, 2H), 8.05 (dd, J = 8.8, 2.3 Hz, 1H), 8.48 (d, J = 2.3 Hz, 1H), 11.6 (s, 1H). |
| I-95 | 1H-NMR (DMSO-D6) δ: 1.44 (s, 1H), 1.49 (s, 1H), 1.92-1.98 (m, 1H), 2.02-2.11 (m, 1H), 2.18-2.33 (m, 2H), 2.56 (d, J = 28.7 |

TABLE 14-continued

| | NMR |
|---|---|
| | Hz, 3H), 4.02 (s, 1H), 4.40 (s, 1H), 4.57 (d, J = 7.4 Hz, 1H), 7.13 (dd, J = 8.7, 3.8 Hz, 2H), 7.16 (s, 2H), 8.07 (dd, J = 8.7, 2.4 Hz, 1H), 8.27 (d, J = 3.9 Hz, 1H), 8.29 (s, 1H), 8.75 (d, J = 2.1 Hz, 1H), 11.80 (s, 1H). |
| I-685 | 1H-NMR (CDCl3) δ: 1.28-1.33 (m, 4H), 1.48 (s, 2H), 1.82 (s, 2H), 1.92 (s, 3H), 1.98-2.04 (m, 2H), 2.61 (s, 3H), 2.67 (s, 3H), 4.07 (t, J = 6.3 Hz, 1H), 4.18 (s, 1H), 4.83 (s, 1H), 6.84 (d, J = 6.4 Hz, 2H), 7.81 (d, J = 7.9 Hz, 1H), 8.52 (s, 1H), 8.65 (s, 1H). |
| I-10 | 1H-NMR (CDCl3) δ: 1.64 (d, J = 6.0 Hz, 3H), 1.94 (d, J = 32.8 Hz, 4H), 2.62 (s, 3H), 2.99 (t, J = 22.4 Hz, 3H), 4.03 (d, J = 8.2 Hz, 1H), 4.60 (s, 1H), 5.10 (s, 1H), 6.62 (d, J = 8.0 Hz, 1H), 6.78 (dd, J = 22.1, 13.5 Hz, 2H), 7.02 (d, J = 12.7 Hz, 2H), 7.60 (d, J = 7.5 Hz, |
| I-189 | 1H-NMR (CDCl3) δ: 1.26 (s, 1H), 1.66 (d, J = 6.4 Hz, 3H), 2.94 (s, 1H), 4.14-4.16 (m, 1H), 4.84 (s, 2H), 4.94 (s, 2H), 5.12 (q, J = 6.2 Hz, 1H), 6.88 (s, 1H), 6.98 (d, J = 8.5 Hz, 1H), 7.68 (d, J = 8.5 Hz, 1H), 8.33 (s, 1H), 10.15 (s, 1H). |
| I-8 | 1H-NMR (CDCl3) δ: 2.63 (d, J = 22.8 Hz, 6H), 2.89 (t, J = 7.0 Hz, 2H), 3.40 (d, J = 5.8 Hz, 2H), 3.91 (s, 1H), 6.62 (t, J = 8.9 Hz, 1H), 6.77 (t, J = 7.0 Hz, 2H), 6.99 (d, J = 9.3 Hz, 2H), 7.45 (d, J = 8.3 Hz, 1H), 8.23 (s, 1H), 8.53 (s, 1H). |

TABLE 15

| | NMR |
|---|---|
| I-41 | 1H-NMR (DMSO-D6 + CD3OD) δ: 2.40 (s, 3H), 2.68 (s, 3H), 4.37 (s, 2H), 6.66 (t, J = 9.0 Hz, 1H), 6.96 (d, J = 9.0 Hz, 1H), 7.22 (t, J = 9.0 Hz, 2H), 7.34 (s, 1H), 7.86 (d, J = 8.8 Hz, 1H). |
| I-53 | 1H-NMR (DMSO-d6) δ: 2.50 (s, 3H), 2.58 (s, 3H), 7.10-7.16 (m, 3H), 7.20 (s, 1H), 7.32 (d, J = 8.8 Hz, 2H), 7.96 (dd, J = 9.0, 2.3 Hz, 1H), 8.59 (d, J = 2.3 Hz, 1H), 10.5 (brs, 1H), 12.6 (s, 1H). |
| I-430 | 1H-NMR (CDCl3) δ: 1.70 (s, 2H), 2.03 (s, 2H), 2.30 (d, J = 12.0 Hz, 3H), 2.46 (s, 1H), 2.61 (s, 3H), 2.65 (s, 3H), 4.28 (s, 1H), 4.89 (s, 1H), 6.73 (d, J = 8.5 Hz, 1H), 6.85 (s, 1H), 7.75 (d, J = 8.5 Hz, 1H), 8.53 (s, 1H), 9.40 (s, 1H). |
| I-827 | 1H-NMR (CDCl3) δ: 2.45 (s, 2H), 2.61 (s, 3H), 2.66 (s, 2H), 2.66 (s, 3H), 3.74 (s, 3H), 5.28 (s, 1H), 6.81 (d, J = 8.5 Hz, 1H), 6.85 (s, 1H), 7.72 (d, J = 8.5 Hz, 1H), 8.49 (s, 1H), 8.97 (s, 1H). |
| I-830 | 1H-NMR (DMSO-D6) δ: 2.33 (s, 2H), 2.59 (s, 3H), 2.67 (s, 3H), 3.39-3.41 (m, 2H), 3.58 (s, 2H), 4.14-4.16 (m, 2H), 7.13 (s, 2H), 7.78 (d, J = 21.3 Hz, 1H), 8.06 (t, J = 10.4 Hz, 1H), 8.38 (d, J = 9.8 Hz, 1H), 11.65 (s, 1H). |
| I-811 | 1H-NMR (DMSO-D6) δ: 1.98 (d, J = 7.5 Hz, 3H), 2.52 (s, 3H), 2.59 (s, 3H), 2.64-2.95 (m, 2H), 3.16-3.27 (m, 1H), 3.55-3.84 (m, 3H), 3.86-4.06 (m, 2H), 4.37 (d, J = 14.6 Hz, 1H), 7.05-7.11 (m, 2H), 7.69 (d, J = 8.5 Hz, 1H), 8.25 (s, 1H), 11.49 (s, 1H). |
| I-157 | 1H-NMR (DMSO-D6) δ: 1.18 (t, J = 7.0 Hz, 2H), 1.45 (d, J = 6.3 Hz, 3H), 2.54 (s, 3H), 4.30 (s, 2H), 4.89 (d, J = 6.5 Hz, 1H), 6.69 (t, J = 8.9 Hz, 1H), 6.97 (d, J = 9.0 Hz, 1H), 7.06 (d, J = 8.3 Hz, 1H), 7.10 (s, 1H), 7.19 (d, J = 11.8 Hz, 1H), 7.73 (d, J = 8.3 Hz, 1H), 8.31 (s, 1H), |
| I-49 | 1H-NMR (DMSO-d6) δ: 1.80 (s, 3H), 2.51 (s, 3H), 2.59 (s, 3H), 4.69 (d, J = 14.6 Hz, 1H), 4.81 (d, J = 14.3 Hz, 1H), 7.00 (d, J = 8.3 Hz, 1H), 7.07 (s, 1H), 7.33-7.39 (m, 2H), 7.54 (dd, J = 8.5, 2.4 Hz, 1H), 7.60 (dd, J = 10.5, 2.0 Hz, 1H), 8.06 (d, J = 1.8 Hz, 1H), 11.5 (s, 1H). |
| I-271 | 1H-NMR (CDCl3) δ: 2.61 (s, 3H), 2.68 (s, 3H), 6.87 (s, 1H), 6.94 (d, J = 8.8 Hz, 1H), 7.20 (d, J = 8.8 Hz, 2H), 7.91 (br s, 1H), 8.16 (dd, J = 8.7, 2.4 Hz, 1H), 8.42 (t, J = 8.7 Hz, 1H), 8.91 (d, J = 2.3 Hz, 1H). |
| I-52 | 1H-NMR (DMSO-d6) δ: 2.51 (s, 3H), 2.60 (s, 3H), 2.79-2.92 (m, 4H), 7.00 (d, J = 8.9 Hz, 1H), 7.05 (s, 1H), 7.24 (d, J = 8.0 Hz, 2H), 7.32 (d, J = 7.9 Hz, 2H), 7.58 (d, J = 8.4 Hz, 1H), 8.12 (s, 1H), 11.4 (s, 1H). |
| I-331 | 1H-NMR (DMSO-D6) δ: 2.00-2.15 (m, 8H), 2.53 (s, 3H), 2.60 (s, 3H), 2.95 (s, 3H), 4.00 (s, 4H), 4.14 (s, 2H), 7.13 (d, J = 8.8 Hz, 1H), 7.16 (s, 1H), 8.06 (d, J = 8.7 Hz, 1H), 8.14 (s, 1H), 8.73 (s, 1H), 11.79 (s, 1H). |
| I-573 | 1H-NMR (CDCl3) δ: 1.74 (d, J = 8.3 Hz, 2H), 2.04 (s, 3H), 2.20 (s, 2H), 2.61 (s, 3H), 2.65 (s, 3H), 3.49 (s, 1H), 4.31 (s, 1H), 4.97 (s, 1H), 5.09 (s, 1H), 6.71 (d, J = 8.5 Hz, 1H), 6.85 (s, 1H), 7.74 (d, J = 8.5 Hz, 1H), 8.54 (s, 1H), 9.77 (s, 1H). |
| I-17 | 1H-NMR (DMSO-D6) δ: 2.53 (s, 3H), 2.60 (s, 3H), 4.75 (s, 2H), 7.14 (d, J = 8.8 Hz, 1H), 7.18-7.28 (m, 3H), 7.41 (d, J = 7.8 Hz, 2H), 7.86 (d, J = 8.8 Hz, 1H), 8.52 (s, 1H), 12.17 (s, |
| I-278 | 1H-NMR (CDCl3) δ: 2.61 (s, 3H), 2.67 (s, 3H), 6.78 (s, 1H), 6.86 (d, J = 9.0 Hz, 1H), 7.49 (d, J = 8.5 Hz, 2H), 7.71 (s, 1H), 7.83 (d, J = 8.5 Hz, 2H), 8.06 (d, J = 6.8 Hz, 1H), 8.48-8.49 (m, |
| I-329 | 1H-NMR (DMSO-D6) δ: 0.69-0.74 (m, 4H), 1.87-1.89 (m, 3H), 2.04-2.16 (m, 5H), 2.53 (s, 3H), 2.60 (s, 3H), 3.98 (s, 1H), 4.43 (s, 1H), 4.56 (s, 1H), 7.13 (d, J = 8.5 Hz, 1H), 7.16 (s, 1H), 8.07 (dd, J = 8.5, 2.3 Hz, 1H), 8.20 (d, J = 4.3 Hz, 1H), 8.30 (s, 1H), 8.74 (d, J = 2.0 Hz, 1H), |
| I-188 | 1H-NMR (CDCl3) δ: 1.53 (d, J = 6.4 Hz, 3H), 2.63 (d, J = 20.7 Hz, 6H), 4.01 (s, 1H), 4.46 (d, J = 5.8 Hz, 1H), 6.43 (d, J = 7.9 Hz, 2H), 6.72 (d, J = 8.4 Hz, 1H), 6.78 (s, 1H), 7.04 (d, J = 7.8 Hz, 2H), 7.57 (d, J = 8.4 Hz, 1H), 8.36 (s, 1H), 8.62 (s, 1H). |

TABLE 16

| | NMR |
|---|---|
| I-48 | 1H-NMR (DMSO-d6) δ: 2.51 (s, 3H), 2.59 (s, 3H), 4.29 (d, J = 5.8 Hz, 1H), 6.36-6.41 (m, 1H), 6.68 (dd, J = 9.2, 9.2 Hz, 1H), 6.97 (d, J = 8.7 Hz, 1H), 7.03 (d, J = 8.5 Hz, 1H), 7.07 (s, 1H), 7.20 (d, J = 11.8 Hz, 1H), 7.71 (d, J = 8.4 Hz, 1H), 8.30 (s, 1H), 11.5 (s, 1H). |
| I-274 | 1H-NMR (CDCl3) δ: 1.73 (s, 6H), 2.61 (s, 3H), 2.67 (s, 3H), 5.96 (s, 1H), 6.80 (d, J = 8.7 Hz, 1H), 6.86 (s, 1H), 8.00 (d, J = 8.7 Hz, 1H), 8.72 (s, 1H), 8.81 (s, 1H). |
| I-275 | 1H-NMR (DMSO-d6) δ: 2.52 (s, 3H), 2.59 (s, 3H), 5.05 (s, 2H), 7.06 (d, J = 9.0 Hz, 2H), 7.10 (d, J = 8.0 Hz, 1H), 7.10 (s, 1H), 7.35 (d, J = 9.0 Hz, 2H), 7.81 (dd, J = 8.5, 2.3 Hz, 1H), 8.41 (d, J = 1.8 Hz, 1H), 11.6 (s, 1H). |
| I-897 | 1H-NMR (DMSO-D6) δ: 1.56-1.66 (m, 4H), 1.69-1.81 (m, 2H), 1.85-1.96 (m, 2H), 2.53 (s, 3H), 2.60 (s, 3H), 3.77-3.85 (m, 1H), 7.15 (d, J = 8.8 Hz, 1H), 7.20 (s, 1H), 8.21 (dd, J = 8.8, 2.2 Hz, 1H), 8.98 (d, J = 2.2 Hz, 1H), 11.97 (s, 1H). |

Test Example 1 Measurement of TRPV4 Inhibitory Activity ($IC_{50}$ Value)

For each compound, TRPV4 inhibitory activity was measured using cells. (Method) TRPV4 inhibitory activity of the compound was evaluated in accordance with the following procedure.

(1) The TRPV4 inhibitory activity was measured using CHO-K1 cells stably expressing human TRPV4.

(2) In the day before the experimental day, frozen cell were thawed and washed with the culture medium (MEM-α, 10% FBS, 2 mmol/L GlutaMax, 50 unit Penicillin, 50 μg/mL Streptomycin, 20 mmol/L HEPES). Then cells were suspended in the culture medium.

(3) The 384-well plates which hTRPV4/CHO cells were seeded at densities of 4000 cells/well in the culture medium and cultured in a $CO_2$ incubator in the presence of 5% $CO_2$ at 37° C. for overnight was used as assay plates.

(4) The assay plate was washed with assay buffer (Hanks, 20 mmol/L HEPES, 2.5 mmol/L probenecid, pH 7.4), and the buffer were remained at 20 μL/well.

(5) 10 μl of dye loading buffer (9 μmol/L Fluo 4-AM, 0.09% Pluronic F-127/assay buffer) was added to each well, then the assay plate was incubated in a $CO_2$ incubator in the presence of 5% $CO_2$ at 37° C. for one hour (final 3 μmol/L Fluo4-AM).

(6) The assay plate was washed with the assay buffer, and the buffers were remained at 20 μL/well. Then the assay plate was incubated for 10 min at room temperature.

(7) 20 μL/well of diluted compound solution was dispensed to each well in the compound plate, and mixed with built-in Pipette and Mixer of the Fluorescence analysis system FLIPR TETRA (Molecular devices).

(8) After incubation for 5 min, 20 μL/well of 4α-PDD solution were applied to each well of assay plate and mixed with the FLIPR TETRA (final 1 μmol/L 4α-PDD).

(9) The fluorescent intensity was measured with FLIPR TETRA system for 5 min from the point of time addition the compound solution, at Ex 470-495 nm, Em 515-575 nm wavelength.

In addition, TRPV4 inhibitory activity ($IC_{50}$ value) of a compound was evaluated according to the following procedure.

(10) In the presence of the compound, the difference between maximal and minimal of fluorescent intensity value for 5 min from just before addition of 4α-PDD solution was calculated, and it was referred as Max−Min value. Max−Min value of the compound A at 1 μmol/L was defined as 100% inhibitory activity, Max−Min value in the absence of the compound was defined as 0% inhibitory activity. The TRPV4 inhibitory activity of the compound was calculated by the following formula.

Inhibition ratio=(1−(Max−Min value of the compound−100% inhibitory activity)/(0% inhibitory activity−100% inhibitory activity))×100

Herein, the compound A is the compound I-186 described in PCT/JP2013/058722.

(11) Inhibitory activity was calculated at 10 points with three fold serial dilution, in the final concentration of the compound from 10 μmol/L to 0.5 nmol/L, the $IC_{50}$ value (nmol/L) was calculated by logistic approximation method.

(Result)

TABLE 17

| No. | IC50 (nmol/L) |
| --- | --- |
| I-6 | 52 |
| I-10 | 14 |
| I-13 | 6.4 |
| I-17 | 37 |
| I-41 | 42 |
| I-43 | 39 |
| I-45 | 8.1 |
| I-48 | 1.2 |
| I-49 | 8.6 |
| I-54 | 27 |
| I-79 | 27 |
| I-118 | 9.1 |
| I-132 | 14 |
| I-134 | 6.8 |
| I-140 | 42 |
| I-150 | 30 |
| I-157 | 14 |
| I-184 | 4 |
| I-188 | 6.4 |
| I-200 | 2.5 |
| I-228 | 1.7 |
| I-257 | 14 |
| I-270 | 26 |
| I-274 | 3.3 |
| I-312 | 24 |

Test Example 2 Measurement of TRPV4 Inhibitory Activity ($IC_{50}$ Value)

For each compound, TRPV4 inhibitory activity was measured using cells. (Method) TRPV4 inhibitory activity of the compound was evaluated in accordance with the following procedure.

(1) The TRPV4 inhibitory activity was measured using CHO-K1 cells stably expressing human TRPV4.

(2) In the day before the experimental day, frozen cell were thawed and washed with the culture medium (DMEM, 10% FBS, 2 mmol/L GlutaMax, 50 unit Penicillin, 50 μg/mL Streptomycin, 0.1 mmol/L Non-Essential Amino Acids, 25 mmol/L HEPES). Then cells were suspended in the culture medium.

(3) The 384-well plates which hTRPV4/CHO cells were seeded at densities of 5000 cells/well in the culture medium and cultured in a $CO_2$ incubator in the presence of 5% $CO_2$ at 37° C. for overnight was used as assay plates.

(4) The assay plate was washed with assay buffer (Hanks, 20 mmol/L HEPES, 2.5 mmol/L probenecid, pH7.4), and the buffer were remained at 20 μL/well.

(5) 10 μl of dye loading buffer (3 μmol/L Fluo 4-AM, 0.03% Pluronic F-127/assay buffer) was added to each well, then the assay plate was incubated in a $CO_2$ incubator in the presence of 5% $CO_2$ at 37° C. for one hour (final 1 μmol/L Fluo4-AM).

(6) The assay plate was washed with the assay buffer, and the buffers were remained at 20 μL/well. Then the assay plate was incubated for 10 min at room temperature.

(7) 20 μL/well of diluted compound solution was dispensed to each well in the compound plate, and mixed with built-in Pipette and Mixer of the Fluorescence analysis system FLIPR TETRA (Molecular devices).

(8) After incubation for 5 min, 20 μL/well of 4α-PDD solution were applied to each well of assay plate and mixed with the FLIPR TETRA (final 0.15 μmol/L 4α-PDD).

(9) The fluorescent intensity was measured with FLIPR TETRA system for 5 min from the point of time addition the compound solution, at Ex 470-495 nm, Em 515-575 nm wavelength.

In addition, TRPV4 inhibitory activity ($IC_{50}$ value) of a compound was evaluated according to the following procedure.

(10) In the presence of the compound, the difference between maximal and minimal of fluorescent intensity value for 5 min from just before addition of 4α-PDD solution was calculated, and it was referred as Max−Min value. Max−Min value of the above compound A at 1 μmol/L was defined as 100% inhibitory activity, Max−Min value in the absence of the compound was defined as 0% inhibitory activity. The TRPV4 inhibitory activity of the compound was calculated by the following formula.

Inhibition ratio=(1−(Max−Min value of the compound−100% inhibitory activity)/(0% inhibitory activity−100% inhibitory activity))×100

(11) Inhibitory activity was calculated at 10 points with three fold serial dilution, in the final concentration of the compound from 10 μmol/L to 0.5 nmol/L, the $IC_{50}$ value (nmol/L) was calculated by logistic approximation method.

(Result)

TABLE 18

| No. | IC50 (nmol/L) |
| --- | --- |
| I-592 | 3.9 |
| I-662 | 6.7 |
| I-703 | 13 |
| I-719 | 1.6 |

TABLE 18-continued

| No. | IC50 (nmol/L) |
|---|---|
| I-744 | 4.2 |
| I-799 | 6.3 |
| I-831 | 2.9 |
| I-843 | 2.6 |

Test Example 2' Measurement of TRPV4 Inhibitory Activity ($IC_{50}$ Value)

For each compound, TRPV4 inhibitory activity was measured using cells. (Method) TRPV4 inhibitory activity of the compound was evaluated in accordance with the following procedure.
(1) The TRPV4 inhibitory activity was measured using CHO-K1 cells stably expressing human TRPV4.
(2) In the day before the experimental day, frozen cell were thawed and washed with the culture medium (DMEM, 3% FBS, 2 mmol/L GlutaMax, 50 unit Penicillin, 50 µg/mL Streptomycin, 0.1 mmol/L Non-Essential Amino Acids, 25 mmol/L HEPES). Then cells were suspended in the culture medium.
(3) The 384-well plates which hTRPV4/CHO cells were seeded at densities of 3000 cells/well in the culture medium and cultured in a $CO_2$ incubator in the presence of 5% $CO_2$ at 37° C. for overnight was used as assay plates.
(4) The assay plate was washed with assay buffer (Hanks, 20 mmol/L HEPES, 2.5 mmol/L probenecid, pH7.4), and the buffer were remained at 20 µL/well.
(5) 10 µl of dye loading buffer (3 µl mol/L Fluo 4-AM, 0.03% Pluronic F-127/assay buffer) was added to each well, then the assay plate was incubated in a $CO_2$ incubator in the presence of 5% $CO_2$ at 37° C. for one hour (final 1 µmol/L Fluo4-AM).
(6) The assay plate was washed with the assay buffer, and the buffers were remained at 20 µL/well. Then the assay plate was incubated for 10 min at room temperature.
(7) 20 µL/well of diluted compound solution was dispensed to each well in the compound plate, and mixed with built-in Pipette and Mixer of the Fluorescence analysis system FLIPR TETRA (Molecular devices).
(8) After incubation for 5 min, 20 µL/well of 4α-PDD solution were applied to each well of assay plate and mixed with the FLIPR TETRA (final 0.15 µmol/L 4α-PDD).
(9) The fluorescent intensity was measured with FLIPR TETRA system for 5 min from the point of time addition the compound solution, at Ex 470-495 nm, Em 515-575 nm wavelength.
In addition, TRPV4 inhibitory activity ($IC_{50}$ value) of a compound was evaluated according to the following procedure.
(10) In the presence of the compound, the difference between maximal and minimal of fluorescent intensity value for 5 min from just before addition of 4α-PDD solution was calculated, and it was referred as Max–Min value. Max–Min value of the above compound A at 1 µmol/L was defined as 100% inhibitory activity, Max–Min value in the absence of the compound was defined as 0% inhibitory activity. The TRPV4 inhibitory activity of the compound was calculated by the following formula.

Inhibition ratio=(1−(Max−Min value of the compound−100% inhibitory activity)/(0% inhibitory activity−100% inhibitory activity))×100

(11) Inhibitory activity was calculated at 10 points with three fold serial dilution, in the final concentration of the compound from 10 µmol/L to 0.5 nmol/L, the $IC_{50}$ value (nmol/L) was calculated by logistic approximation method.
(Result)

TABLE 19

| No. | IC50 (nmol/L) |
|---|---|
| I-897 | 2.8 |

Test Example 3 CYP3A4 Fluorescent MBI Test

The CYP3A4 fluorescent MBI test is a test of investigating enhancement of CYP3A4 inhibition of a compound of the present invention by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (7-HFC) emitting fluorescent light.
The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 µmol/mL, at reaction 6.25 pmol/mL (at 10-fold dilution); test drug concentration, 0.625, 1.25, 2.5, 5, 10, 20 µmol/L (six points).
An enzyme in a K-Pi buffer (pH 7.4) and a solution of a compound of the present invention as a pre-reaction mixture were added to a 96-well plate at the above composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 (v/v) was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 (v/v) was added to stop the reaction. For the plate on which each index reaction had been performed, a fluorescent value of 7-HFC which is a metabolite was measured with a fluorescent plate reader. (Ex=420 nm, Em=535 nm).
Addition of only DMSO which is a solvent dissolving a compound of the present invention to a reaction system was adopted as a control (100%), remaining activity (%) was calculated at each concentration of a compound of the present invention added as the solution, and $IC_{50}$ was calculated by reverse-presumption by a logistic model using a concentration and an inhibition rate. When a difference between $IC_{50}$ values is 5 µmol/L or more, this was defined as (+) and, when the difference is 3 µmol/L or less, this was defined as (−).
(Result)
Compound I-157: (−)

Test Example 4 CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a compound of the present invention was assessed.

The reaction conditions were as follows: substrate, 0.5 μmol/L ethoxyresorufin (CYP1A2), 100 μmol/L tolbutamide (CYP2C9), 50 μmol/L S-mephenytoinmephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; concentration of a compound of the present invention, 1, 5, 10, 20 μmol/L (four points).

Each five kinds of substrates, human hepatic microsome, or a compound of the present invention in 50 mmol/L Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and toltributamide hydroxide (CYP2C9 metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a compound of the present invention to a reaction system was adopted as a control (100%), remaining activity (%) was calculated at each concentration of a compound of the present invention added as the solution and $IC_{50}$ was calculated by reverse presumption by a logistic model using a concentration and an inhibition rate.

Test Example 5 Fluctuation Ames Test

Mutagenicity of compounds of the present invention was evaluated.

20 μL of freezing-stored rat typhoid *bacillus* (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 7.70 mL of a bacterial solution of the TA98 strain was centrifuged (2000×g, 10 minutes) to remove a culturing solution. The bacteria was suspended in 7.7 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4 \cdot 7H_2O$: 0.1 g/L), the suspension was added to 120 mL of an Exposure medium (Micro F buffer containing Biotin: 8 μg/mL, histidine: 0.2 μg/mL, glucose: 8 mg/mL). The TA100 strain was added to 130 mL of the Exposure medium relative to 3.42 mL of the bacterial solution to prepare a test bacterial solution. Each 12 μL of DMSO solution of a compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μL of the test bacterial solution and 90 μL of S9 mix under the metabolism activating condition) were mixed, and this was shaking-cultured at 37° C. for 90 minutes. 460 μL of the bacterial solution exposed to a compound of the present invention was mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group.

Test Example 6-1 Solubility Test

The solubility of each compound of the present invention was determined under 1% DMSO addition conditions. A 10 mmol/L solution of the compound was prepared with DMSO, and 2 μL of the compound of the present invention solution was added to 198 μL of an artificial intestinal juice (water and 118 mL of 0.2 mol/L NaOH reagent were added to 250 mL of 0.2 mol/L potassium dihydrogen phosphate reagent to reach 1000 mL) with a pH of 6.8. The mixture was shaken for 16 hours at 25° C., and the mixture was vacuum-filtered. The filtrate was two-fold diluted with methanol/water=1/1 (V/V), and the compound concentration in the filtrate was measured with LC/MS by the absolute calibration method.

Test Example 6-2 Solubility Test

The solubility of each compound of the present invention was determined under 1% DMSO addition conditions. A 10 mmol/L solution of the compound was prepared with DMSO, and 2 μL of the compound of the present invention solution was added to 198 μL of an artificial intestinal juice (water and 118 mL of 0.2 mol/L NaOH reagent were added to 250 mL of 0.2 mol/L potassium dihydrogen phosphate reagent to reach 1000 mL) with a pH of 6.8. The mixture was shaken for 1 hour at room temperature, and the mixture was vacuum-filtered. The filtrate was two-fold diluted with methanol/water=1/1 (V/V), and the compound concentration in the filtrate was measured with LC/MS by the absolute calibration method.

Test Example 6-3 Solubility Test

The solubility of each compound of the present invention was determined under 1% DMSO addition conditions. A 10 mmol/L solution of the compound was prepared with DMSO, and 2 μL of the compound of the present invention solution was added to 198 μL of an artificial intestinal juice (3.40 g of potassium dihydrogen phosphate reagent and 3.55 g of sodium dihydrogen phosphate anhydrous are dissolved in water to reach 1000 mL) with a pH of 6.8. The mixture was shaken for 1 or more hour(s) at room temperature, and the mixture was vacuum-filtered. The filtrate was ten-fold diluted with methanol/water=1/1 (V/V), and the compound concentration in the filtrate was measured with LC/MS by the absolute calibration method.

Test Example 7 Metabolism Stability Test

Using commercially available pooled human hepatic microsomes, a compound of the present invention was reacted for a constant time, and a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The compound of the present invention in the supernatant was quantified by LC/MS/MS, and a remaining amount of the compound of the present invention after the reaction was calculated, letting a compound amount at 0 minute reaction time to be 100%. Hydrolysis reaction was performed in the absence of NADPH and glucuronidation reaction was in the presence of 5 mmol/L UDP-glucuronic acid in place of NADPH, followed by similar operations. (Result) % inhibition was shown at 0.5 μmol/L of test compound.
Compound I-69: 106%
Compound I-157: 83.6%
Compound I-48: 78.6%

Test Example 8 hERG Test

For the purpose of assessing risk of an electrocardiogram QT interval prolongation of the compound of the present invention, effects of the compound of the present invention on delayed rectifier K$^+$ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S), $I_{Kr}$ induced by depolarization pulse stimulation at +20 mV for 2 seconds and, further, repolarization pulse stimulation at −50 mV for 2 seconds, was recorded. After the generated current was stabilized, extracellular solution (NaCl: 145 mmol/L, KCl: 4 mmol/L, CaCl$_2$2: 2 mmol/L, MgCl$_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration, was applied to the cell at room temperature for 10 minutes. From the recording $I_{Kr}$, an absolute value of the tail peak current was measured based on the current value at the resting membrane potential using analysis software (Falster Patch; Sophion Bioscience A/S). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$. (Result) % inhibition was shown at 1 μmol/L of test compound.
Compound I-48: 8.1%

Test Example 9 BA Test

Materials and methods for experiments to evaluate oral absorption
(1) Experimental animals: mice or SD rats were used.
(2) Rearing condition: mice or SD rats were allowed free access to solid feed and sterilized tap water.
(3) Setting of dosage and grouping: Oral administration and intravenous administration were performed with the predetermined dosage. Grouping was set as below. (Dosage was changed per compound)
  Oral administration 1 to 30 mg/kg (n=2 to 3)
  Intravenous administration 0.5 to 10 mg/kg (n=2 to 3)
(4) Preparation of administration solutions: Oral administration was performed as solution or suspension. Intravenous administration was performed after solubilization.
(5) Routes of administration: Oral administration was performed mandatory into the stomach by oral sonde. Intravenous administration was performed from caudal vein by syringes with needle.
(6) Evaluation items: Blood was collected serially and concentration of a compound of the present invention in plasma was measured by LC/MS/MS.
(7) Statistical analysis: About transition of concentration of a compound of the present invention in plasma, the area under the plasma concentration versus time curve (AUC) was calculated by non-linear least-squares method program, WinNonlin (a registered trademark), and bioavailability (BA) of a compound of the present invention was calculated from AUCs of the oral administration group and the intravenous administration group.

Test Example 10: Powder Solubility Test

Appropriate quantity of the compound of the present invention is put in a suitable container and 200 μL of JP-1 solution (water is added to 2.0 g of sodium chloride and 7.0 mL of hydrochloric acid to reach 1000 mL), JP-2 solution (500 mL of water is added to 500 mL of phosphate buffer with a pH of 6.8) or 20 mmol/L sodium taurocholate (TCA)/JP-2 solution (JP-2 solution is added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 μL of methanol is added to 100 μL of each filtrate to dilute two-fold. The dilution rate is changed as necessary. After checking that there is no bubble and deposit, the container is sealed and shaken. The compound of the present invention is measured using HPLC by absolute calibration curve method.

Formulation Example 1

A granule containing the following ingredient is prepared.

| Ingredient | |
|---|---|
| Compound represented by any of the formula (I) or (III) | 10 mg |
| Lactose | 700 mg |
| Corn starch | 274 mg |
| HPC-L | 16 mg |

The compound represented by any of the formula (I) or (III), and lactose are passed through a 60 mesh sieve. Corn starch is passed through a 120 mesh sieve. These are mixed with a V-type mixing machine. An aqueous solution of HPC-L (low viscosity hydroxypropylcellulose) is added to a mixture powder, and this is kneaded, granulated (extrusion granulation, pore diameter 0.5 to 1 mm), and dried. The resulting dry granule is sieved with a vibration sieve (12/60 mesh) to obtain a granule.

Formulation Example 2

A powder for filling into a capsule containing the following ingredients is prepared.

| Ingredient | |
|---|---|
| Compound represented by any of the formula (I) or (III) | 15 mg |
| Lactose | 90 mg |
| Corn starch | 42 mg |
| HPC-L | 3 mg |

The compound represented by any of the formula (I) or (III), and lactose are passed through a 60 mesh sieve. Corn starch is passed through a 120 mesh sieve. These and HPC-L are mixed, kneaded, granulated, and dried. The resulting dry granule is granulate, then 150 mg of them is filled into a No. 4 hard gelatin capsule.

Formulation Example 3

A tablet containing the following ingredients is prepared.

| Ingredient | |
|---|---|
| Compound represented by any of the formula (I) or (III) | 10 mg |
| Lactose | 90 mg |
| Microcrystaline cellulose | 30 mg |
| CMC—Na | 15 mg |
| Magnesium stearate | 5 mg |

The compound represented by any of the formula (I) or (III), lactose, microcrystalline cellulose, CMC-Na (carboxymethylcellulose sodium salt) are passed through a 60 mesh sieve, and mixed. Magnesium stearate is mixed into a mixture powder to obtain a mixture powder for tabletting. The present mixed powder is directly compressed to obtain a 150 mg tablet.

Formulation Example 4

The following ingredients are warmed, mixed, and sterilized to obtain an injectable.

| Ingredient | |
|---|---|
| Compound represented by any of the formula (I) or (III) | 3 mg |
| Nonionic surfactant | 15 mg |
| Purified water for injection | 1 ml |

A cataplasm containing the following ingredients is prepared.

| Ingredient | |
|---|---|
| Compound represented by any of the formula (I) or (III) | 50 mg |
| aqueous-based (5% ethanol/5% butylene glycol/90% purified water) | 950 mg |
| glycerin | |
| kaoline | |
| aqueous polyvinyl alcohol | |

The compound represented by any of the formula (I) or (III) is added to aqueous-based. The mixture is irradiated by ultrasonic for 15 minutes and then is sufficiently stirred to obtain a solution. 5 part of glycerin, 1 part of kaoline and 5 part of aqueous polyvinyl alcohol are homogeneously mixed and 1 part of the resulting solution is added to the above solution including the compound represented by any of the formula (I) or (III). The obtained solution is mixed and to give a paste form and the resulting paste is applied to an onwoven fabric. The resulting composition is covered by polyester film to give a cataplasm.

INDUSTRIAL APPLICABILITY

The compound of the invention has TRPV4 inhibitory activity and is useful in the treatment and/or prevention of a TRPV4 receptor-mediated disorder such as inflammatory pain (bladder inflammatory pain, pain after tooth extraction, postoperative pain, pain in the low back, periarthritis scapulohumeralis, cervico-omo-brachial syndrome, inflammation of a tendon or a tendon sheath, osteoarthritis, chronic articular rheumatism), neuropathic pain (sciatica, postherpetic neuralgia, diabetic neuropathy), pain related to cancer (cancer pain, bone metastasis pain, pain with the administration of anticancer agent), IBS, inflammatory bowel disease, osteoporosis, articular cartilage degeneration, cerebral stroke, incontinence, overactive bladder, urinary disturbance by bladder inflammation, asthma, dry skin, atopic dermatitis, metastasis and invasion of cancer, corneal ulcer, obesity, insulin resistance, diabetes, or the like.

The invention claimed is:
1. A compound of formula (I):

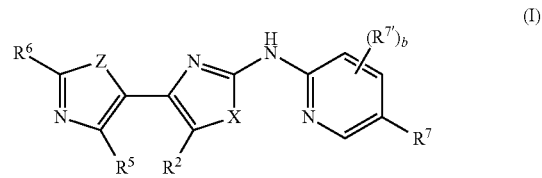

wherein:
—X— is —NH— or —S—;
—Z— is —O— or —S—;
$R^3$, $R^5$ and $R^6$ are each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^7$ is a cyano, substituted or unsubstituted amino, substituted or unsubstituted alkyl (with the proviso that unsubstituted methyl is excluded), substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkylsulfonyl, substituted or unsubstituted carbamoyl, substituted or unsubstituted sulfamoyl, substituted or unsubstituted aromatic carbocyclyl carbonyl, substituted or unsubstituted non-aromatic carbocyclylcarbonyl, substituted or unsubstituted aromatic heterocyclyl carbonyl, or substituted or unsubstituted non-aromatic heterocyclylcarbonyl;

$R^{7'}$ is each independently a halogen;
b is 0 or 1;
or a pharmaceutically acceptable salt thereof.

2. The compound according to claim 1,
wherein
—X— is —S—;
—Z— is —S—,
or a pharmaceutically acceptable salt thereof.

3. The compound according to claim 2,
wherein
$R^7$ is a group represented by the following formula:

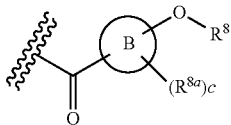

wherein
ring B is non-bridged non-aromatic heterocyclyl, or bridged non-aromatic heterocyclyl;
$R^8$ is substituted or unsubstituted alkyl, substituted or unsubstituted alkenyl, substituted or unsubstituted alkynyl, substituted or unsubstituted aromatic carbocyclyl, or substituted or unsubstituted aromatic heterocyclyl;
$R^{8a}$ is each independently halogen, substituted or unsubstituted alkyl, substituted or unsubstituted alkenyl, or substituted or unsubstituted alkynyl;
c is 0, 1, or 2;
or a pharmaceutically acceptable salt thereof.

4. The compound according to claim 3,
wherein
$R^7$ is a group represented by the following formula:

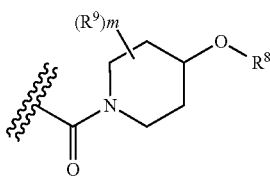

wherein
m is 2;
two $R^9$ groups may be taken together to form (C2-C4) bridge;
the carbon atoms that consist of the bridge are each independently substituted with the substituent selected from $R^a$;
$R^a$ is a hydrogen atom, halogen, substituted or unsubstituted alkyl, substituted or unsubstituted alkenyl, or substituted or unsubstituted alkynyl;
$R^8$ is substituted or unsubstituted alkyl, substituted or unsubstituted alkenyl, substituted or unsubstituted alkynyl, substituted or unsubstituted aromatic carbocyclyl, or substituted or unsubstituted aromatic heterocyclyl;
or a pharmaceutically acceptable salt thereof.

5. A compound of formula (III):

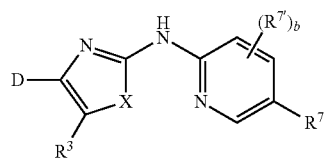

wherein
$R^7$ is substituted or unsubstituted non-aromatic heterocyclylcarbonyl;
D is a group represented by the following formula:

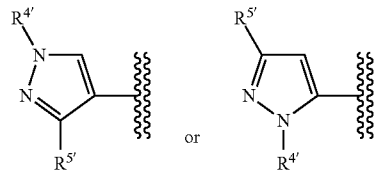

wherein
$R^{4'}$ is a hydrogen atom, or substituted or unsubstituted alkyl, substituted or unsubstituted alkenyl, or substituted or unsubstituted alkynyl;
$R^{5'}$ is a hydrogen atom, or substituted or unsubstituted alkyl, substituted or unsubstituted alkenyl, or substituted or unsubstituted alkynyl;
—X— is —NH— or —S—;
$R^3$ is each independently a hydrogen atom, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^{7'}$ is each independently a halogen;
b is 0 or 1;
or a pharmaceutically acceptable salt thereof.

6. A pharmaceutical composition containing the compound according to claim 1, or a pharmaceutically acceptable salt thereof.

7. A pharmaceutical composition containing the compound according to claim 2, or a pharmaceutically acceptable salt thereof.

8. A pharmaceutical composition containing the compound according to claim 3, or a pharmaceutically acceptable salt thereof.

9. A pharmaceutical composition containing the compound according to claim 4, or a pharmaceutically acceptable salt thereof.

10. A pharmaceutical composition containing the compound according to claim 5, or a pharmaceutically acceptable salt thereof.

* * * * *